United States Patent
Hoshino et al.

(10) Patent No.: US 9,044,154 B2
(45) Date of Patent: Jun. 2, 2015

(54) JOINT IMAGING APPARATUS

(71) Applicants: Yoshihide Hoshino, Hachioji (JP); Satoshi Nishino, Sayama (JP)

(72) Inventors: Yoshihide Hoshino, Hachioji (JP); Satoshi Nishino, Sayama (JP)

(73) Assignee: KONICA MINOLTA, INC. (JP)

( * ) Notice: Subject to any disclaimer, the term of this patent is extended or adjusted under 35 U.S.C. 154(b) by 159 days.

(21) Appl. No.: 13/777,078

(22) Filed: Feb. 26, 2013

(65) Prior Publication Data

US 2013/0230135 A1    Sep. 5, 2013

(30) Foreign Application Priority Data

Mar. 1, 2012 (JP) .................................. 2012-045313

(51) Int. Cl.
*A61B 6/04* (2006.01)
*A61B 6/00* (2006.01)

(52) U.S. Cl.
CPC . *A61B 6/04* (2013.01); *A61B 6/484* (2013.01); *A61B 6/585* (2013.01); *A61B 6/582* (2013.01)

(58) Field of Classification Search
CPC .......... A61B 6/04; A61B 6/484; A61B 6/585; A61B 6/582
USPC ........................ 378/36, 37, 62, 177, 180, 208
See application file for complete search history.

(56) References Cited

U.S. PATENT DOCUMENTS

| | | | | |
|---|---|---|---|---|
| 5,099,135 | A | * | 3/1992 | Gemmill .................... 250/516.1 |
| 5,485,856 | A | * | 1/1996 | Buckland .......................... 5/647 |
| 2003/0021383 | A1 | * | 1/2003 | Masson et al. ................ 378/177 |
| 2010/0119041 | A1 | * | 5/2010 | Ohara ............................. 378/87 |

FOREIGN PATENT DOCUMENTS

| | | |
|---|---|---|
| JP | 58-16216 A | 1/1983 |
| JP | 2007-203063 A | 8/2007 |
| JP | 2007-268033 A | 10/2007 |
| JP | 2008-18060 A | 1/2008 |
| JP | 2008-23312 A | 2/2008 |
| WO | 2004/058070 A1 | 7/2004 |

OTHER PUBLICATIONS

K. Hibino et al., "Phase shifting for nonsinusoidal waveforms with phase-shift errors" J. Opt. Soc. Am. A, vol. 12, No. 4, pp. 761-768 (1995); 8 pages.

Atsushi et al., "Phase Tomography by X-ray Talbot Interferometry for Biological Imaging" Japan Journal of Applied Physics, vol. 45, No. 6A, pp. 5254-5262 (2006); 9 pages.

* cited by examiner

*Primary Examiner* — Irakli Kiknadze
(74) *Attorney, Agent, or Firm* — Cantor Colburn LLP

(57) ABSTRACT

A joint imaging apparatus includes a subject table and a radiographic unit including a radiation generating section disposed above the subject table to irradiate a joint of a finger, and a detecting section disposed under the subject table to detect radiation passing through the joint. The subject table includes a base unit to fix the wrist, and a subject fixing unit to fix the joint to a predetermined position. The subject fixing unit includes a first fixing member to fix a part on the trunk side of the joint, and a second fixing member to fix a part on the side, opposite to the trunk side, of the joint. A position of the second fixing member is adjustable relative to that of the first fixing member.

8 Claims, 42 Drawing Sheets

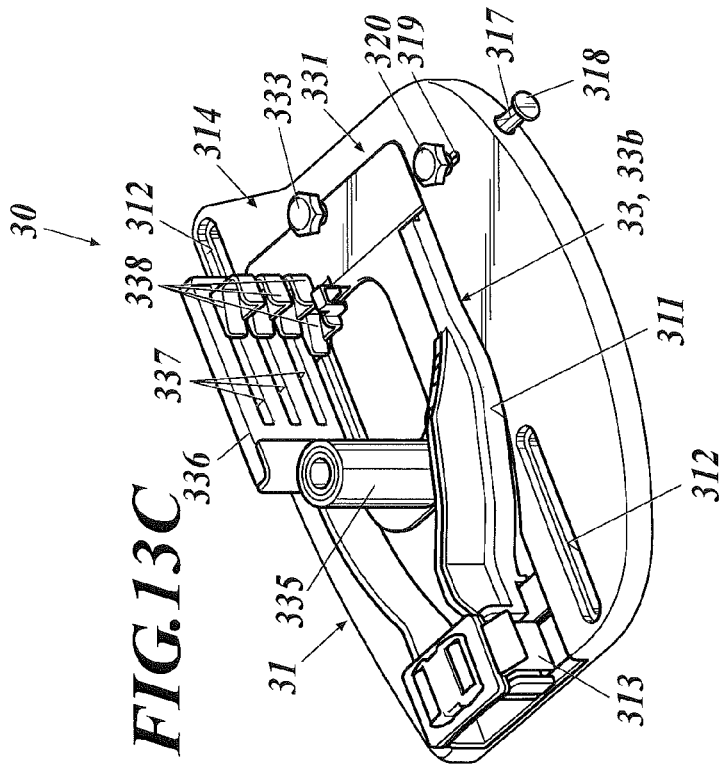
FIG.13A
FIG.13B
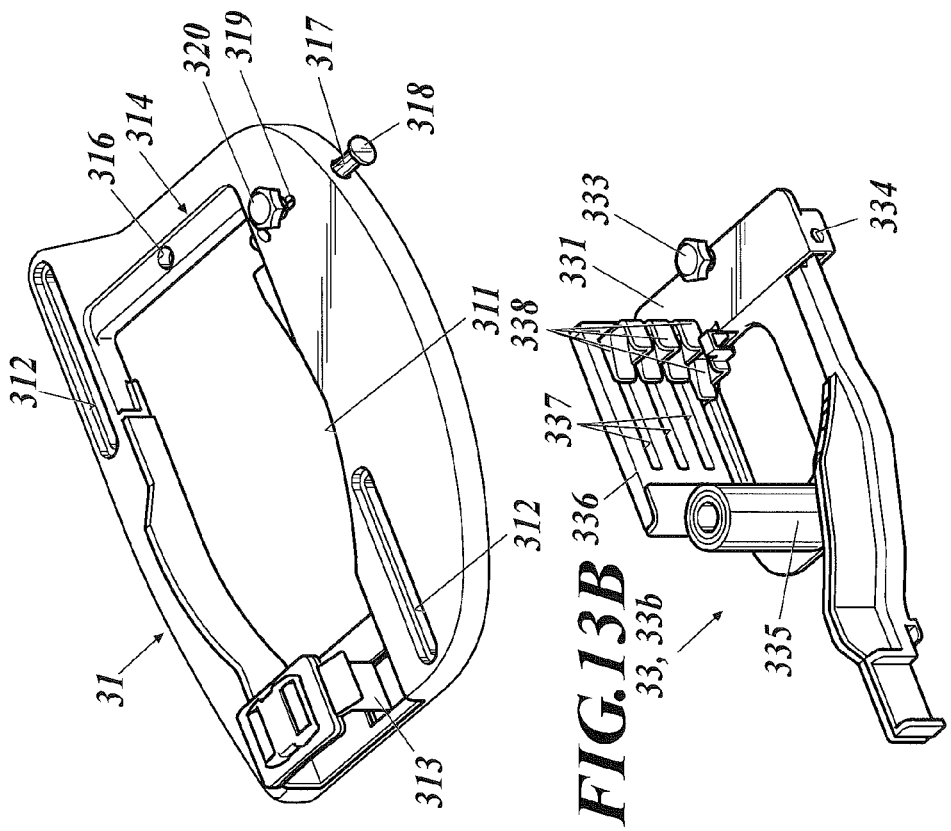
FIG.13C

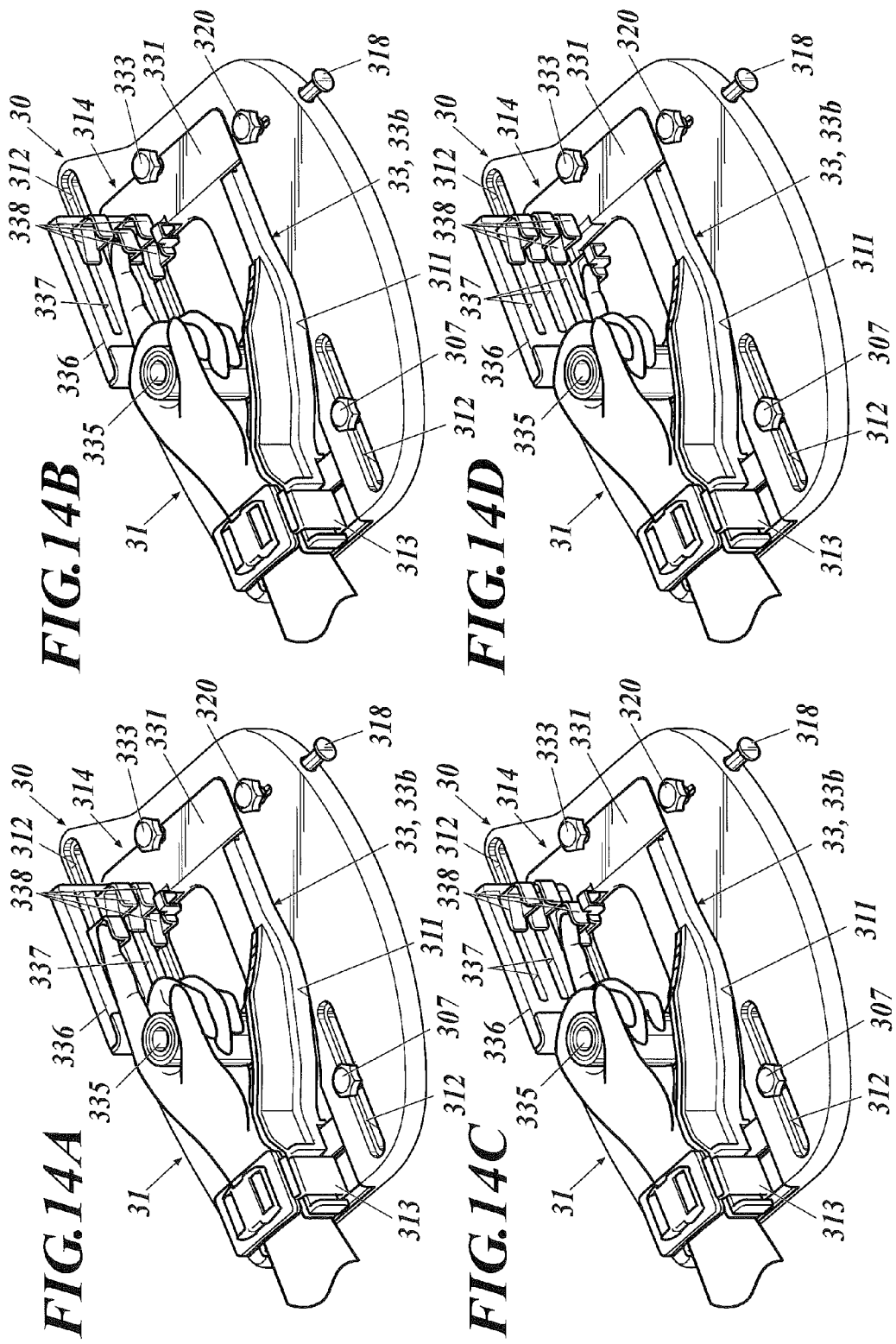

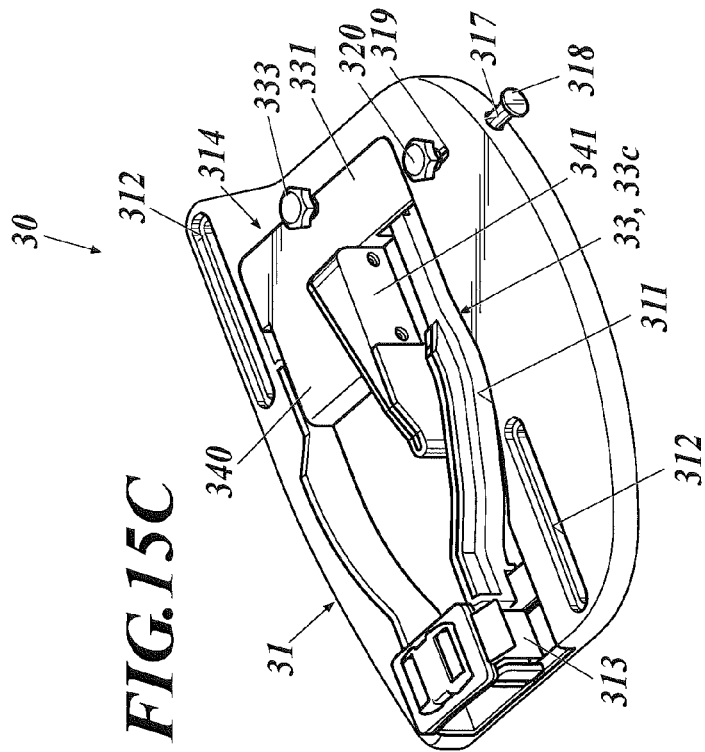
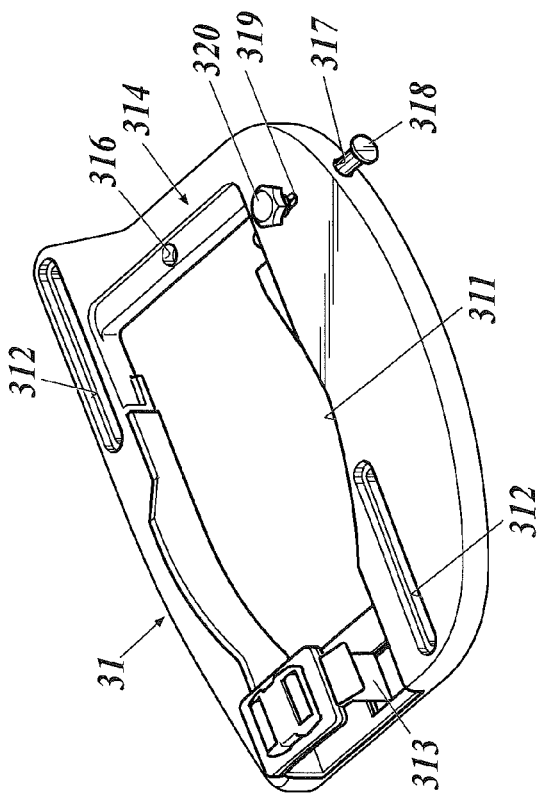
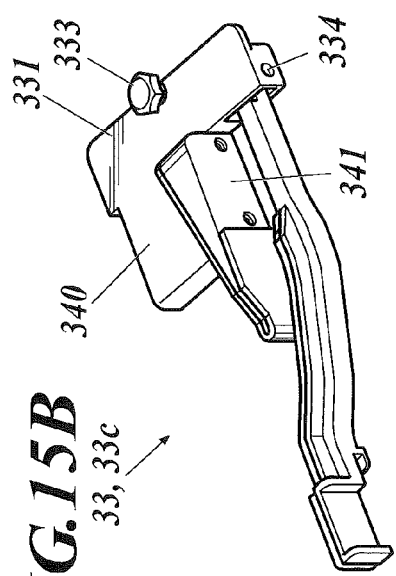

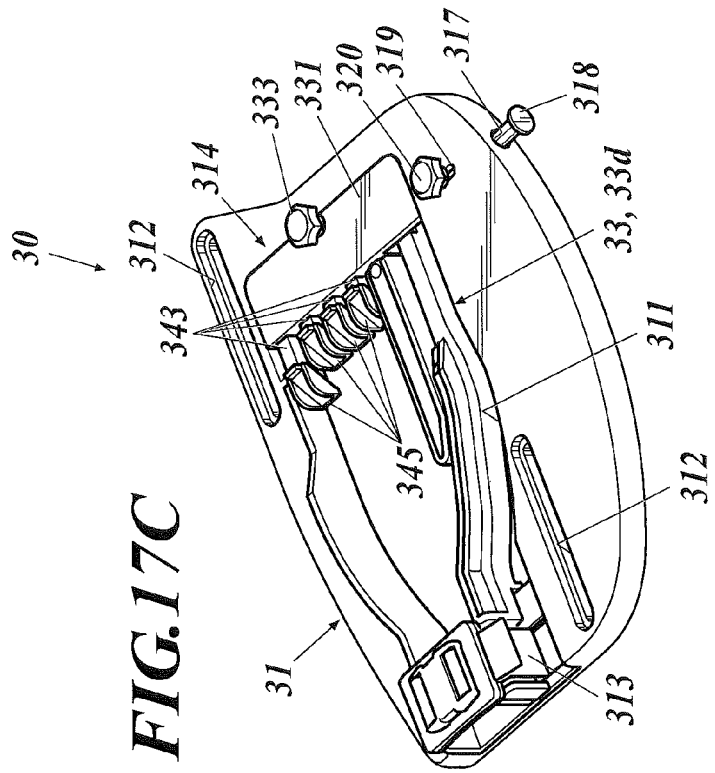
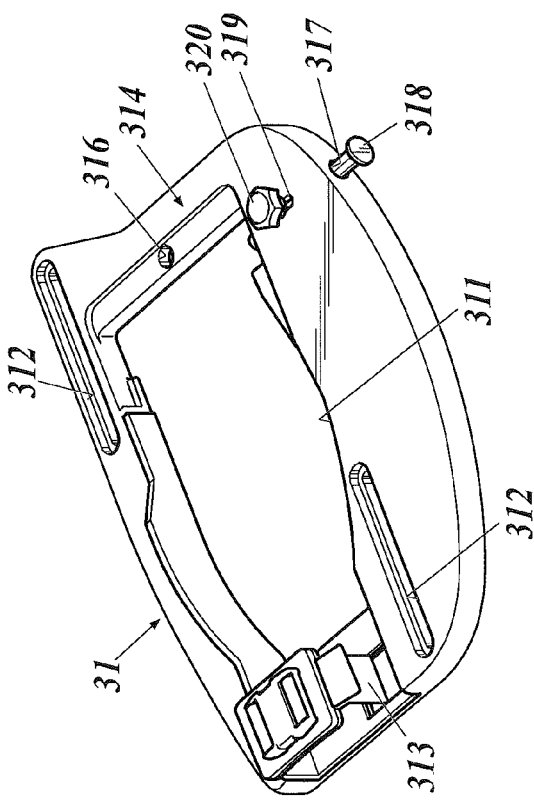
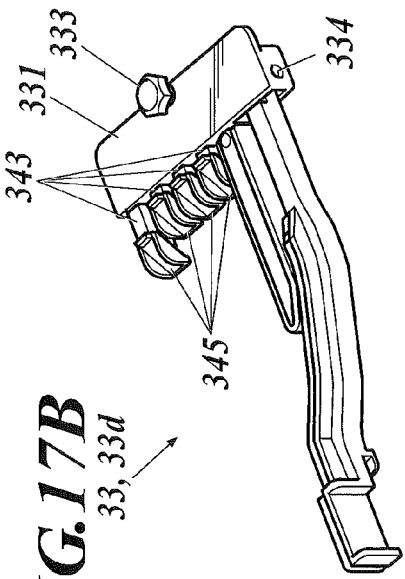

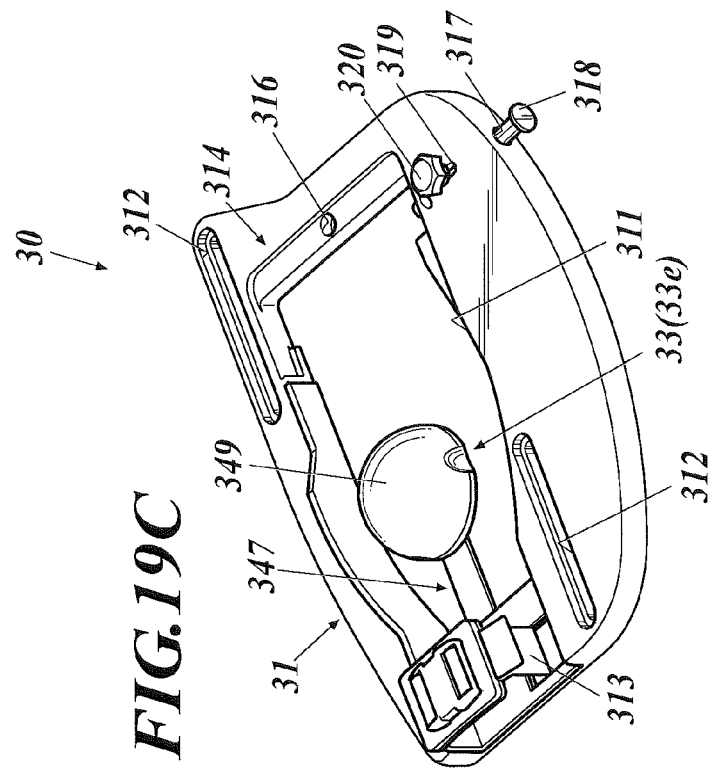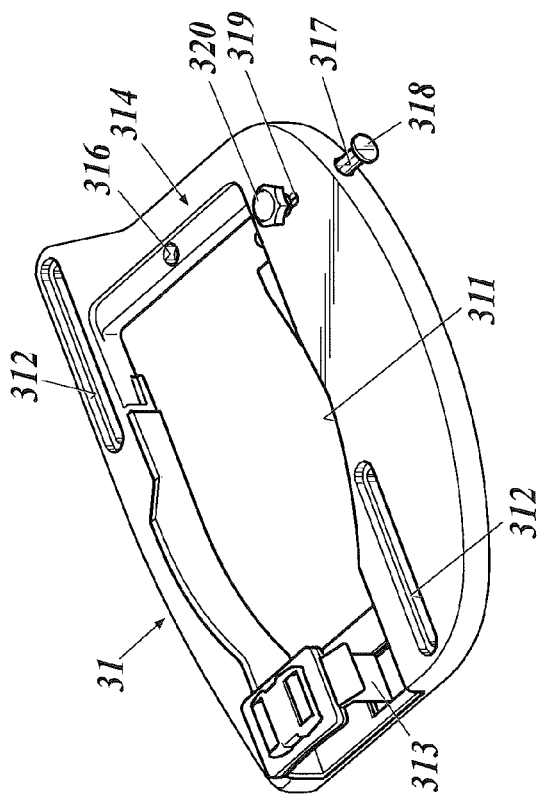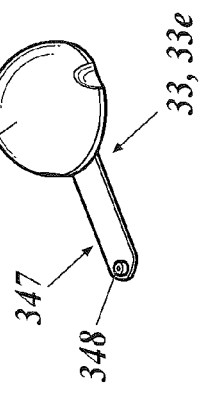

FIG. 42A 1 STEP  FIG. 42B 2 STEP  FIG. 42C 3 STEP  FIG. 42D 4 STEP  FIG. 42E 5 STEP

JOINT IMAGING APPARATUS

CROSS REFERENCE TO RELATED APPLICATIONS

The present invention claims priority under 35 U.S.C. §119 to Japanese Application No. 2012-045313 filed Mar. 1, 2012, the entire content of which is incorporated herein by reference.

BACKGROUND OF THE INVENTION

1. Field of the Invention

The present invention relates to a joint imaging apparatus.

2. Description of Related Art

Images taken by magnetic resonance imaging (MRI) have mainly been used for diagnosis of rheumatoid arthritis because conventional radiographic techniques using an absorption contrast method cannot create images suitable for diagnosis of cartilages in joints of limbs and soft tissues around joints.

Unfortunately, MRI forces a heavy burden on a patient because of holding a posture of the patient under restraint mechanically for a predetermined time period and costs a great deal of money; hence, technology is needed that diagnoses rheumatism using X-ray images taken with common X-ray tubes.

For example, radiography by phase contrast imaging has been proposed as a substitute for MRI (e.g., see Japanese Patent Laid-Open Nos. 2008-023312, 2007-268033, and 2008-18060).

The phase contrast imaging can produce X-ray images with high visibility based on edge enhancement utilizing the refraction of X-rays in the phase-contrast magnification radiography.

Talbot or Talbot-Lau interferometers utilizing the Talbot effect have also been studied as phase contrast imaging (e.g., see Japanese Patent Laid-Open Nos. 58-16216 and 2007-203063, and WO2004/058070). The Talbot effect refers to a phenomenon of coherent light that passes through a first grating having regularly aligned slits, in which the image of the grating is formed at regular intervals in the advancing direction of the light. The grating image is called "self-image," and the Talbot interferometer measures interference fringes (moire) occurring by slightly shifting a second grating disposed at a position where a self-image is formed. Since a subject in front of the second grating causes the distortion of the moire pattern, the subject is disposed in front of the first grating and irradiated with coherent X-rays during radiography with the Talbot interferometer, and then an image of the subject can be reconstructed by arithmetic processing of the resulting moire image.

Furthermore, a method using the Fourier transform has been developed where a one- or two-dimensional grating is used, which eliminates the need for scanning essential for the method that uses a Talbot interferometer.

The radiography using such a phase contrast method can image breast tissues, joint cartilages, and soft tissues around joints, which cannot readily produce clear images due to a low difference in absorption of X-rays in the absorption-contrast method. Thus, it is expected that medical costs and burdens on patients be reduced by using X-ray images produced by the phase contrast method using common radiography for diagnosis of lesions such as rheumatism in cartilages or soft tissues.

In some cases, images for diagnosis of rheumatism are taken for potential patients with rheumatism in order to prevent the occurrence of and to achieve early detection of this disease. In other cases, such images are taken for patients with rheumatism to check the development stage of this disease (e.g., effect of doses).

Nevertheless, unlike able-bodied people, a patient who already has a lesion in a joint such as rheumatoid arthritis has great difficulty in stretching the joint along a subject table by his/her own.

In radiography of a joint such as a metacarpophalangeal (MCP) or a proximal interphalangeal (PIP) joint, a radiographer needs to perform the positioning of the patient such that the irradiation axis virtually coincides with the top of the joint, which is a region of interest (ROI) to be radiographed. The patient, however, has difficulty in maintaining the posture by his/her own, and thus the region of interest might move after the radiographer leaves the patient for the operation of an emission switch. In addition, the subject might move during multiple scans and exposures required by the method that uses a Talbot (Talbot-Lau) interferometer.

The method using the Fourier transform, which needs only one exposure without scanning, also takes a long time to reach a predetermined dose of irradiation (i.e., a radiographing time), and thus movement of the subject within this time period leads to a blurred image.

Furthermore, the optimum position of patient fingers on the subject table (in particular, the position in the z direction) needs to be found for each patient by varying a bending angle of a joint, in order to obtain a highly visible image of a cartilage for the purpose of early detection of the disease. The present inventors, however, have found that a clear image of a joint, especially a cartilage, can be obtained irrespective of the above-mentioned variations depending on patients if a stretched joint of an examinee is fixed to the subject table (i.e., with a fingertip pulled), as a result of intensive studies.

SUMMARY OF THE INVENTION

In view of such circumstances, an object of the present invention is to provide an imaging apparatus that includes a subject table that can firmly hold a subject during radiography with a reduced burden on a patient without a positional deviation and blurring, and can produce a clear joint image.

According to an aspect of the present invention, there is provided a joint imaging apparatus including: a subject table to hold a finger of a person as a subject in a radiographic position; and a radiographic unit including: a radiation generating section disposed above the subject table to irradiate a joint of the finger, and a detecting section disposed under the subject table to detect radiation that passes through the joint, wherein the subject table includes: a base unit to fix a wrist of the person, and a first subject fixing unit to fix the joint to a first predetermined position with respect to a direction of the radiation emitted from the radiation generating section; wherein the first subject fixing unit includes: a first fixing member to fix a part on one side of the joint, the one side being closer to a trunk of the person than the other side of the joint, and a second fixing member to fix a part on the other side of the joint; and wherein a position of the second fixing member is adjustable relative to a position of the first fixing member.

Preferably, the first subject fixing unit is attachable to and detachable from the base unit.

Preferably, the joint imaging apparatus further includes a second subject fixing unit to fix the joint to a second predetermined position different from the first predetermined position, wherein each of the first and second subject fixing units is attachable to and detachable from the base unit.

Preferably, the apparatus is a fringe scanning imaging apparatus including a first grating and a second grating each extending in a direction orthogonal to the direction of the radiation emitted from the radiation generating section and each having a plurality of slits provided at predetermined intervals.

Preferably, the joint imaging apparatus further includes a multi-slit grating disposed adjacent to the radiation generating section, wherein the first grating, the second grating, and the multi-slit grating constitute a Talbot-Lau interferometer where the multi-slit grating is movable relative to the first grating and the second grating.

BRIEF DESCRIPTION OF THE DRAWINGS

The above and other objects, advantages and features of the present invention will become more fully understood from the detailed description given hereinbelow and the appended drawings which are given by way of illustration only, and thus are not intended as a definition of the limits of the present invention, and wherein:

FIG. 13A is a perspective view illustrating the base unit;

FIG. 13B is a perspective view illustrating a second subject fixing unit;

FIG. 13C is a perspective view illustrating a subject holder including the second subject fixing unit mounted on the base unit;

FIG. 14A is a perspective view illustrating the subject holder provided with the second subject fixing unit to which the second finger is fixed;

FIG. 14B is a perspective view illustrating the subject holder provided with the second subject fixing unit to which the third finger is fixed;

FIG. 14C is a perspective view illustrating the subject holder provided with the second subject fixing unit to which the fourth finger is fixed;

FIG. 14D is a perspective view illustrating the subject holder provided with the second subject fixing unit to which the fifth finger is fixed;

FIG. 15A is a perspective view illustrating the base unit;

FIG. 15B is a perspective view illustrating a third subject fixing unit;

FIG. 15C is a perspective view illustrating a subject holder including the third subject fixing unit mounted on the base unit;

FIG. 17A is a perspective view illustrating the base unit;

FIG. 17B is a perspective view illustrating a fourth subject fixing unit;

FIG. 17C is a perspective view illustrating a subject holder including the fourth subject fixing unit mounted on the base unit;

FIG. 19A is a perspective view illustrating the base unit;

FIG. 19B is a perspective view illustrating a fifth subject fixing unit;

FIG. 19C is a perspective view illustrating a subject holder including the fifth subject fixing unit mounted on the base unit;

DESCRIPTION OF THE PREFERRED EMBODIMENTS

An embodiment of a joint imaging apparatus according to the present invention will now be described with reference to the accompanying drawings.

The joint imaging apparatus 1 in the present embodiment includes a radiographic unit and a subject table 13. The subject table 13 holds a subject such as a human finger on a position for radiography. The radiographic unit includes an X-ray source 11 (radiation generating section) and an X-ray detector 16 (detecting section). The X-ray source 11 is disposed above the subject table 13 to irradiate a subject, such as a joint of a finger with X-rays. The X-ray detector 16 is disposed under the subject table 13 to detect X-rays that pass through the joint.

Figure 1:
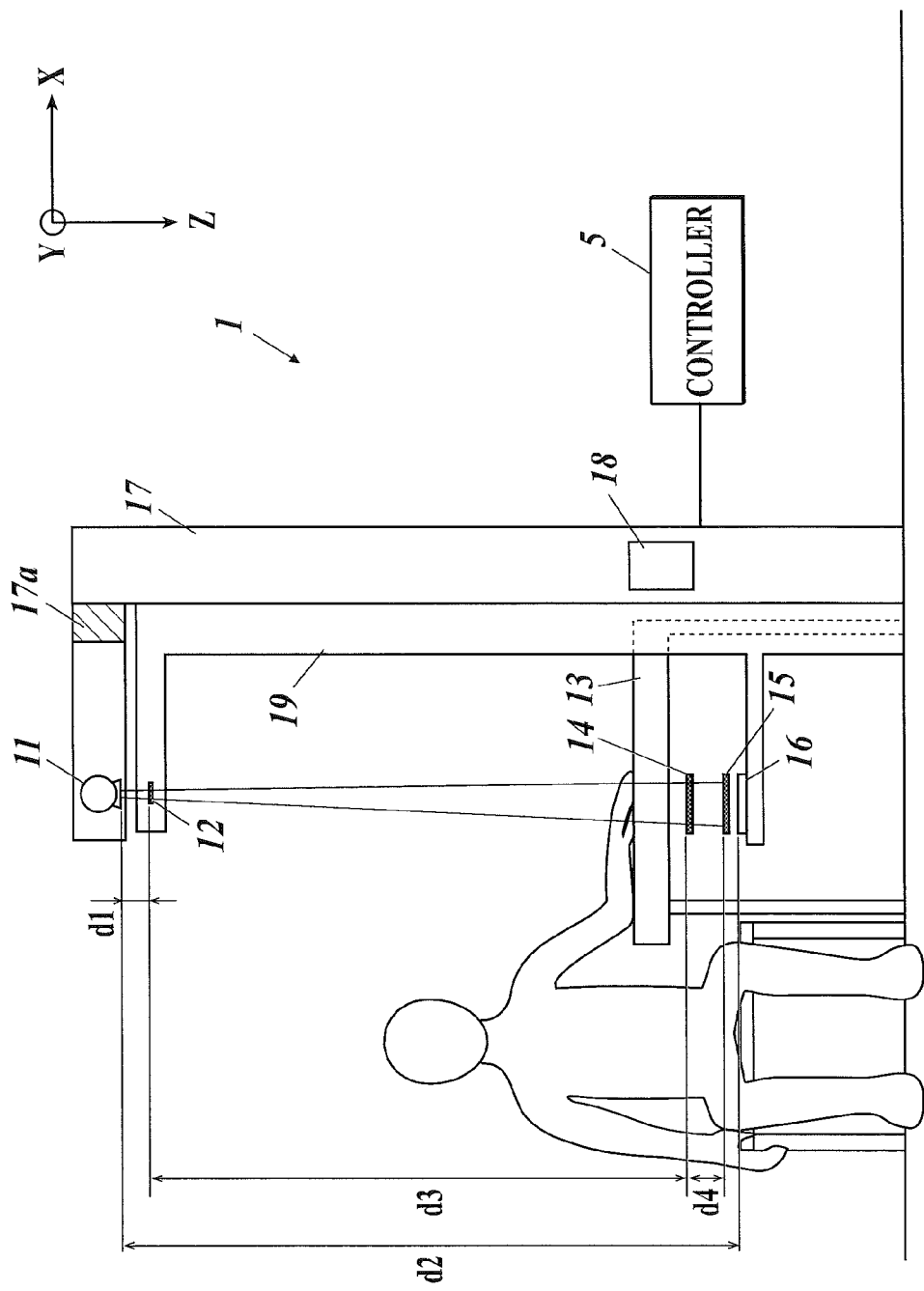
FIG. 1 is a schematic side view of an X-ray imaging system including a joint imaging apparatus according to an embodiment of the invention.
Figure 2:
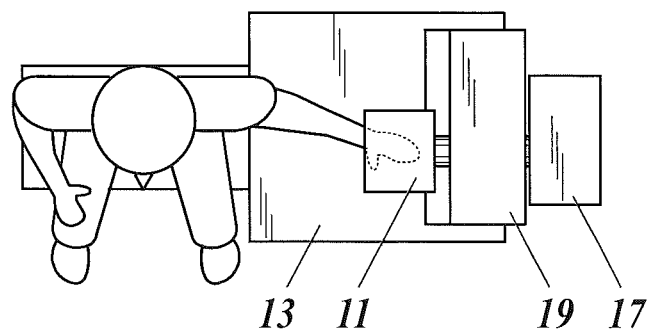
FIG. 2 is a top view of the joint imaging apparatus illustrated in FIG. 1.

FIG. 1 schematically illustrates an X-ray imaging system including the joint imaging apparatus 1 according to the present embodiment, and FIG. 2 is a top plan view illustrating the joint imaging apparatus 1 in FIG. 1.

The X-ray imaging system includes the joint imaging apparatus 1 and a controller 5. The joint imaging apparatus 1 radiographs a subject with a Talbot-Lau interferometer, and the controller 5 reconstructs an image of the subject from a moire image produced by the radiography.

The joint imaging apparatus 1 includes the X-ray source 11, a multi-slit grating 12, a light field confirming unit 6, the subject table 13, a first grating 14, a second grating 15, the X-ray detector 16, a post 17, a main body 18, and a support 19, as illustrated in FIG. 1.

Figure 29:
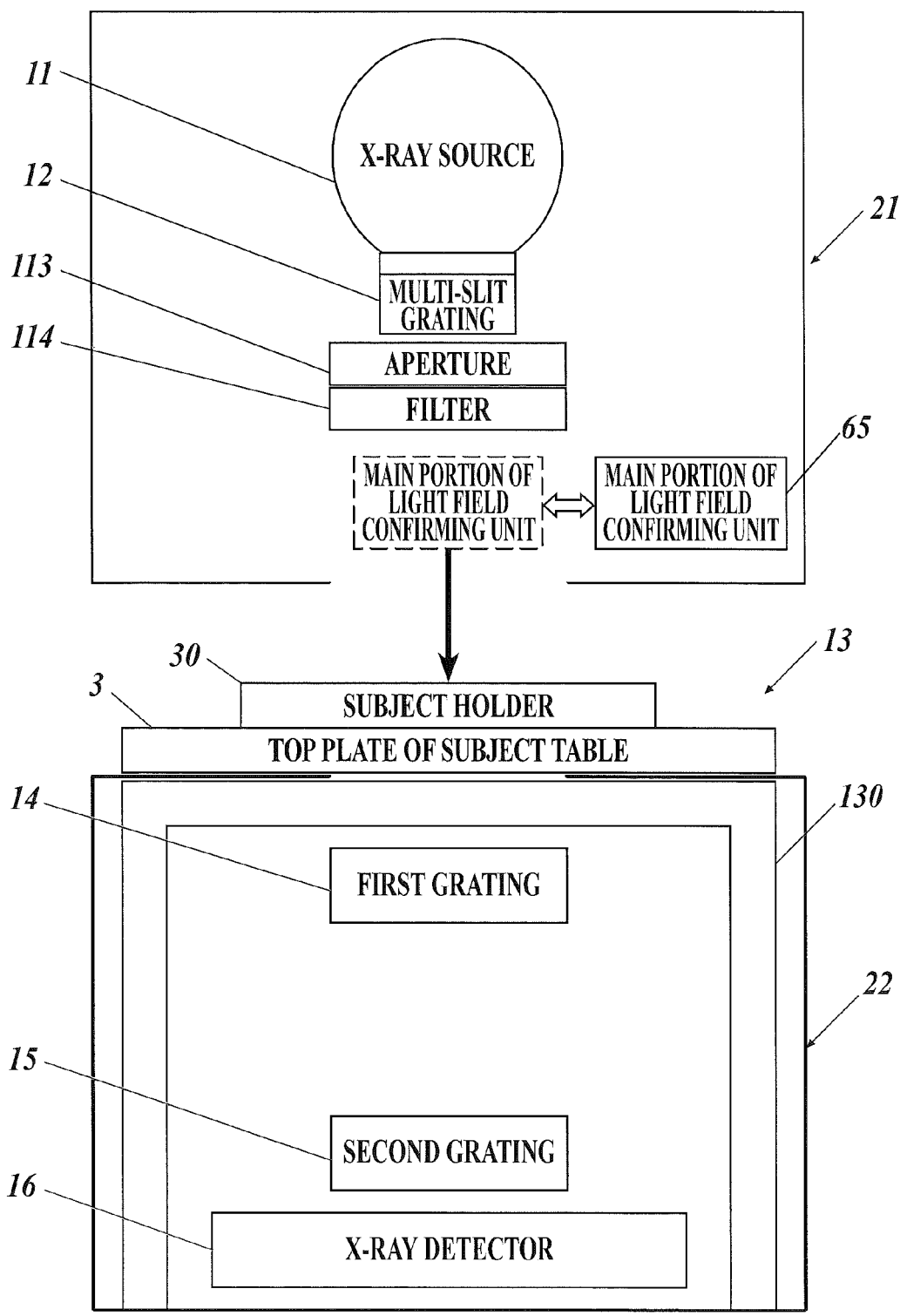
FIG. 29 schematically illustrates main part of the joint imaging apparatus illustrated in FIG. 1.

The joint imaging apparatus 1 in the present embodiment is of an upright type, and the X-ray source 11, the multi-slit grating 12, the subject table 13, the first grating 14, the second grating 15, and the X-ray detector 16 are arranged in this order along the z direction, i.e., the direction of gravitational force (see FIG. 29).

In FIG. 1, d1 (mm) denotes the distance between the focus of the X-ray source 11 and the multi-slit grating 12, d2 (mm) the distance between the focus of the X-ray source 11 and the X-ray detector 16, d3 (mm) the distance between the multi-slit grating 12 and the first grating 14, and d4 (mm) the distance between the first grating 14 and second grating 15.

The distance d1 preferably ranges from 3 to 500 (mm), and more preferably from 4 to 300 (mm).

The distance d2 is preferably not greater than 3000 (mm) since a radiographic room is generally not higher than 3 (m).

The distance d2 more preferably ranges from 400 to 2500 (mm), and even more preferably from 500 to 2000 (mm).

The distance (d1+d3) between the focus of the X-ray source 11 and the first grating 14 preferably ranges from 300 to 5000 (mm), and more preferably from 400 to 1800 (mm).

The distance (d1+d3+d4) between the focus of the X-ray source 11 and the second grating 15 preferably ranges from 400 to 5000 (mm), and more preferably from 500 to 2000 (mm).

These distances can be determined by calculating the optimum distance at which a grating image (self-image) formed with the first grating 14 is formed on the second grating 15, on the basis of the wavelength of X-rays from the X-ray source 11.

Figure 3:
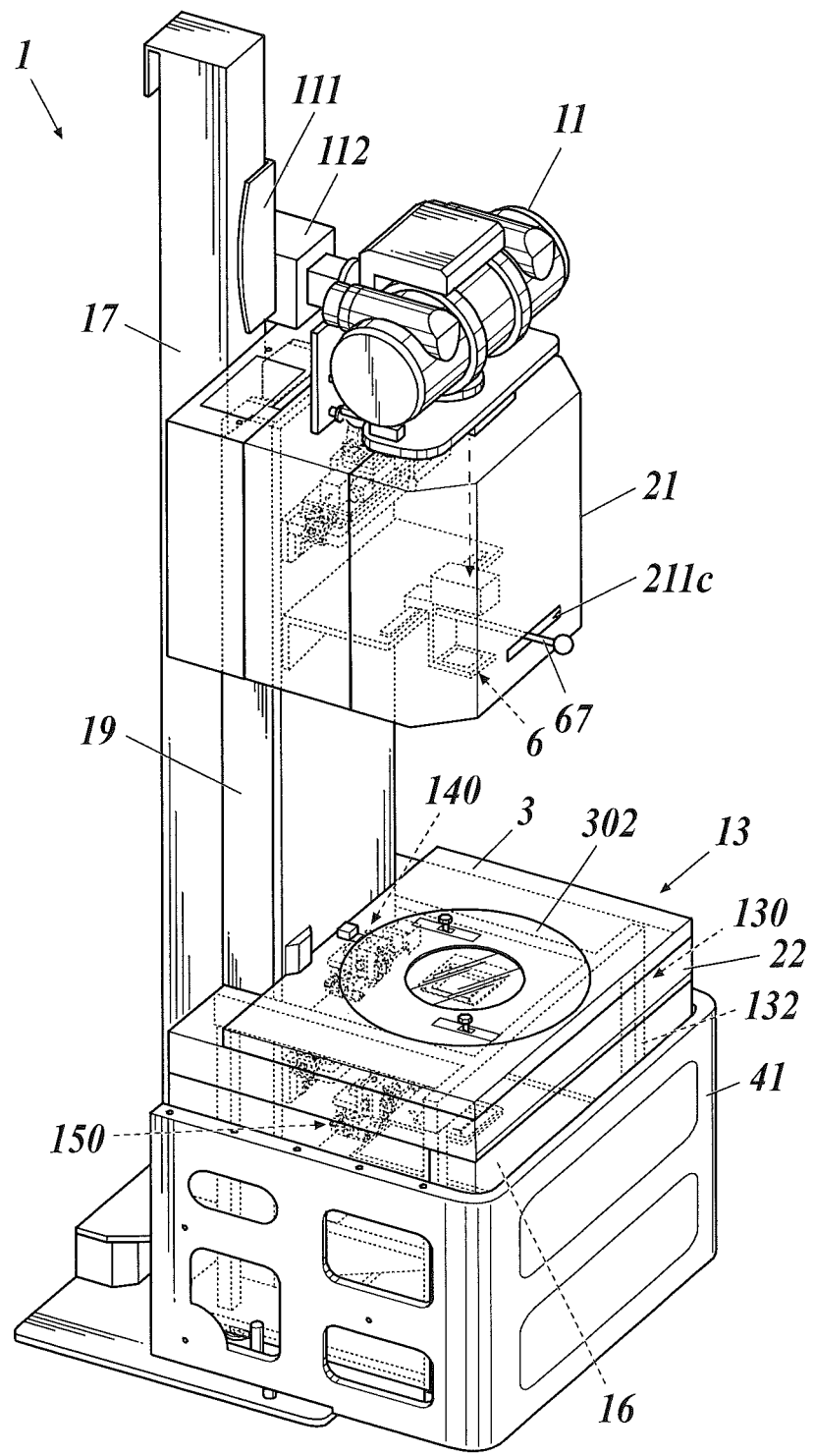
FIG. 3 is a perspective view illustrating a specific configuration of the joint imaging apparatus illustrated in FIG. 1.
Figure 4:
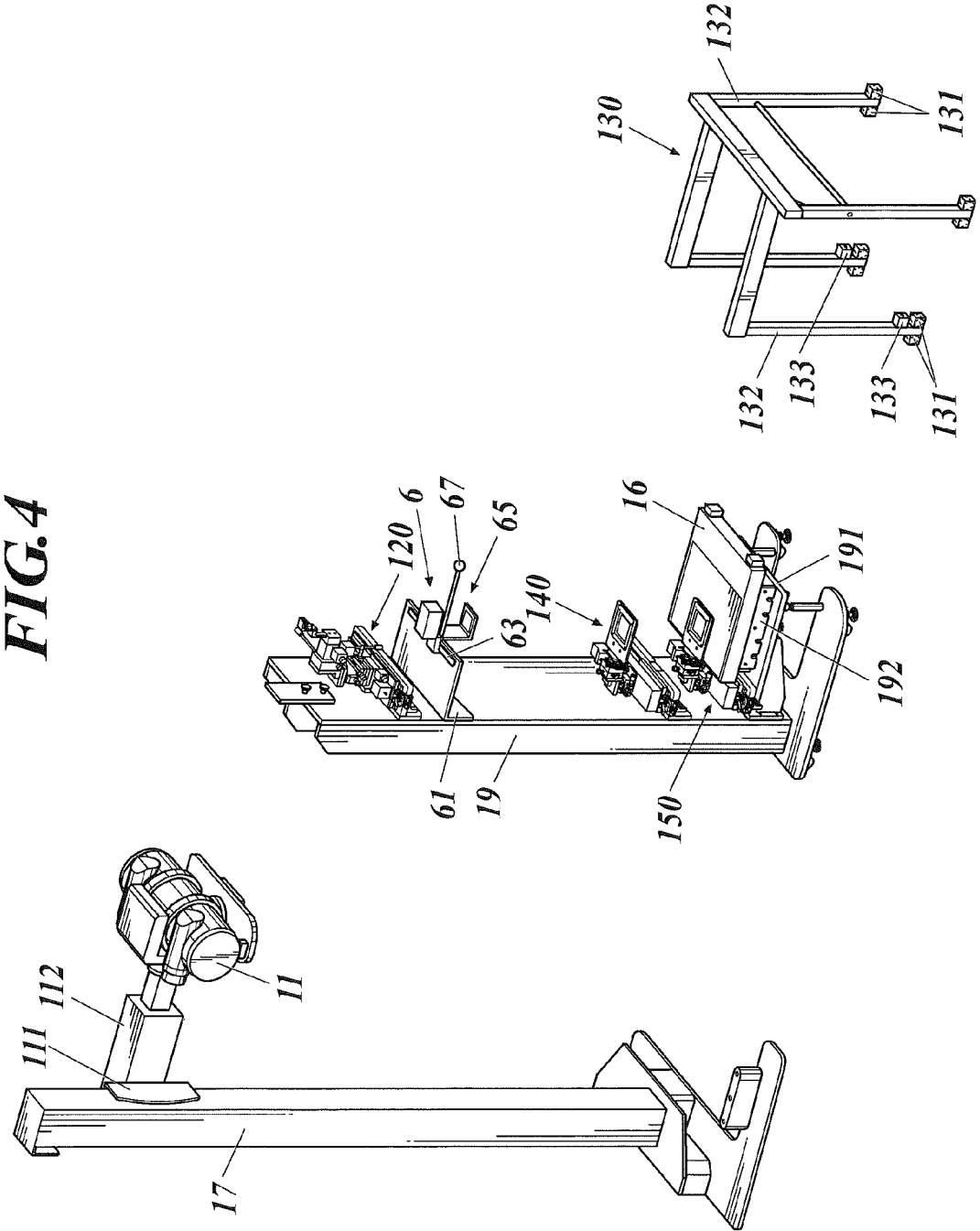
FIG. 4 is a perspective view illustrating three parts separated from one another of the joint imaging apparatus illustrated in FIG. 3.

FIG. 3 is a perspective view illustrating a specific configuration of the joint imaging apparatus 1 illustrated in FIGS. 1 and 2, and FIG. 4 is a perspective view illustrating three parts separated from one another of the joint imaging apparatus 1.

As illustrated in FIGS. 3 and 4, the joint imaging apparatus 1 of the present embodiment can be separated into the following major parts: the post 17 supporting the X-ray source 11; the support 19 provided with a multi-slit grating unit 120 including the multi-slit grating 12, a first grating unit 140 including the first grating 14, a second grating unit 150 including the second grating 15, and the X-ray detector 16; and the subject table 13 (Note that only a subject table base 130, which is part of the subject table 13, is illustrated in FIG. 4.). The radiographic unit of the present embodiment includes the post 17 supporting the X-ray source 11, and the support 19 to which the X-ray detector 16 is fixed. The separability of the radiographic unit from the subject table 13 allows the radiographic unit to be free from the influence of a shock given by a patient to the subject table 13 before or during the radiography.

A first cover unit 21 and a second cover unit 22 are installed to the support 19 in the present embodiment. The unit 21 covers the multi-slit grating unit 120 while the unit 22 covers the first and second grating units 140 and 150.

The multi-slit grating 12, the first grating 14, and the second grating 15 need highly accurate positioning as described later, and thus desirably the same condition is maintained during a series of radiographic exposures, such as radiography of a subject and radiography for calibration without the subject.

Nevertheless, the gratings 12, 14, and 15 without any cover in the atmosphere tend to be influenced by shocks, vibrations, and temperature change in the atmosphere of the radiographic room (for example, a temperature difference between the ceiling and the floor, due to variable air flow caused by air-conditioning); as a result, the positions and orientations of the gratings 12, 14, and 15 may be gradually shifted from the best ones during a series of radiographic exposures. The first and second cover units 21 and 22 prevent the gratings 12, 14 and 15 from being influenced by external factors and maintain the radiographic conditions during a series of exposures. For example, the units 21 and 22 prevent partial variations caused by thermal expansion due to direct exposure to cool or warm air from an air conditioner and also prevent shocks to the gratings 12, 14, and 15, which are precise instruments, from the outside.

Figure 5:
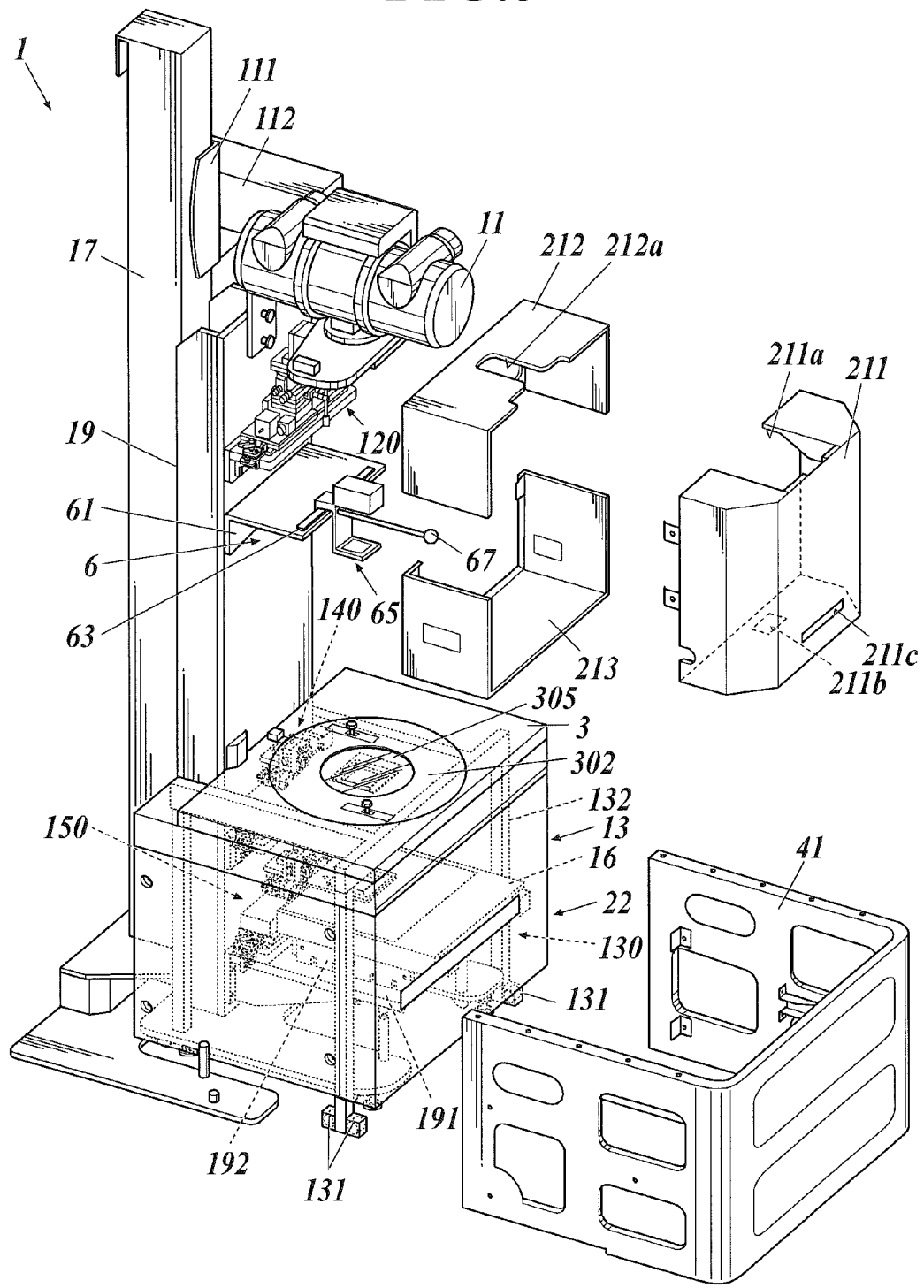
FIG. 5 is a perspective view illustrating the joint imaging apparatus illustrated in FIG. 3, from which a first cover unit is disassembled.

FIG. 5 is a perspective view illustrating the joint imaging apparatus 1, from which the first cover unit 21 to cover the multi-slit grating unit 120 and the light field confirming unit 6 is disassembled.

As illustrated in FIG. 5, the first cover unit 21 includes a front cover 211 that covers the front of the multi-slit grating unit 120 and the light field confirming unit 6, an upper cover 212 that is behind the front cover 211 (i.e., adjacent to the post 17) of the joint imaging apparatus 1 and covers the top of the multi-slit grating unit 120, and a lower cover 213 that is under the multi-slit grating unit 120 and the light field confirming unit 6 and pairs off with the upper cover 212. The covers 211, 212, and 213 forming the first cover unit 21 are made by pressing metal plates, for example.

Cutouts 211a and 212a are provided in the top surfaces of the front and upper covers 211 and 212, respectively, facing the X-ray source 11. An opening 211b is provided in the bottom surface of the front cover 211, facing an irradiation hole of the X-ray source 11. Accordingly, the installed first cover unit 21 does not block X-rays from the X-ray source 11.

An opening 211c for a lever 67, described later, of the light field confirming unit 6 extends in a face, opposed to the post 17, of the front cover 211. The opening 211c is a slit extending in the x direction with its width corresponding to the range of motion of the lever 67, and the distal end of the lever 67 protrudes from the opening 211c of the front cover 211. Accordingly, a user can operate the lever 67 of the light field confirming unit 6 covered by the first cover unit 21. A mark or an index may also be provided near the opening 211c to indicate which of a light field confirmation position and a retraction position (described later) a main portion 65 of the light field confirming unit is positioned, depending on a position of the lever 67.

In the installation of the first cover unit 21, the upper cover 212 is screwed onto the support 19 so as to cover the top of the multi-slit grating unit 120, and the lower cover 213 is brought into contact with the lower end of the upper cover 212 in alignment from under the multi-slit grating unit 120 and is screwed onto the support 19. The front cover 211 is then fit to the upper and lower covers 212 and 213 from the front of the multi-slit grating unit 120 and is screwed onto each of them.

Note that the first cover unit 21 may be composed of any material, may have any shape and configuration as long as the unit 21 can block external influences on the multi-slit grating unit 120, and may be fixed by any means. Furthermore, a heat insulator is preferably provided at least in the first cover unit 21.

Figure 6:
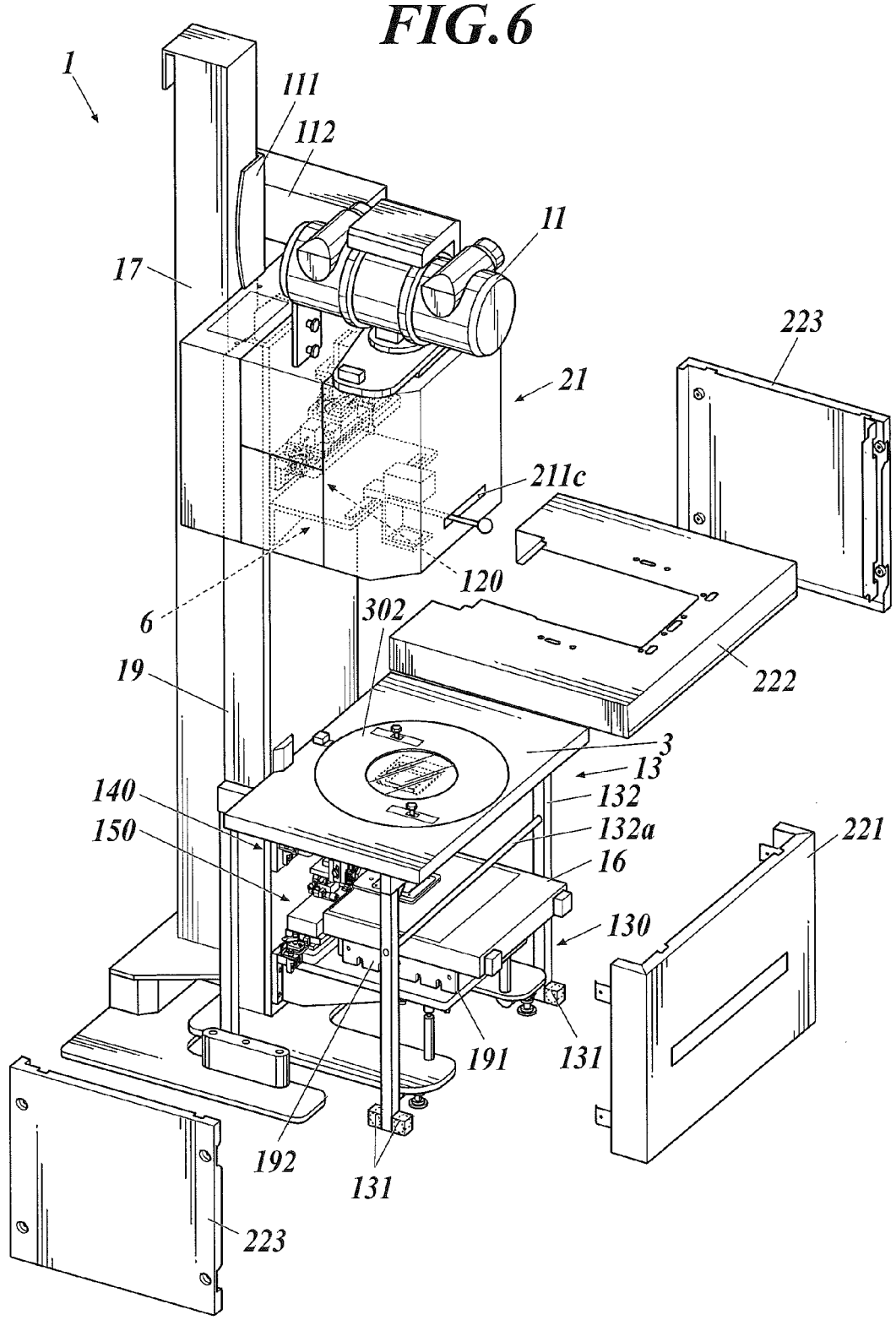
FIG. 6 is a perspective view illustrating the joint imaging apparatus illustrated in FIG. 3, from which a second cover unit is disassembled.

FIG. 6 is a perspective view illustrating the joint imaging apparatus 1, from which the second cover unit 22 covering the first and second grating units 140 and 150 is disassembled.

As illustrated in FIG. 6, the second cover unit 22 includes a front cover 221 that covers the front of the first and second grating units 140 and 150, an upper cover 222 that covers the top of the first grating unit 140, and side covers 223 that cover both the sides of the first and second grating units 140 and 150. The covers 221, 222, and 223 defining the second cover unit 22 are formed by pressing metal plates, for example.

The upper cover 222 is a U-shaped member viewed from above, the central area of which is cut out so as not to cover a subject to be placed on the subject table 13, and the first and second gratings 14 and 15.

In the installation of the second cover unit 22, each of the side covers 223 is fixed to the support 19 so as to cover both the sides of the first and second grating units 140 and 150, and the front cover 221 is screwed onto the front flange of each side cover 223 in alignment so as to cover the front of the first and second grating units 140 and 150. The upper cover 222 is then put on from above and is screwed onto each of the support 19, the side covers 223, and the front cover 221.

Note that the second cover unit 22 may be composed of any material, may have any shape and configuration as long as the unit 22 can block external influences on the first and second grating units 140 and 150, and may be fixed by any means. Furthermore, a heat insulator is preferably provided at least in the second cover unit 22.

The second cover unit 22 is readily subjected to external shocks such as a hit by a foot of the patient whose hand, i.e., a subject, is placed on the subject table 13. For this reason, a guard 41 is provided outside the second cover unit 22, as illustrated in FIGS. 3 and 5. For example, the guard 41 is made of a metal plate and is detachably fixed to the second cover unit 22 by screws, as illustrated in FIG. 5. Note that the guard 41 may have any shape and may be fixed to the second cover unit 22 by any method. Furthermore, an elastic member for impact absorption may also be provided in the guard 41.

The guard 41 can prevent the shock by a foot of a patient on the apparatus during the radiography from propagating to the precise instruments such as the first and second gratings 14 and 15, thereby leading to highly accurate imaging.

The subject table 13 is a table on which fingers of a patient, i.e., a subject, are placed during radiography. The subject table 13 may have any size, and is preferably long enough and has an arm rest to support a lower arm of the patient placed thereon when the subject, the fingers of the patient, is placed within an area irradiated with X-rays (i.e., within an area that can be radiographed) during radiography, as illustrated in FIG. 1. Placing the fingers and lower arm on the subject table 13 can stabilize the position and posture of the fingers, which are a radiographic subject, leading to the prevention of body movements such as a slight tremor in the hand during radiography.

As illustrated in FIGS. 3 and 4, the subject table 13 of the present embodiment includes the subject table base 130, which has legs 132 with casters 131 and is independent of the post 17 and the support 19. The post 17 and the support 19 are disposed between the two legs 132 closer to the support 19, which are provided with locking mechanisms 133 to lock the casters 131.

Note that the subject table 13 may have another configuration. For example, all of the legs 132 of the subject table base 130 may also be provided with the locking mechanisms 133, or the subject table 13 may also be fixed to an end of the post 17 or the support 19 without any locking mechanism 133. The subject table 13 preferably includes a shock absorber (not shown) that can absorb the impact occurring when the table comes into contact with the post 17 or the support 19.

In the present embodiment, a fixing beam 132a to which an X-ray detector holder 25 is detachably fixed is provided horizontally across the front legs 132 of the subject table base 130.

Figure 7:
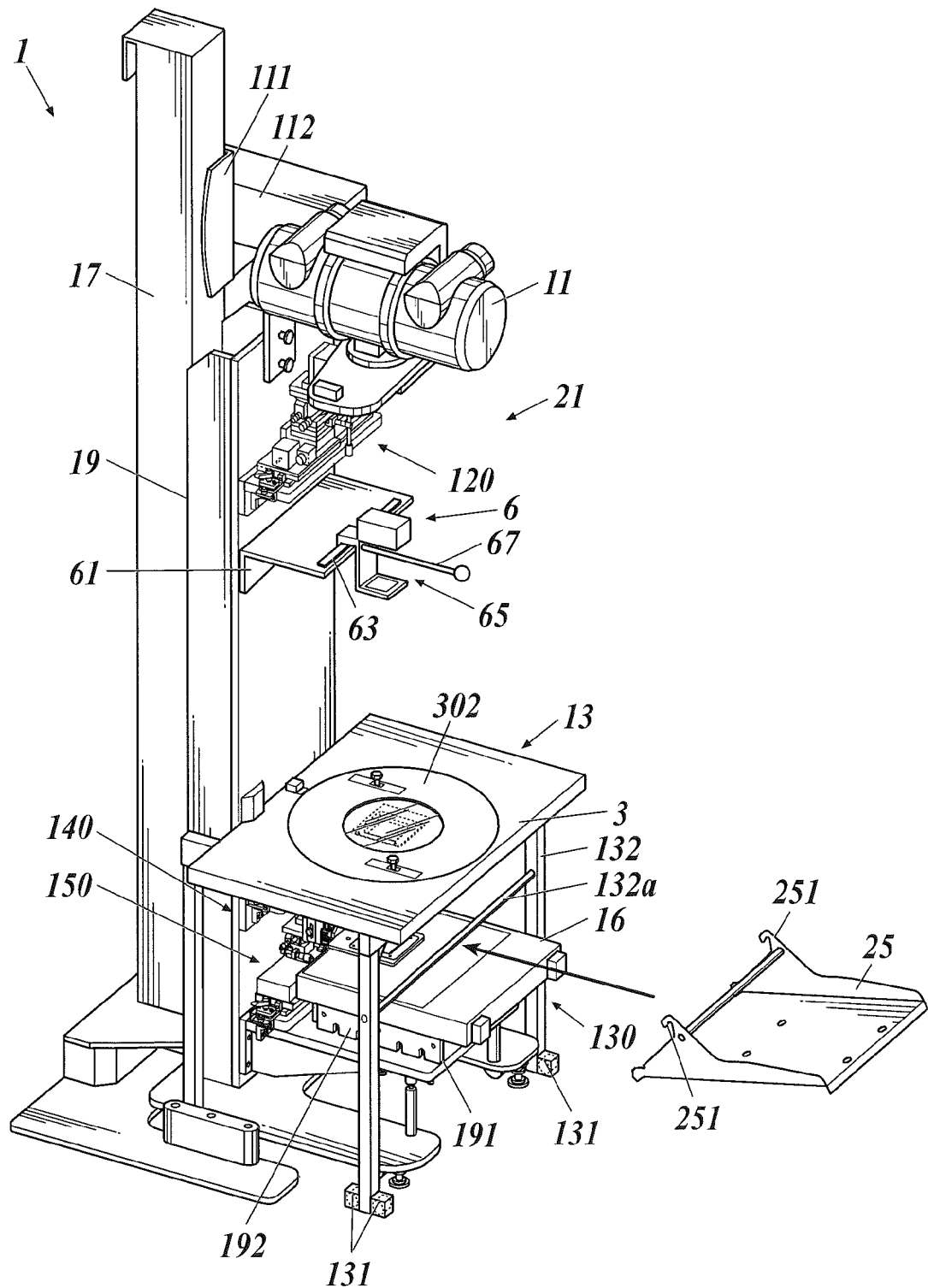
FIG. 7 is a perspective view illustrating the installation of an X-ray detector holder to the joint imaging apparatus illustrated in FIG. 4.
Figure 8:
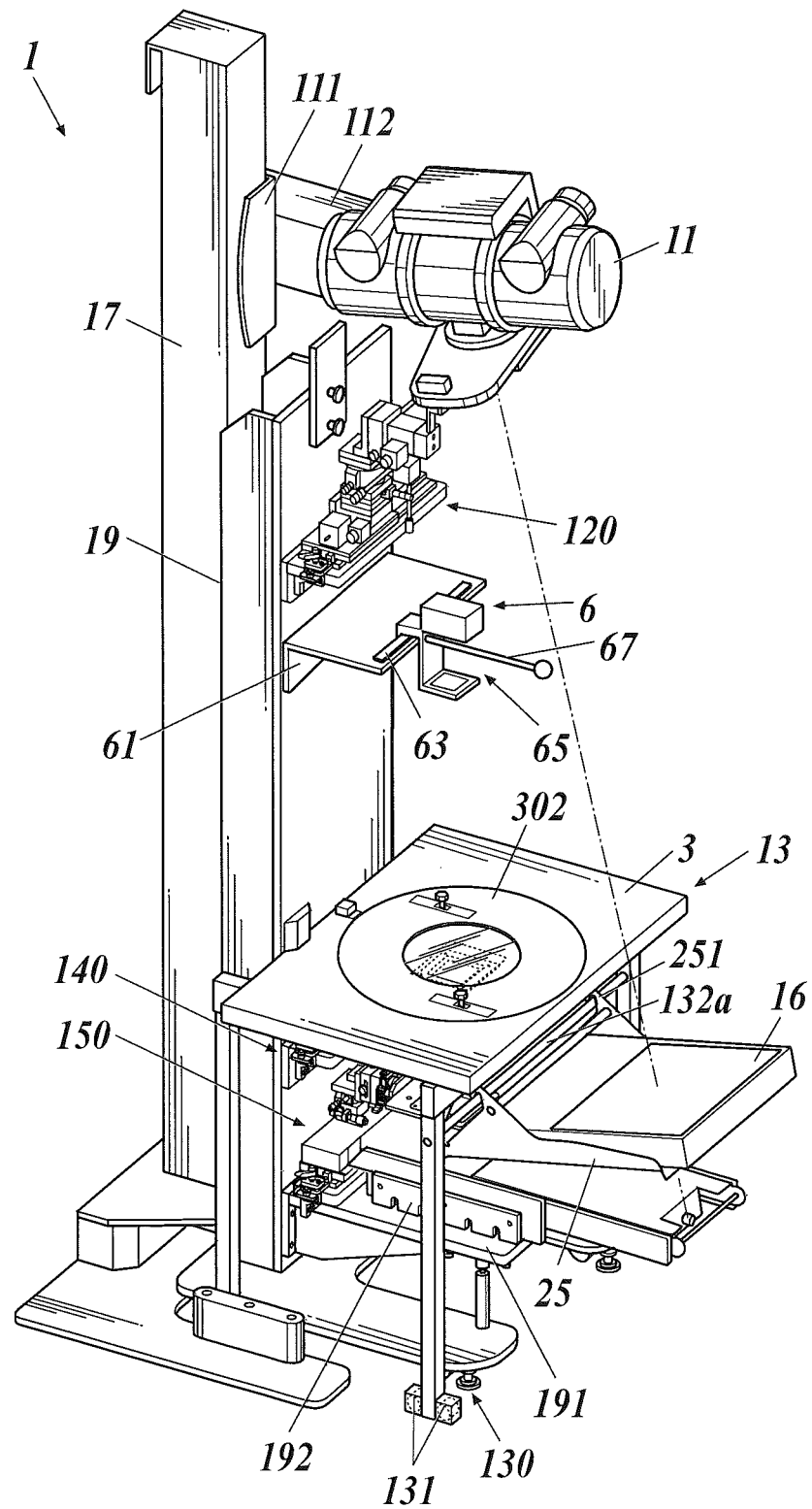
FIG. 8 is a perspective view illustrating the joint imaging apparatus in FIG. 4 after the installation of the X-ray detector holder.

The X-ray detector holder 25 holds the X-ray detector 16 during the calibration of gain of the X-ray detector 16. Unciform locking hooks 251 are formed at one end of the X-ray detector holder 25, as illustrated in FIGS. 7 and 8. The X-ray detector holder 25 having the X-ray detector 16 held thereon is fixed to the subject table 13 by holding the locking hooks 251 on the fixing beam 132a of the subject table 13, during the calibration of the X-ray detector 16.

According to the present embodiment, the direction of X-rays emitted from the X-ray source 11 is variable as described later. The orientation of the X-ray source 11 is adjusted such that the optical axis of an X-ray deviates from the multi-slit grating 12 and the first and second gratings 14 and 15 (i.e., the calibration mode, see FIG. 8) for the calibration of the X-ray detector 16. The X-ray detector holder 25 fit to the subject table 13 is placed on the extension of the optical axis of the X-ray source 11 after the direction of X-rays emitted from the X-ray source 11 is adjusted to that in the calibration mode. X-rays are emitted from the X-ray source 11 for radiography with the X-ray detector 16 held on the X-ray detector holder 25. This creates a calibration radiograph having no images of the multi-slit grating 12, and the first and second gratings 14 and 15.

A top plate 3 of the subject table 13 for holding a subject is pinned to the upper cover 222 of the second cover unit 22 using fixing pins (not shown). The top plate 3 is made of resin or metal. The upper cover 222 has through holes at positions of the fixing pins on the top plate 3. The top plate 3 is fixed to the subject table base 130 from above the upper cover 222 after the second cover unit 22 is fit to the support 19.

The top plate 3 can preferably adjust the height at which a subject is held, for example, by vertically shifting the fixing position of the fixing pins in multiple stages. Adjusting the fixing position of the fixing pins on the top plate 3 in this manner can allow a distance between the subject held on the subject table 13 and the X-ray source 11 to be a predetermined one suitable for radiography.

A circular cutout 301 is formed at the substantial center of the top plate 3, and a rotation disk 302 is rotatably fit to the cutout 301. Rotating the rotation disk 302 can readily vary and modify the orientation and position of a subject holder 30 (see FIGS. 11A-11C) placed on the rotation disk 302. This facilitates the adjustment of positioning.

The orientation and angle of slits of the multi-slit grating 12, the first grating (first phase grating) 14, and the second grating (second phase grating) 15 as well as the orientation and angle of a subject must be properly adjusted to create a moire image having interference fringes, for the radiography of a joint by fringe scanning as is the case with the joint imaging apparatus 1 of the present embodiment. Since the multi-slit grating 12, and the first and second gratings 14 and 15 are highly precise, the movement and adjustment of these gratings may compromise the accuracy. In this regard, since the subject-placed area of the top plate 3 is rotatable, the orientation and position mentioned above can be adjusted as needed by moving the subject. Note that excess rotation of the rotation disk 302 causes a failure in creating a moire image. For this reason, the rotation angle of the rotation disk 302 may also be within a certain range, for example, from a predetermined initial position to 45 degrees.

A pin 303 for fixing the rotation disk 302 is provided at a particular position that is on the top plate 3 and near the peripheral edge of the rotation disk 302, and the rotation disk 302 can be fixed with the pin.

A substantially circular cutout 304 for a passage of X-rays from the X-ray source 11 is provided at the substantial center of the rotation disk 302, at the position corresponding to the first and second gratings 14 and 15.

Figure 9:
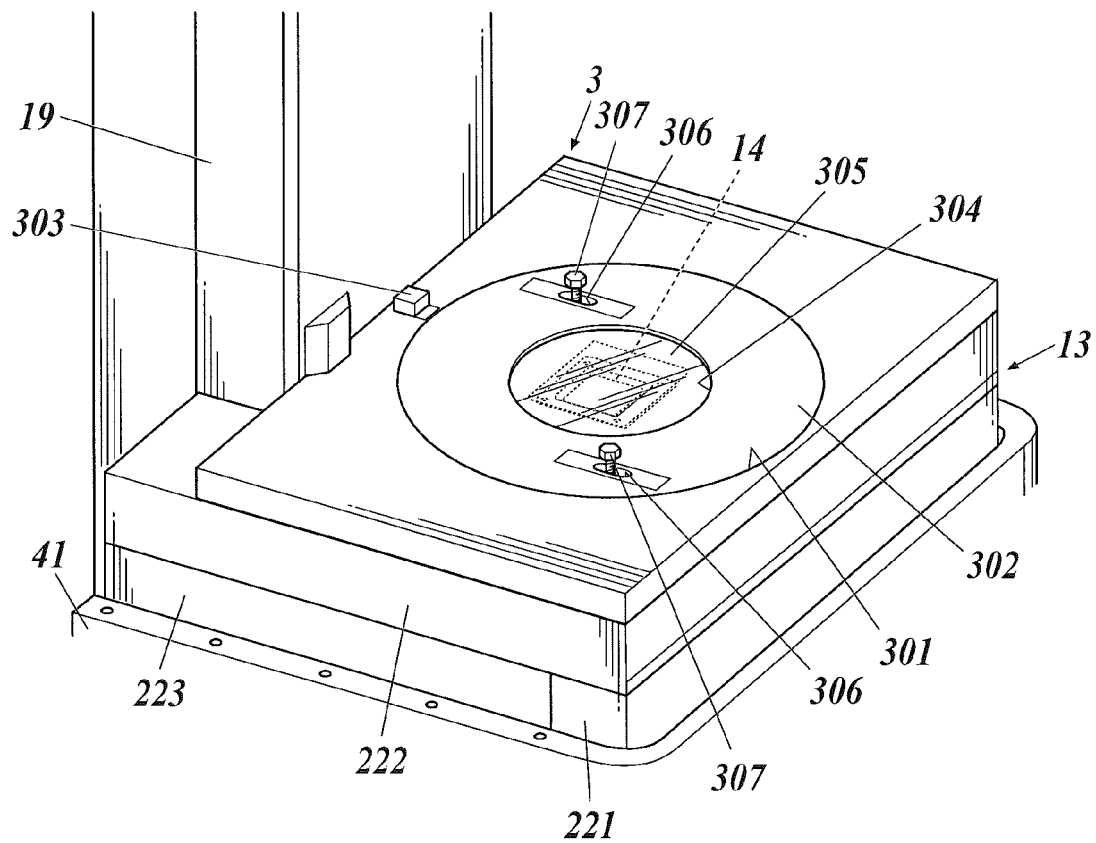
FIG. 9 is an enlarged perspective view illustrating the essential portion of a top plate of a subject table.
Figure 10:
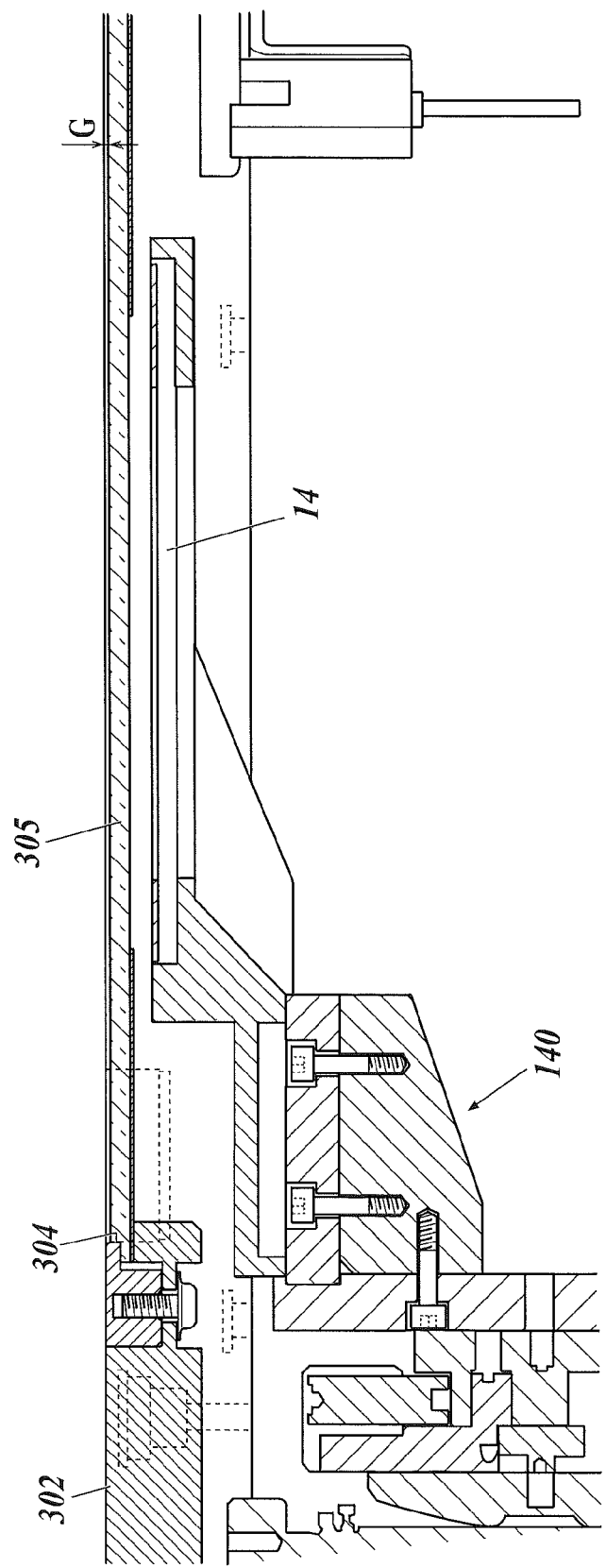
FIG. 10 is an enlarged cross-sectional view illustrating the essential portion around the center of the top plate of the subject table illustrated in FIG. 9.

A substantially circular transparent plate 305 made of transparent material such as transparent acrylic resin or glass is fit to the cutout 304, as illustrated in FIGS. 9 and 10.

The top of the transparent plate 305 is disposed slightly lower than that of the rotation disk 302, as illustrated in FIG. 10. In the present embodiment, the top of the transparent plate 305 is lower than that of the rotation disk 302 by a difference in height G shown in FIG. 10. Such a difference prevents the subject holder 30, described later, placed and fixed onto the top of the rotation disk 302 of the top plate 3 from coming into contact with the transparent plate 305. As a result, the surface of the transparent plate 305 can be free from damages such as scratches, leading to an improvement in the durability.

As illustrated in FIG. 9, long and narrow openings 306 parallel to each other are substantially symmetrically provided on the rotation disk 302 of the top plate 3 and on opposite sides of the transparent plate 305. Holder fixing pins 307 for fixing the subject holder 30 illustrated in FIG. 11C, for example, are provided in the respective openings 306.

The subject holder 30 is detachably placed on the top plate 3. A target site receives multiple exposures in the present embodiment, and the subject holder 30 holds the fingers, i.e., a subject, so that the fingers do not move during the series of exposures.

In the present embodiment, the subject holder 30 includes a base unit 31 and a subject fixing unit 33 (a first subject fixing unit 33a to a sixth subject fixing unit 33f) that is attachable to and detachable from the base unit 31 and supports fingers, namely, a subject, as illustrated in FIGS. 11A to 11C and 13 to 28. Although only the subject holder 30 for the left hand is illustrated hereinafter, a similar subject holder 30 for the right hand is used for radiography of fingers of the right hand.

The base unit 31 and the subject fixing unit 33 are made of polyacetal resin (POM: polyoxymethylene), for example. Note that the base unit 31 and the subject fixing unit 33 may also be made of any resin other than the polyacetal resin. Parts of the units 31 and 33 that are not covered by joints of subject fingers placed when the subject holder 30 holds the subject may be made of metal. A cushion made of elastic material such as silicone resin is preferably disposed on the part with which the fingers directly come into contact. Furthermore, the base unit 31 and the subject fixing unit 33 are preferably disinfected for sanitary reason each time a patient to be radiographed is replaced; accordingly, the materials of the base unit 31 and the subject fixing unit 33 are preferably resistant to alcohol used for disinfectant treatment.

The substantial center of the base unit 31 has a framed space 311 to which the subject fixing unit 33 (the first subject fixing unit 33a to the sixth subject fixing unit 33f) is to be fit. The framed space 311 allows the subject fixing unit 33 to be held and removed.

Long and narrow openings 312 extending in the direction substantially orthogonal to the longitudinal direction of the respective openings 306 reside at positions in the base unit 31 corresponding to the two holder fixing pins 307 on the rotation disk 302 of the top plate 3.

Figure 12:
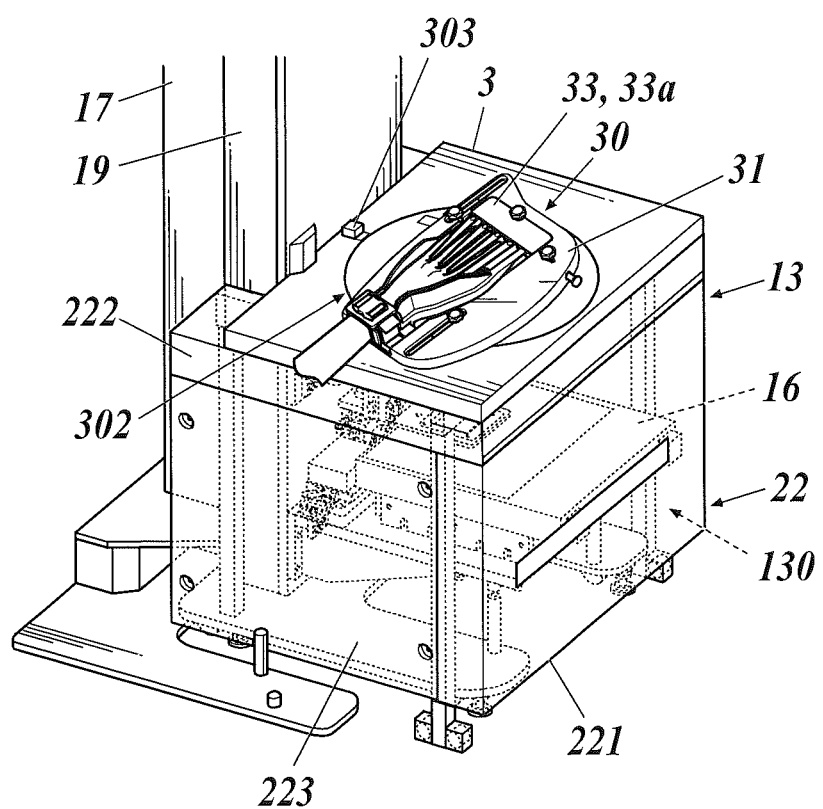
FIG. 12 is a perspective view illustrating the subject holder provided with the first subject fixing unit and placed on the top plate of the subject table.
Figure 16:
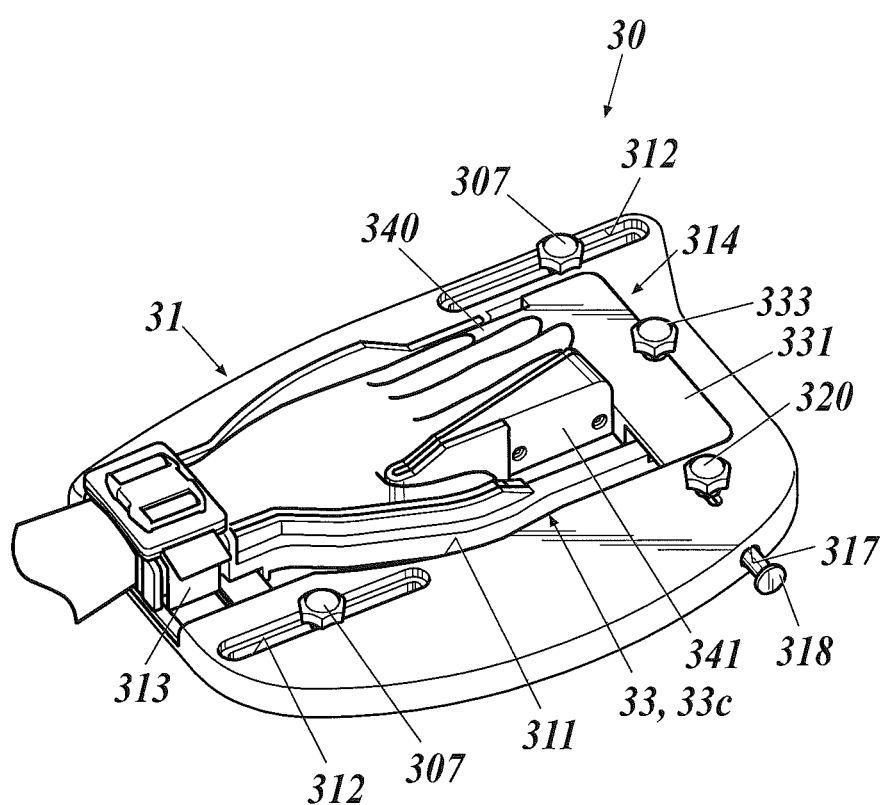
FIG. 16 is a perspective view illustrating the subject holder provided with the third subject fixing unit to which fingers are fixed.

As illustrated in FIG. 12, the holder fixing pins 307 extend through the openings 312 of the base unit 31 and the openings 306 of the rotation disk 302 to lock the subject holder 30 to the rotation disk 302 of the top plate 3. The subject holder 30 is fixed with the holder fixing pins 307 after the fine adjustment of the orientation and position of the subject holder 30 on the top plate 3 by adjusting the positions of the openings 306 and 312.

A wrist fixing belt 313 for fixing the wrist of the patient is provided at a position close to one end of the framed space 311, i.e., at a position corresponding to the wrist of the hand supported by the subject fixing unit 33.

A base fixing portion 314 for fixing the subject fixing unit 33 to the framed space 311 lies near the other end of the framed space 311, i.e., at a position corresponding to the fingertips of the hand supported by the subject fixing unit 33. A hole 316 is provided in the fixing portion 314. A fixing pin 333 is inserted through the hole 316 after the installation of the subject fixing unit 33 to the framed space 311.

A through hole 317 is provided at a position close to the fixing portion 314 of the base unit 31 and corresponding to a hole 334 in a side of a fixing portion of the subject fixing unit 33 described later (fixing portion 331). The through hole 317 horizontally extends from a side of the base unit 31 into the framed space 311 (i.e., in the horizontal direction of the subject holder 30 placed on the top plate 3). A fine-adjusting screw 318 is inserted through the through hole 317 from the side of the base unit 31 to the framed space 311.

Furthermore, a vertical hole 319 is provided in the surface of the base unit 31 toward the through hole 317. A fixation screw 320 for fixing the fine-adjusting screw 318 is inserted through the hole 319, from the surface of the base unit 31 to the through hole 317.

Note that the illustrated shape and configuration of the base unit 31 and the method of fixing the base unit 31 to the top plate 3 may be modified as appropriate.

The subject fixing unit 33 fixes joints of fingers as a radiographic subject to a predetermined position with respect to the direction of the X-rays (radiation) emitted from the X-ray source 11 (radiation generating section).

In the present embodiment, the six subject fixing units 33a to 33f are prepared as the subject fixing unit 33 that can be installed in the base unit 31, as illustrated in FIGS. 11A to 11C and 13 to 28. Note that all the subject fixing units 33a to 33f may be hereinafter simply referred to as the subject fixing units 33.

Before a radiographic operation, one of the subject fixing units 33 suitable for the radiography is selected depending on the part to be radiographed (the left hand or the right hand) and the deformation of the joints of fingers of the patient (metacarpophalangeal joints, proximal interphalangeal joints, and distal interphalangeal joints) and is installed to the base unit 31. Note that any subject fixing unit other than the illustrated subject fixing units 33 may be installed to the base unit 31. Further subject fixing units may also be prepared, or the subject fixing unit 33 may include only some of the illustrated units.

Alternatively, a particular subject fixing unit may be undetachably fixed to the base unit.

Figure 11C:
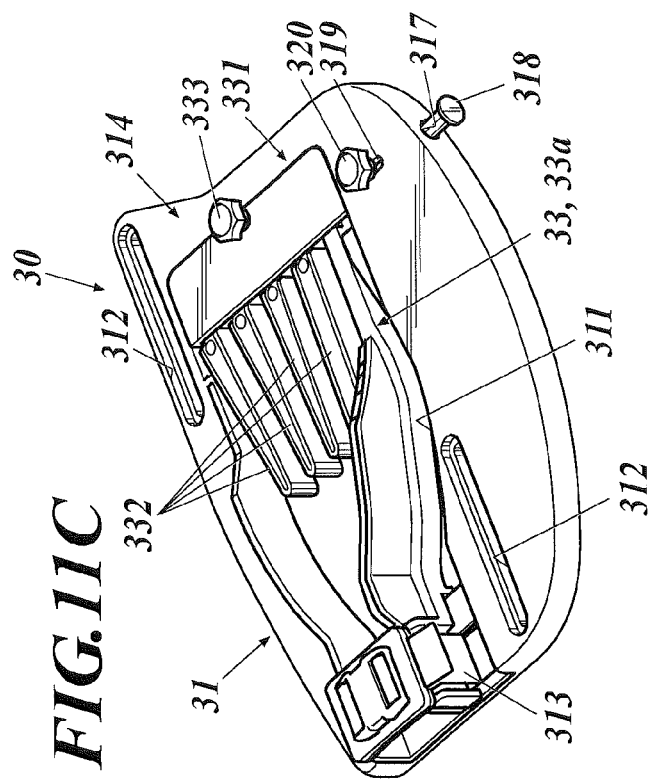
FIG. 11C is a perspective view illustrating a subject holder including the first subject fixing unit mounted on the base unit.
Figure 11A:
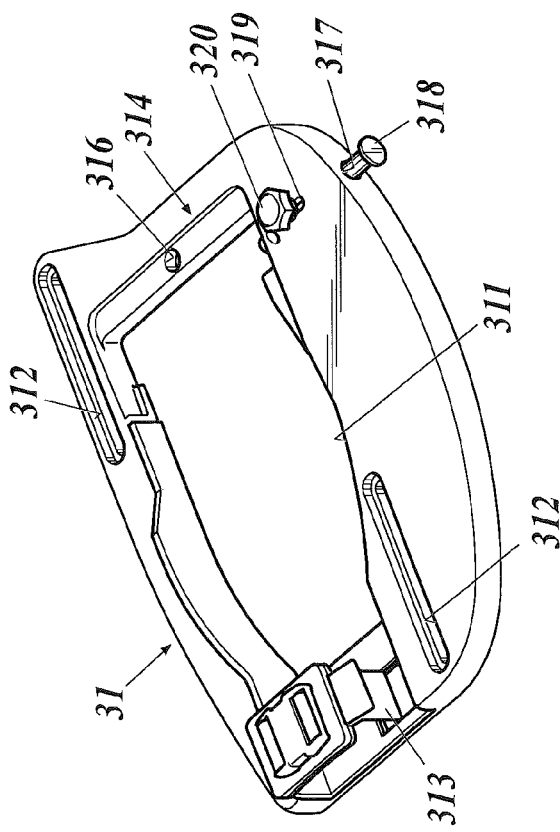
FIG. 11A is a perspective view illustrating a base unit.
Figure 11B:
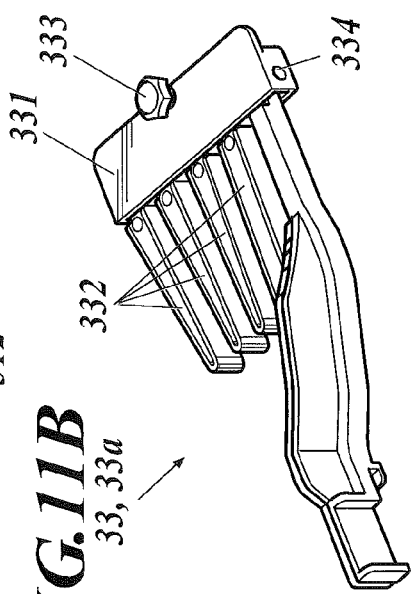
FIG. 11B is a perspective view illustrating a first subject fixing unit.

The first subject fixing unit 33a includes the fixing portion 331 for fixing the unit 33a to the base unit 31, and four finger holders 332, as illustrated in FIGS. 11A-11C.

The fixing portion 331 is provided with the fixing pin 333 at the position corresponding to the hole 316 of the base unit 31. The first subject fixing unit 33a can be tentatively fixed to the base unit 31 by inserting the fixing pin 333 from the fixing portion 331 into the hole 316 in the fixing portion 314 of the base unit 31.

The hole 334 is provided at the side of the fixing portion 331, specifically, at the position corresponding to the through hole 317 of the base unit 31. The distal end of the fine-adjusting screw 318 to pass through the through hole 317 is to be inserted into the hole 334.

The position of the first subject fixing unit 33a can be finely adjusted widthwise (i.e., in the width direction of the fingers fixed to the subject fixing unit 33) by inserting the fine-adjusting screw 318 through the through hole 317 of the base unit 31, inserting its distal end into the hole 334, and then screwing the distal end as needed. After the fine adjustment, the first subject fixing unit 33a can be fixed to the base unit 31 by fixing the fine-adjusting screw 318 from the surface of the base unit 31 using the adjustment fixation screw 320.

One end of the finger holders 332 is fixed to the fixing portion 331. The finger holders 332 are each disposed between two adjacent ones of the five fingers of the patient to fix the fingers to the subject holder 30. The finger holders 332 gradually flare from the free end to the end fixed to the fixing portion 331, so as to allow the subject fingers to be fixed with the hand spread out.

FIG. 12 illustrates the situation where the first subject fixing unit 33a fit to the base unit 31 is fixed to the top plate 3 and user fingers are fixed to the first subject fixing unit 33a. For example, if the second joint (PIP joint) of a finger is to be radiographed, the fingers are placed on the first subject fixing unit 33a such that each of the four finger holders 332 is disposed between two adjacent ones of the five fingers, as illustrated in FIG. 12, and thereby the five fingers can be supported with the hand opened.

Note that illustrated shape and configuration of the first subject fixing unit 33a and the method of fixing the first subject fixing unit 33a to the base unit 31 may be modified as appropriate. For example, the finger holders 332 may also be readily detachable from the fixing portion 331, and suitable one may be selected from different finger holders 332 having various shapes and sizes, depending on the size of a hand of a patient.

The second subject fixing unit 33b includes the fixing portion 331 for fixing the subject fixing unit 33b to the base unit 31, a grip 335 for supporting the fingers other than a radiographic subject finger, four finger holders 338 for holding each subject finger, and a supporter 336 for supporting the finger holders 338, as illustrated in FIGS. 13A to 13C and 14A to 14D.

The fixing portion 331 is the same as that of the first subject fixing unit 33a, and a redundant description thereof is omitted.

The grip 335 is a cylindrical member substantially perpendicular to the horizontal plane of the subject holder 30 fixed to the top plate 3 (i.e., the plane horizontal to the top plate 3). The grip 335 has a size and shape to be easily held by hand. Non-slip resin or cloth may be applied to the grip 335 in order to allow patients to readily hold the grip.

The supporter 336 is a substantially upright plate standing near the grip 335. The supporter 336 has four rails 337 corresponding to the respective four finger holders 338. The rails 337 extend in the longitudinal direction of the fingers fixed to the subject holder 30.

The four finger holders 338 are caps to receive the fingertips being radiographic subjects. The holders 338 are engaged in the respective four rails 337 of the supporter 336 and can slide along these rails. The finger holders 338 slide along the rails 337 to receive the fingertips and fix the fingers at the positions according to the lengths thereof.

In the present embodiment, if a joint of the first finger (index finger) is radiographed, the patient closes the other fingers around the grip 335 to stabilize the hand and stretches the first finger along the supporter 336 such that the fingertip is received by the topmost finger holder 338, as illustrated in FIG. 14A. If a joint of the second finger (middle finger) is radiographed, the patient closes the other fingers around the grip 335 to stabilize the hand and stretches the second finger along the supporter 336 such that the fingertip is received by the second finger holder 338 from the top, as illustrated in FIG. 14B. If a joint of the third finger (ring finger) is radiographed, the patient closes the other fingers around the grip 335 to stabilize the hand and stretches the third finger along the supporter 336 such that the fingertip is received by the third the finger holder 338 from the top, as illustrated in FIG. 14C. If a joint of the fourth finger (little finger) is radiographed, the patient closes the other fingers around the grip 335 to stabilize the hand and stretches the fourth finger along the supporter 336 such that the fingertip is received the bottom finger holder 338, as illustrated in FIG. 14D.

In the radiography of the second joints (PIP joints) of fingers, each stretched finger can be supported by placing each subject finger at the corresponding finger holder 338 of the second subject fixing unit 33b, with the subject holder 30 composed of the base unit 31 and the second subject fixing unit 33b thereon being fixed to the top plate 3.

Note that the illustrated shape and configuration of the second subject fixing unit 33b may be modified as appropriate. Since a finger is preferably bent back to some degree for the radiography of the second joint (PIP joint), the supporter 336 may also have a bent-back shape (that is, the supporter 336 may also be bent toward the outside of the base unit 31) and the finger holders 338 may be provided near the end thereof. Furthermore, the grip 335 is optional, and may be replaced with a partition for positioning each finger to hold each finger bent back.

The third subject fixing unit 33c includes the fixing portion 331 for fixing the third subject fixing unit 33c to the base unit 31, a step 340 for tilting up subject fingers, and a finger regulator 341 for regulating positions and angles of the fingers to expand the gap between the thumb and the other fingers, as illustrated in FIGS. 15A to 15C and 16.

The fixing portion 331 is the same as that of the first subject fixing unit 33a, and a redundant description thereof is omitted.

The step 340 is integrated with the fixing portion 331 and protrudes from one end of the fixing portion 331. For example, the step 340 is 10 to 15 mm higher than the top plate 3 on which a palm is placed, such that fingers can be tilted up by mounting the fingertips of the first to fourth fingers, i.e., radiographic subjects, on the step 340. Note that the illustrated shape and height of the step 340 may be modified. For example, the step 340 may be higher than the fixing portion 331 to further tilt up fingers. The step 340 may also have an upward slope toward the fingertips.

One end of the finger regulator 341 is fixed to the fixing portion 331. The finger regulator 341 is positioned between the thumb and the first finger of the subject fingers fixed to the subject holder 30. The finger regulator 341 flares from its free end toward the opposite end fixed to the fixing portion 331. The finger regulator 341 keeps the thumb apart from the other fingers (the first to fourth fingers) so as to expand the gap therebetween. The finger regulator 341 may have any shape and size, and the end adjacent to the fixing portion 331 of the finger regulator 341 preferably spreads such that the angle between the thumb and the other fingers is about 90 degrees. Suitable one may be selected from different finger regulators 341 having various shapes and sizes, depending on sizes of hands, shapes of fingers, and parts to be radiographed.

In this manner, when the subject holder 30 with third subject fixing unit 33c on the base unit 31 is fixed to the top plate 3 and subject fingers are fixed to the subject holder 30, the first to fourth fingers, i.e., radiographic subjects, are tilted up by the step 340 and kept apart from the thumb by the finger regulator 341, according to the present embodiment. As a result, the thumb laid on the unit can be fixed with a wide gap between the thumb and the other fingers, in the radiography of the joint of the base of the thumb, for example.

Note that the shape and configuration of the third subject fixing unit 33c may be modified appropriately.

The fourth subject fixing unit 33d includes the fixing portion 331 for fixing the fourth subject fixing unit 33d to the base unit 31, four finger holders 345 for holding each finger being a subject, and guides 343 for guiding the finger holders 345 in the longitudinal direction of the fingers, as illustrated in FIGS. 17A to 17C and 18.

The fixing portion 331 is the same as that of the first subject fixing unit 33a, and a redundant description thereof is omitted.

One end of each guide 343 is fixed to the fixing portion 331, and the finger holders 345 are attached to the respective guides 343. The finger holders 345 are slidable along the longitudinal direction of the fingers.

The portion at which a finger is to be placed of each finger holder 345 is tilted up toward the tip. As a result, the fingers whose tips are received in the finger holders 345 are bent back by the slope and fixed with the tips held at a higher position.

Figure 18:
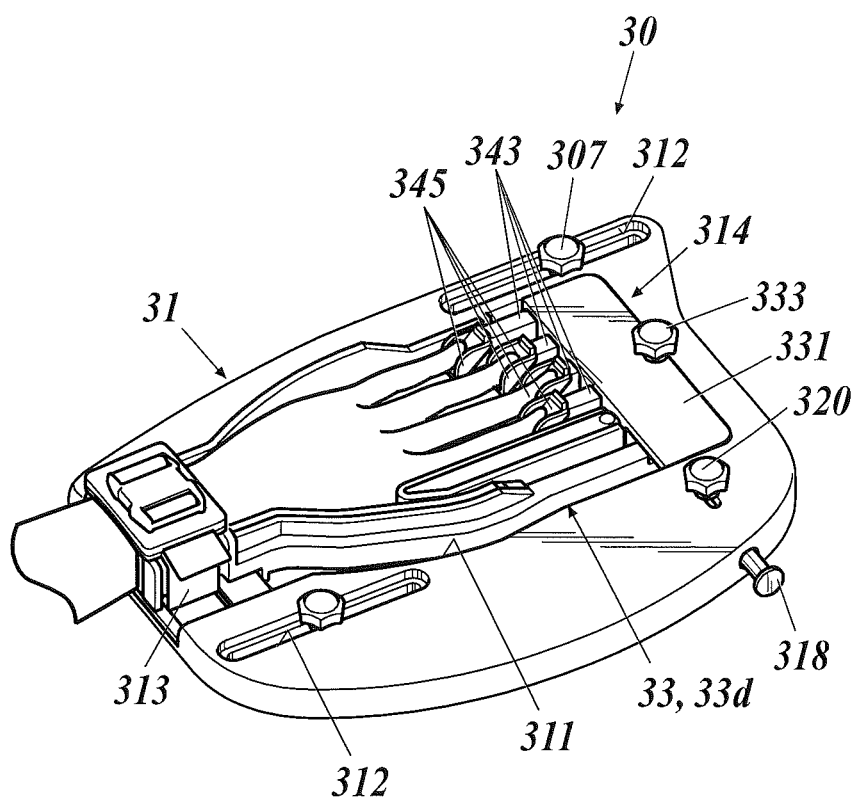
FIG. 18 is a perspective view illustrating the subject holder provided with the fourth subject fixing unit to which fingers are fixed.

The finger holders 345 slide along the guides 343 to hold fingertips and fix the fingers at the positions corresponding to the lengths thereof, as illustrated in FIG. 18.

Note that the shape and configuration of the fourth subject fixing unit 33d may be modified appropriately.

The fifth subject fixing unit 33e includes a fixing rod 347 to be fixed to the base unit 31, and a hand support 349 on which fingers, i.e., radiographic subjects, can be placed, as illustrated in FIGS. 19A to 19C and 20.

One end of the fixing rod 347 is fixed to the hand support 349. The opposite free end of the fixing rod 347 has a fixing screw 348 for fixing the fifth subject fixing unit 33e to the base unit 31. The base unit 31 has a hole (not shown) under the wrist fixing belt 313. The fifth subject fixing unit 33e is screwed into the hole of the base unit 31 using the fixing screw 348; as a result, the unit 33e is fixed to the base unit 31.

Figure 20:
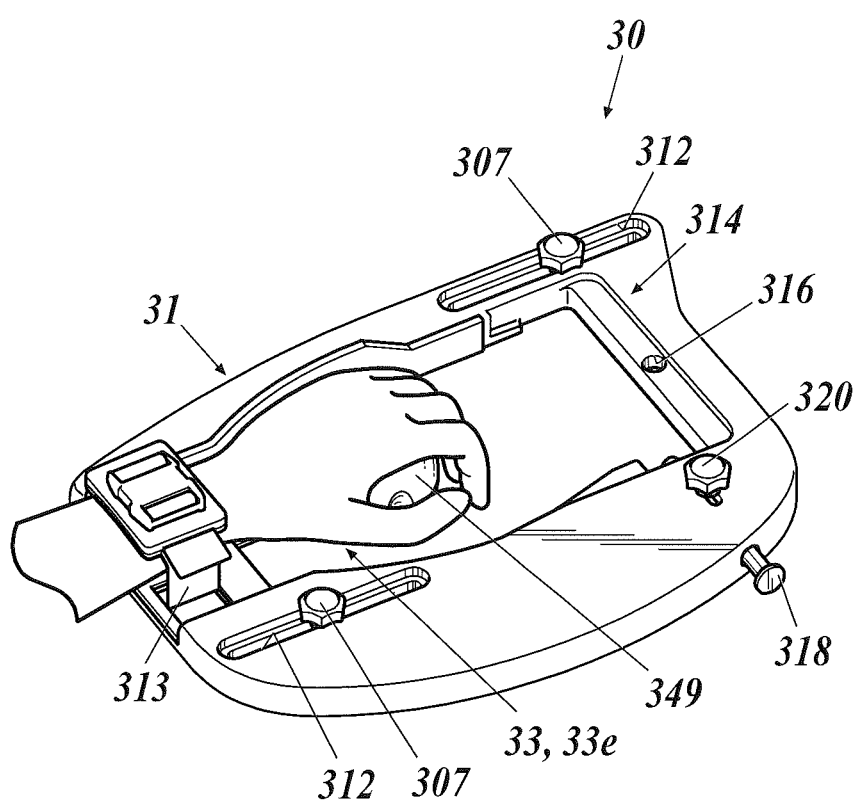
FIG. 20 is a perspective view illustrating the subject holder provided with the fifth subject fixing unit to which fingers are fixed.

The hand support 349 is a hemispherical member, and a patient places the hand on the support 349 with the subject fingers lightly bent to fix the fingers, as illustrated in FIG. 20. In the case where a joint cannot be stretched due to rheumatism or the case of radiography with fingers being lightly bent, a relatively easy posture results in little burdens on patients, leading to stabilized positions and angles of the fingers and the sure fixation of the fingers without deviations and tremor during radiography.

Note that the shape and configuration of the fifth subject fixing unit 33e may be modified appropriately. For example, non-slip resin may be applied to the surface of the hand support 349 in order to allow patients to readily hold the portion. Grooves for fingers may also be provided in the hand support 349. Furthermore, several fifth subject fixing units 33e may also be prepared each having a fixing rod 347 with a different length and a hand support 349 with a different size, shape, and height, so that suitable one of the units 33e can be used for radiography depending on the shape and size of a hand of a patient.

The sixth subject fixing unit 33f will be described with reference to FIGS. 21 to 28.

Figure 21:
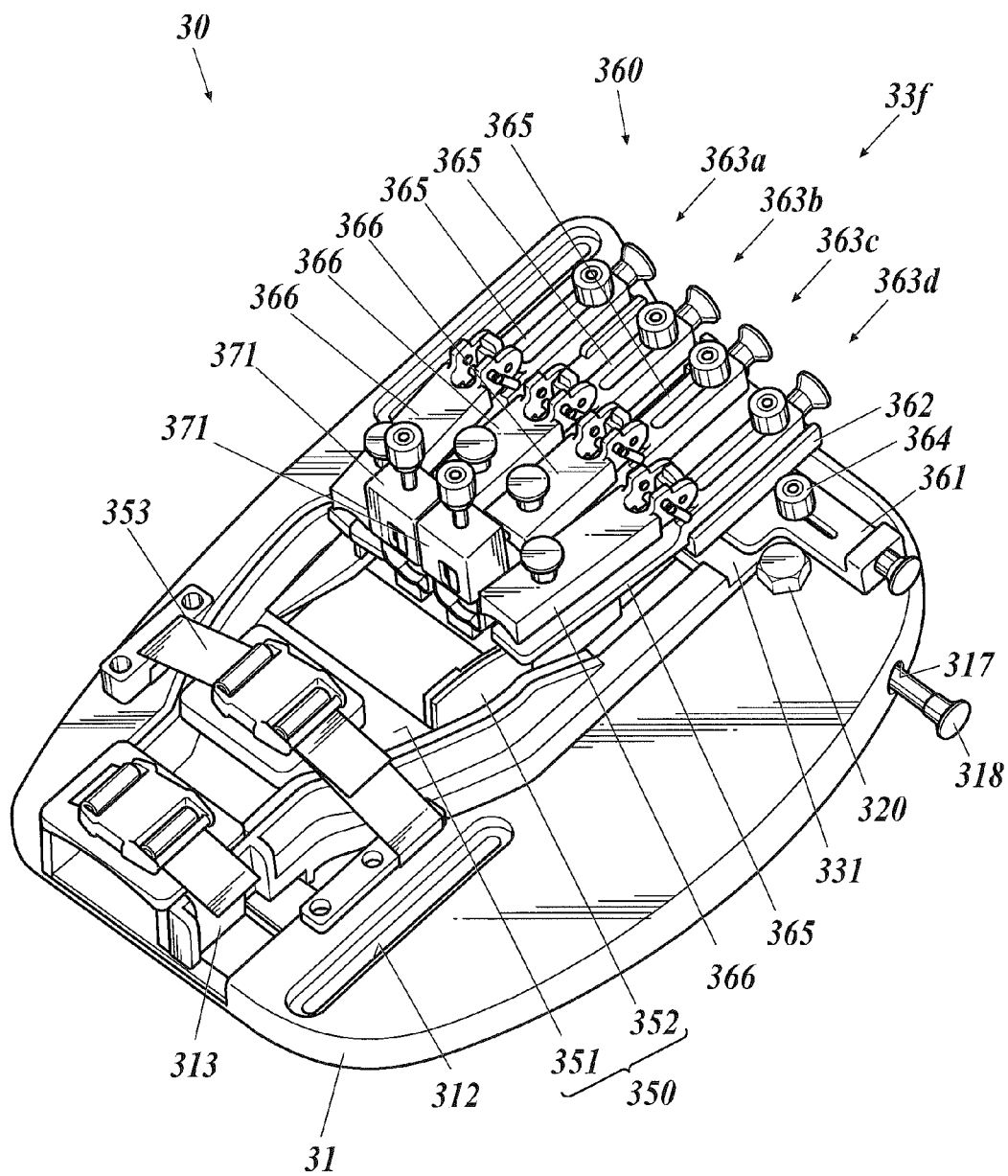
FIG. 21 is a perspective view illustrating the subject holder provided with a sixth subject fixing unit.

The sixth subject fixing unit 33f includes the fixing portion 331, a first fixing member 350, and a second fixing member 360 as illustrated in FIG. 21. The fixing portion 331 fixes the sixth subject fixing unit 33f to the base unit 31. The first fixing member 350 fixes a palm, which is a part on one side of the joints of fingers as a subject ("one side" is the side closer to the trunk of the patient than the other side with respect to the joints). The second fixing member 360 fixes the fingers, which are a part on the other side of the joints of fingers as a subject ("other side" is the side opposite to the "one side" with respect to the joints, i.e., the side remote from the trunk of the patient).

The sixth subject fixing unit 33f is the same as the subject fixing units 33a to 33e in that the unit can be detachably fixed to the base unit using the fixing portion 331.

The fixing portion 331 is the same as that of the first subject fixing unit 33a, and a redundant description thereof is omitted.

The first fixing member 350 is integrated with the fixing portion 331, and includes a flat palm support 351 to hold the palm of a hand and an upright finger regulator 352 to be disposed between the thumb and the other fingers to regulate positions and angles of the fingers.

The top surface of the palm support 351 is flat and level with the subject holder 30 placed on the top plate 3. The palm support 351 has an appropriate width to hold the palm of a hand. The finger regulator 352, which is perpendicular to the palm support 351, is provided at one end of the width direction of the palm support 351 (i.e., the same direction as the width direction of the fingers fixed to the subject fixing unit 33; hereinafter, simply referred to as "the width direction of the fingers" in the description of the sixth subject fixing unit 33f).

The finger regulator 352 is positioned between the thumb and the first finger of the fingers fixed to the subject holder 30. As a result, the finger regulator 352 can come into contact with the web between the thumb and the first finger to fix the palm on the palm support 351 and the fingers so as not to move forward.

A fixing belt 353 can fix the palm placed on the palm support 351 of the subject fixing unit 33f being fixed to the base unit 31 using the fixing pin 333, as illustrated in FIG. 21. The fixing belt 353 can prevent the bulge of the back of the hand.

Note that the fixing belt 353 may also be provided for fixing each of the first to fifth subject fixing units 33a to 33e to the base unit 31, not only for fixing the sixth subject fixing unit 33f to the base unit 31.

Figure 22:
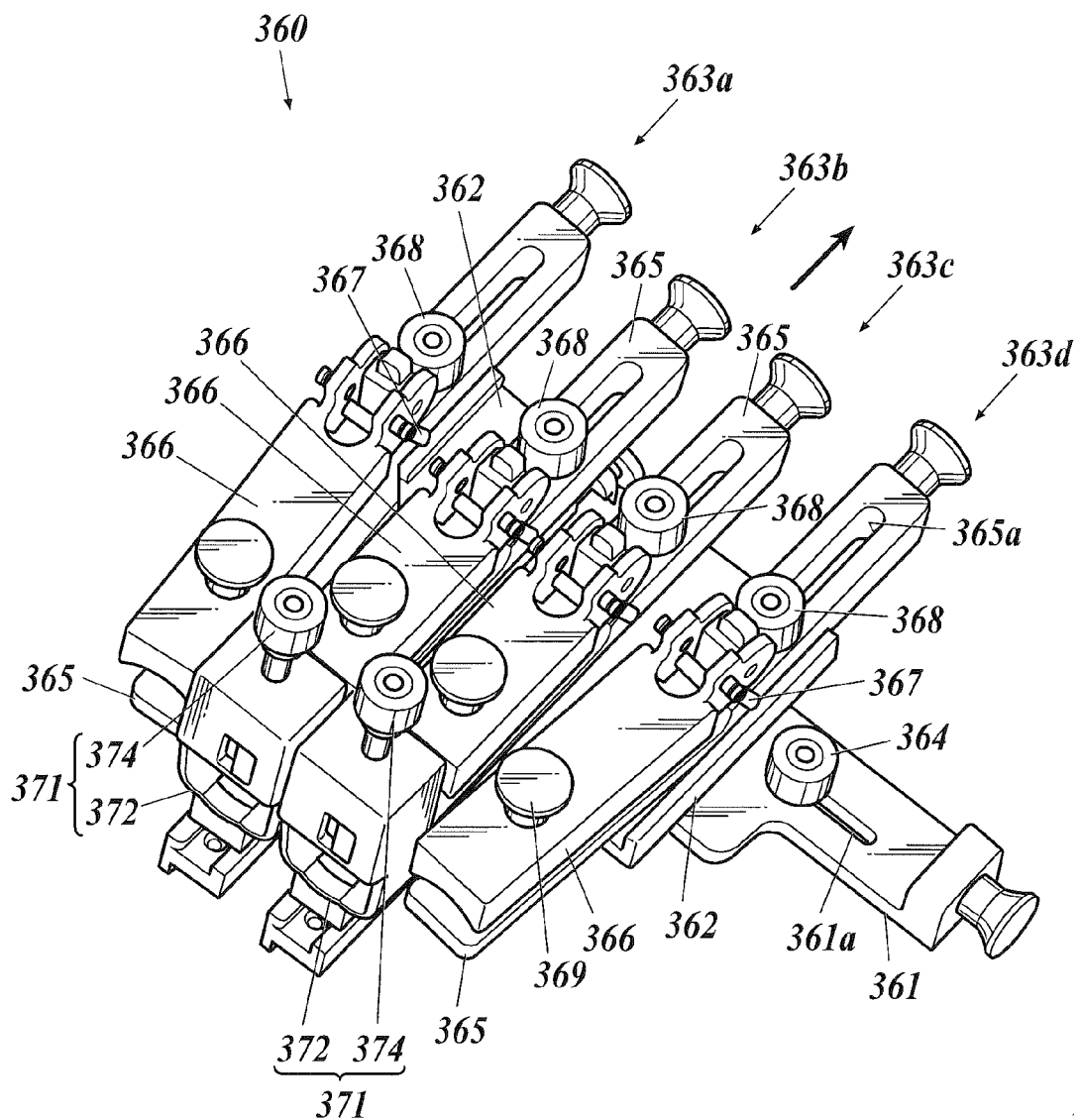
FIG. 22 is a perspective view illustrating a second fixing member for the sixth subject fixing unit.
Figure 23:
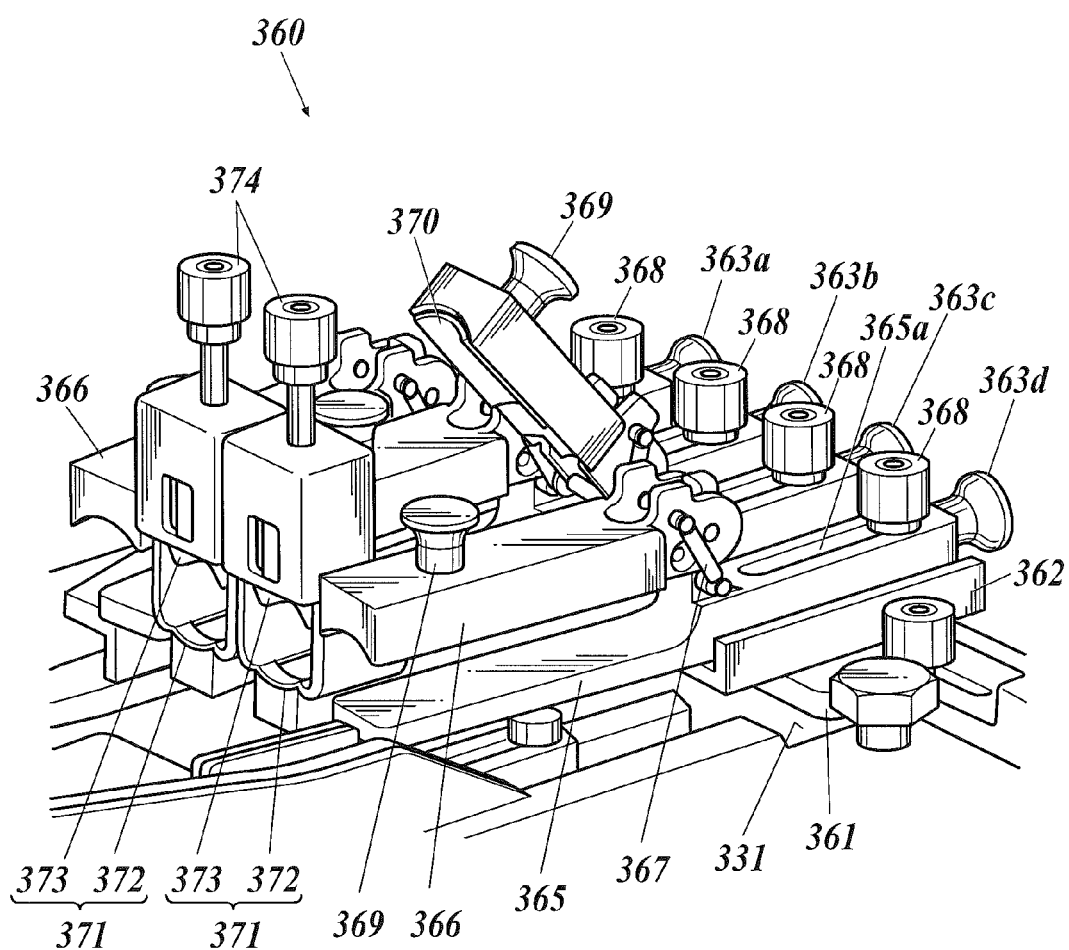
FIG. 23 is a perspective view illustrating the second fixing member viewed from another direction.

The second fixing member 360 includes a first base 361 mounted on the top of the fixing portion 331, two second bases 362 arranged along the width direction of the fingers and mounted on the top of the first base 361, and four grasping units 363a to 363d mounted on the top of the second bases 362, as illustrated in FIGS. 22 and 23.

The first base 361 is an elongated plate and attached to the top of the fixing portion 331 along the width direction of the fingers. The first base 361 has a through slot 361a provided along the longitudinal direction of the base. A screw 364 is inserted through the slot 361a of the first base 361 into a threaded bore (not shown) provided in the top of the fixing portion 331 and then the screw 364 is fastened. Thereby, the first base 361 is fixed to the fixing portion 331. In contrast, unscrewing the fastened screw 364 allows the first base 361 to be moved in the width direction of the fingers, and thereby the position of the first base 361 can be adjusted in the width direction.

A convex rail (not shown) is provided along the width direction of the fingers, on the top surface of the first base 361, and a groove (not shown) into which the rail of the first base 361 fits is provided in each of the bottom surfaces of the second bases 362. That is, fitting of the rail to the groove enables the positioning of the second bases 362 relative to the first base 361 along the width direction of the fingers. Then, the appropriately positioned second bases 362 can be fixed by fastening a screw (not shown) in each of the second bases 362.

The grasping units 363a and 363b are mounted on one of the second bases 362, and the grasping units 363c and 363d are mounted on the other. The grasping units 363a to 363d are arranged in series in the width direction of the fingers so as to grasp up to four fingers other than the thumb at a time. The outer two grasping units 363a and 363d have the same structure; the inner two grasping units 363b and 363c have the same structure. The grasping units 363a and 363d and the grasping units 363b and 363c will be individually described.

Each of the outer grasping units 363a and 363d includes a lower grasping member 365 and an upper grasping member 366 that hold a finger fixed to the subject fixing unit 33, a coil spring 367 that is an elastic member for applying grasping pressure to the grasping members 365 and 366, and a fastening screw 368 for supporting the lower grasping member 365 on the second base 362 such that the grasping member 365 can slide along its longitudinal direction.

The lower grasping members 365 extend on the top surfaces of the second bases 362 from the fingertips fixed to the subject fixing unit 33 to the wrist, and the upper grasping members 366 are rotatably anchored at ends of the top surfaces of the members 365 with hinges. The coil springs 367 are attached to the hinges with so-called tumbler springs. The coil springs 367 applies grasping pressure between the upper and lower grasping members 366 and 365 and keep a tension to maintain the raised upper grasping member 366.

Knobs 369 are provided on the top surfaces of the respective upper grasping members 366 to raise them against the grasping pressure. The bottom surfaces of the upper grasping members 366 have hollows along the longitudinal direction and elastic cushions 370. The cushions 370 may be made of a cellular or solid material. Preferably, the cellular material should be covered with a film or be of a closed-cell type so as not to absorb body fluids (e.g., blood or sweat).

When the upper and lower grasping members 366 and 365 hold fingers, the fingers can be guided into the hollows of the upper grasping members 366 and grasped along the longitudinal direction of the upper and lower grasping members 366 and 365. Furthermore, the cushions 370 can relieve grasping pressure, leading to a reduced burden on the fingers.

Long through slots 365a are provided in the lower grasping members 365 forward of the upper members 366, along the longitudinal direction. The lower grasping members 365 are fixed on the second bases 362 using the fastening screws 368 inserted in the slots 365a. That is, a position of the lower grasping member 365 can be adjusted along the longitudinal direction with the fastening screw 368 loosened, and the adjusted position can be maintained by fastening the screw 368.

In other words, a grasping position between the lower and the upper members 365 and 366 can be adjusted along the longitudinal direction of the fingers to properly hold joints to be stretched.

Although the configurations of the inner two grasping units 363b and 363c are similar to those of the grasping units 363a and 363d, the upper grasping members 366 of the grasping units 363b and 363c are shorter in the longitudinal direction than the lower grasping members 365. Finger restraint units 371 are provided at the distal ends of the lower grasping members 365.

Each of the restraint units 371 is mainly composed of a frame 372 for receiving a finger and a holder 373 for holding the finger inserted in the frame 372 by pressing.

The frame 372 has a hollow extending in the longitudinal direction of the lower grasping member 365, and an inserted finger can also be held by the upper grasping member 366 positioned forward thereof.

The holders 373 are held in the frames 372 and can come into contact with a finger inserted in the frame 372. The holders 373 are moved up and down by fastening and loosing screws 374 above the frame 372. The holders 373 are moved down using the screws 374 to hold fingers by a suitable pressing force.

The holders 373 are made of the same material as that of the cushions 370 to reduce a burden by relieving a holding pressure on the fingers.

The restraint units 371 are detachable from the lower grasping members 365 and can be attached to positions associated with the respective units 363a to 363d. Several restraint units 371 each having a frame 372 of a different size may also be prepared, so that a unit 371 having a frame 372 of a suitable size can be used for a finger swollen due to rheumatism.

The specification of the sixth subject fixing unit 33f will now be described with reference to instruction diagrams of FIGS. 24 to 28.

The outer grasping units 363a and 363d hold fingers between the lower and upper grasping members 365 and 366 with the joints stretched. The inner grasping units 363b and 363c hold fingers in the same manner and restrain the fingers in the restraint units 371, move the lower grasping members 365 forward, and fix them using the fastening screws 368, thereby maintaining the joints extended by pulling the fingers.

Thus, if a specific finger is required to be radiographed with its joint extended, the finger is restrained in the restraint unit 371 of the inner grasping unit 363b or 363c and then radiographed.

Figure 24:
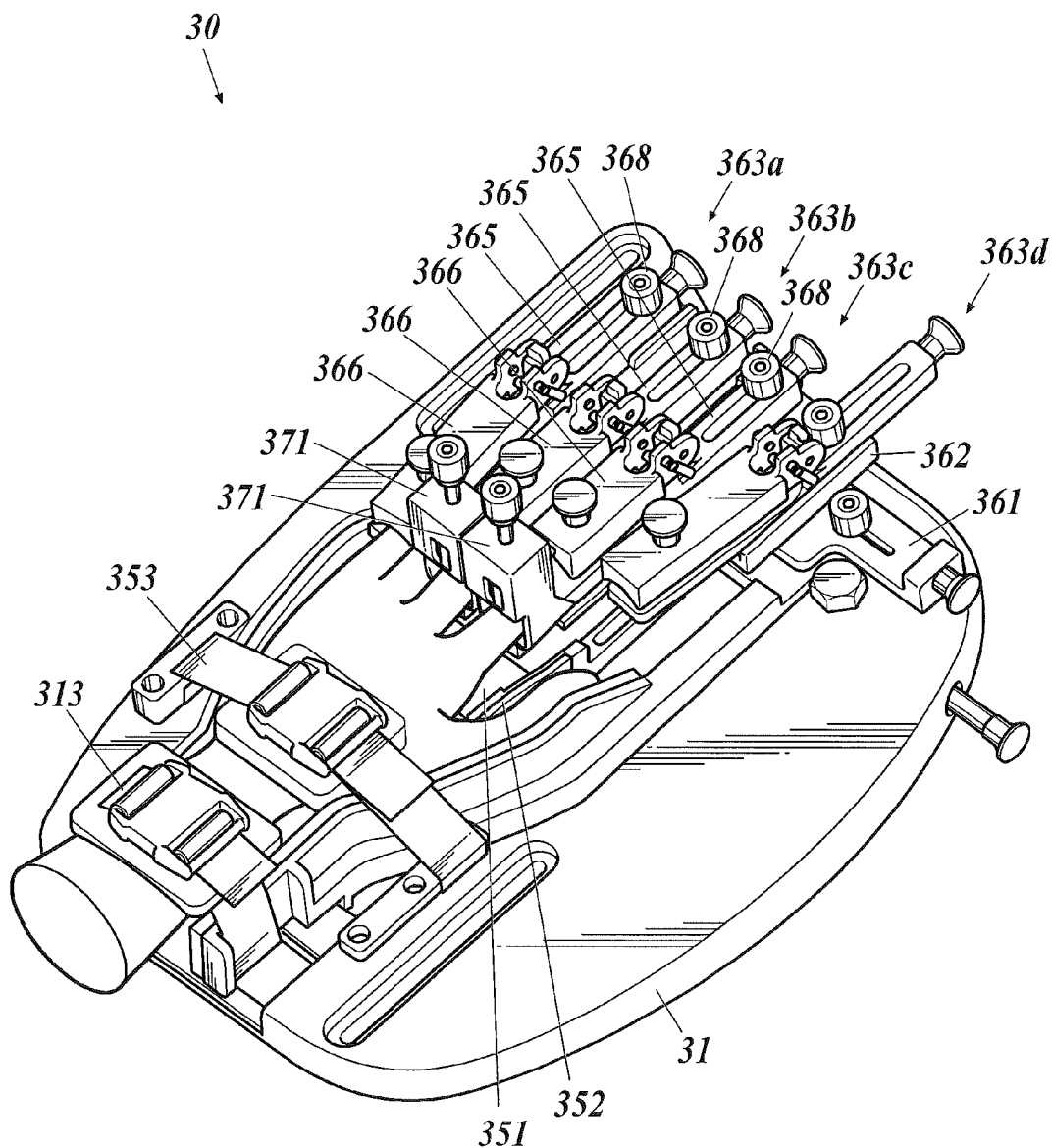
FIG. 24 is a perspective view illustrating the subject holder provided with the sixth subject fixing unit to which fingers are fixed, with grasping units moved toward the wrist.
Figure 25:
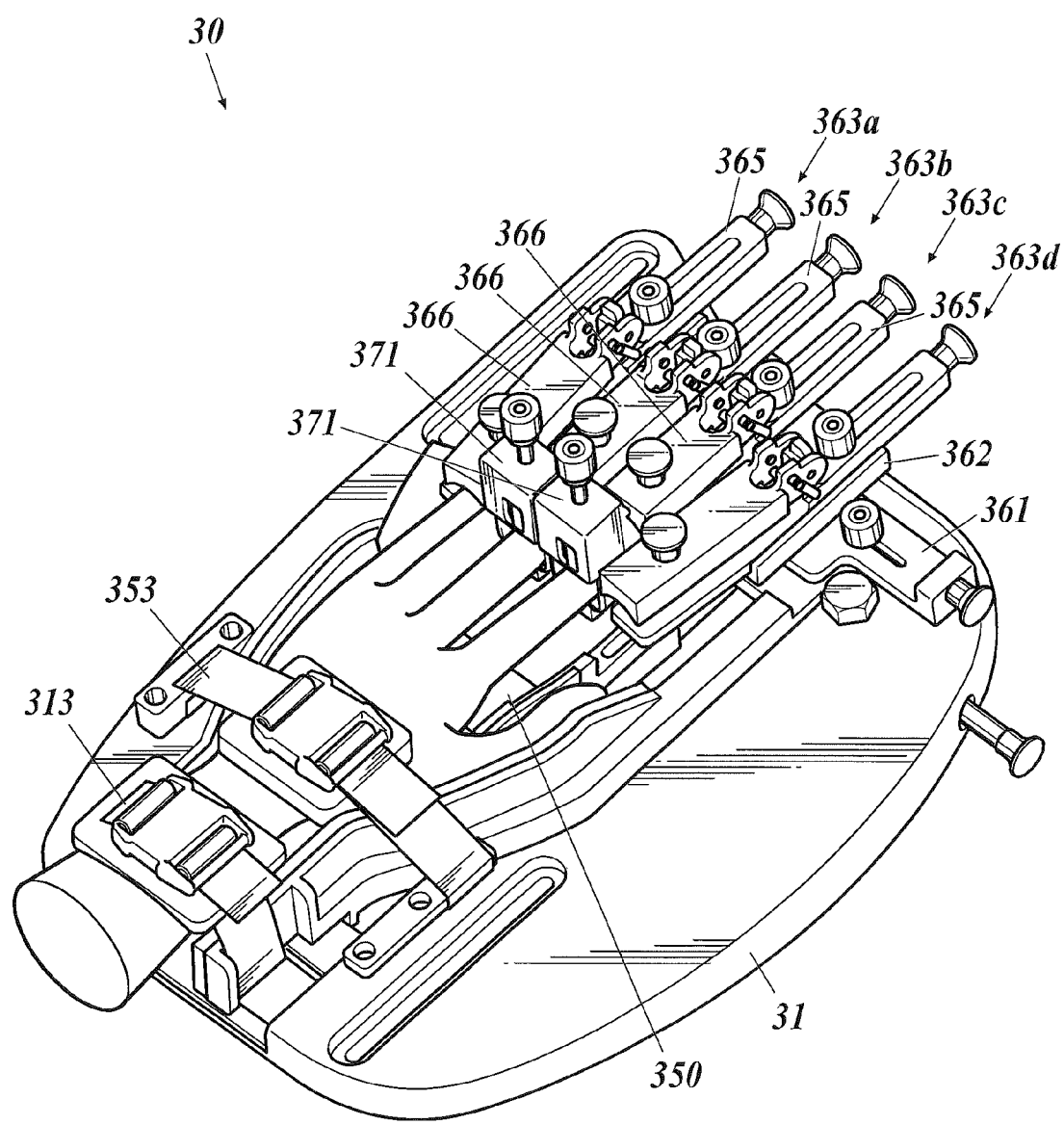
FIG. 25 is a perspective view illustrating the subject holder provided with the sixth subject fixing unit to which fingers are fixed, with the grasping units moved forward.

FIGS. 24 and 25 illustrate the restraint of the first and second fingers, which especially tend to develop rheumatism, to the grasping units 363b and 363c.

An imaging apparatus utilizing a one-dimensional grating produces a blur image of a joint, i.e., a subject, if a relative angle between the one-dimensional grating and spread fingers fixed on subject table is at or above a predetermined range. Only the first and second fingers, however, are radiographed in the present embodiment; hence, the quality of an image produced by simultaneously radiographing both the fingers is not compromised.

Note that an imaging apparatus utilizing a two-dimensional grating does not suffer from such principle limitations, so that such an apparatus can radiograph even every finger at a time.

The palm of a left hand is placed on the palm support 351, and the fixing belts 313 and 353 fix the wrist and the back of the hand, respectively, with the finger regulator 352 between the thumb and the first finger, as illustrated in FIG. 24. The grasping units 363a, 363b, and 363c, which are used with the fastening screws 368 loosed, are moved in the direction from the fingertips to the wrist. The restraint units 371 of the grasping units 363b and 363c then restrain the first and second fingers, and the corresponding upper grasping members 366 are tilted to hold the fingers. At this time, even if the third and fourth fingers are not to be radiographed, the upper grasping members 366 therefor should be laid so as not to obstruct radiography although these fingers need not be held.

The grasping units 363a, 363b, and 363c are then moved in the direction from the wrist to the fingertips, as illustrated in FIG. 25. The distance of the movement is adjusted so as not to cause a burden on the patient. Finally, the lower grasping members 365 are fastened using the respective fastening screws 368.

Figure 26A:
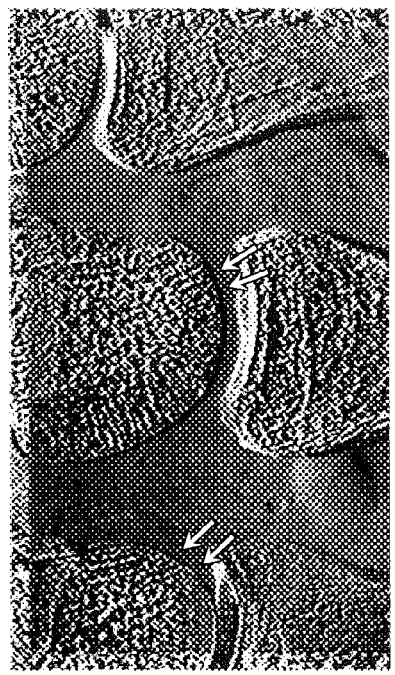
FIG. 26A is a radiograph taken without stretching fingers.
Figure 26B:
FIG. 26B is a radiograph taken with fingers being stretched with restraint units.

FIG. 26A is a radiograph taken without pulling a finger; whereas FIG. 26B is a radiograph taken with the finger being pulled using the restraint units 371. Pulling a finger extends its joint such that the outline of a cartilage can be confirmed, as seen from the images. That is, since a joint can be radiographed with the extension of the joint being kept, the positioning of fingers is facilitated and thus quick radiography is provided.

Figure 27:
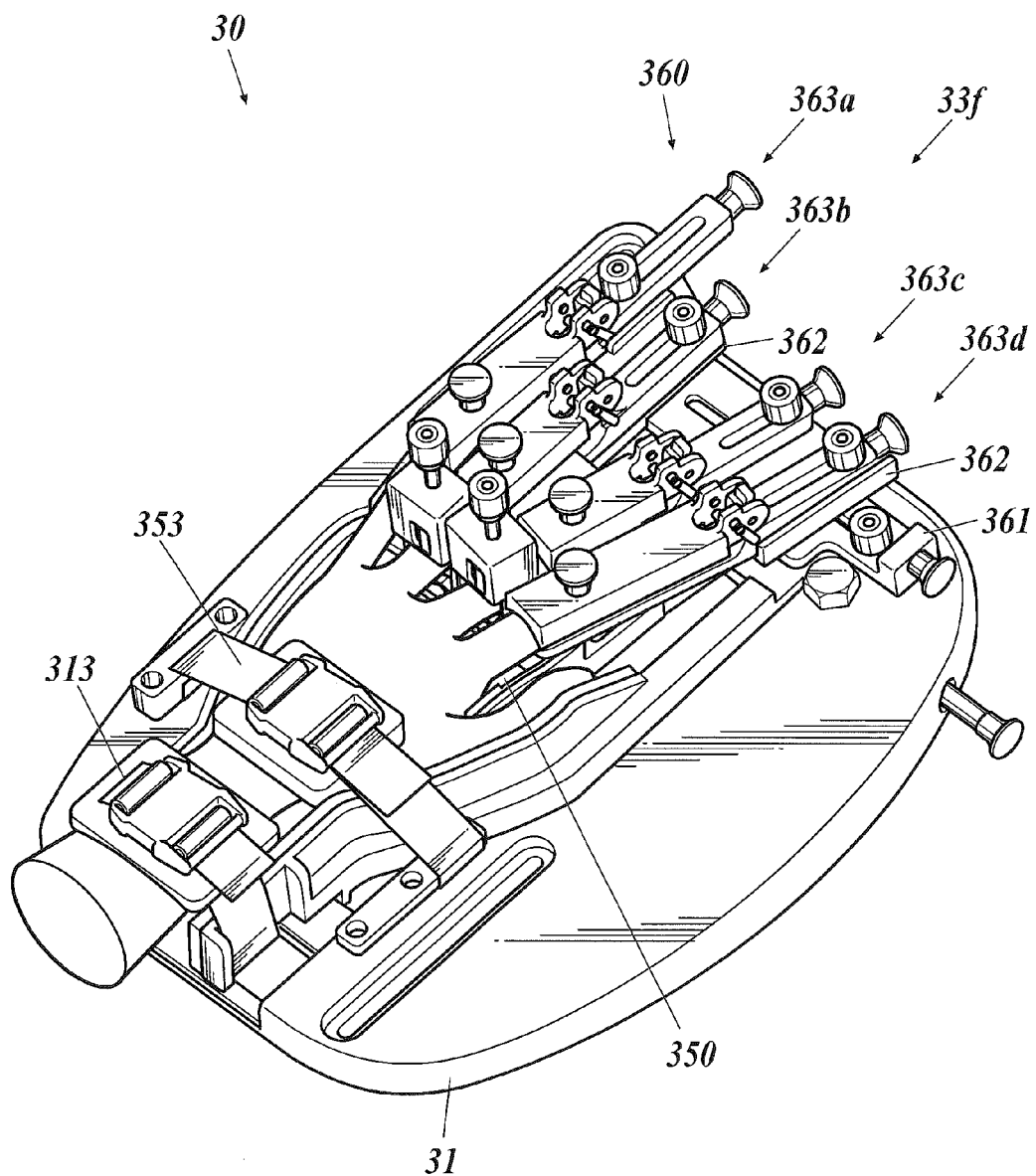
FIG. 27 is a perspective view illustrating the sixth subject fixing unit including other grasping units.
Figure 28:
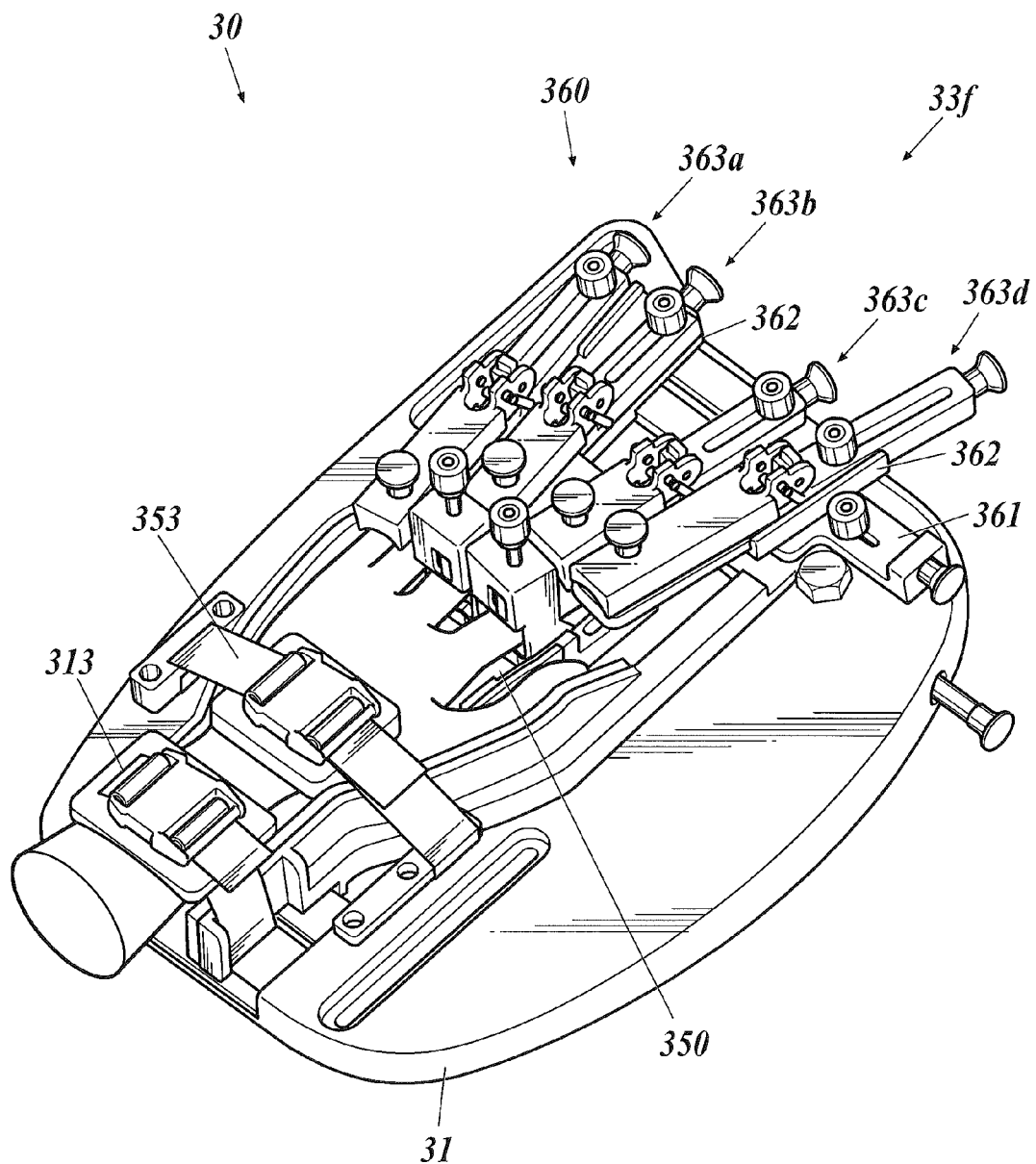
FIG. 28 is a perspective view illustrating the sixth subject fixing unit after the positions of the grasping units are varied.

As illustrated in FIGS. 27 and 28, any one of the grasping units 363a to 363d may be selected to grasp a corresponding finger. At this time, the position of the first base 361 and the second bases 362 can be adjusted in the width direction of the fingers as appropriate depending on the combination of the grasping unit to be used and the finger to be grasped. As a result, a finger can be radiographed with its position properly kept.

FIG. 29 schematically illustrates primary parts of the joint imaging apparatus 1 according to the present embodiment.

In the present embodiment, the joint imaging apparatus 1 includes the X-ray source 11, the multi-slit grating 12, the main portion 65 of the light field confirming unit, the subject holder 30 of the subject table 13, the first grating 14, the second grating 15, and the X-ray detector 16 in this order along the z direction, which is the direction of gravitational force (see FIG. 1).

The X-ray source 11 is connected to a substantially U-shaped fixing member 111 via an arm 112. In the present embodiment, the post 17 is a quadratic prism, and the fixing member 111 is fixed to the post 17 by clutching the post 17.

The arm 112 includes a cushion 17a (see FIG. 1), and the X-ray source 11 is held via the cushion 17a. The cushion 17a may be composed of any material that can absorb shocks and vibrations, such as an elastomeric material. Since the X-ray source 11 generates heat during emission of X-rays, one side of the cushion 17a adjacent to the X-ray source 11 is preferably made of a material that can absorb shocks and vibrations and insulate heat.

The X-ray source 11 includes an X-ray tube. The X-ray source 11 emits X-rays generated by the X-ray tube in the direction of gravitational force (z direction). Examples of X-ray tubes include a Coolidge X-ray tube and a rotating anode X-ray tube, which are generally used in medical facilities. The anode may be composed of tungsten or molybdenum.

The diameter of the focus of X-rays preferably ranges from 0.03 to 3 (mm), and more preferably from 0.1 to 1 (mm).

In the present embodiment, a part of the arm 112 can be bent at a substantially right angle, so that the X-ray source 11 can be rotated by about 90 degrees with respect to the slits of the multi-slit grating 12, the first grating 14, and the second grating 15, the parallelism and relative distances of which are adjusted, as illustrated in FIGS. 5 and 6.

In the present embodiment, the focus shape of the X-ray tube in the X-ray source 11 is rather elliptic than circular, such that modifying the orientation of the X-ray tube may lead to proper moire images in the radiography for creating moire images as described later. Thus, rotation of about 90 degrees of the X-ray source 11 can eliminate faults due to the shape of the focus of the X-ray tube.

Note that any other configuration may also allow modification of the orientation of the X-ray source 11 with respect to the slits of the multi-slit grating 12 and the first and second gratings 14 and 15. For example, modifying the position of the fixing member 111 may vary the orientation of the X-ray source 11. Furthermore, the orientation of the X-ray source 11 may also be minutely adjusted, not only by 90 degrees.

In the present embodiment, the end of the arm 112 for fixing the X-ray source 11 is rotatable, as illustrated in FIG. 8. Accordingly, the direction of X-rays emitted from the X-ray source 11 can be varied from a radiographic mode, where the optical axis of X-rays emitted from the X-ray source 11 is substantially parallel to the post 17 and the X-rays passing through the multi-slit grating 12 and the first and second gratings 14 and 15 (see FIG. 7), to a calibration mode, where the optical axis of X-rays deviates from the multi-slit grating 12 and the first and second gratings 14 and 15 (see FIG. 8).

Note that the X-ray source 11 may also emit X-rays in any other direction during the calibration as long as the optical axis of X-rays deviates from the multi-slit grating 12 and the first and second gratings 14 and 15. If the X-ray source 11 emits X-rays in another direction during the calibration, the position of the X-ray detector holder 25 is adjusted onto the optical axis of an X-ray emitted from the X-ray source 11.

An aperture 113 and a filter 114 are provided immediately below the X-ray source 11 and the multi-slit grating 12 described later.

The aperture 113 narrows the field irradiated with X-rays emitted from the X-ray source 11, to a predetermined area.

The filter 114 separates unnecessary wavelength components from a beam emitted from the X-ray source 11. For example, an additional Al filter may be used.

The light field confirming unit 6 includes a substantially L-shaped base mount 61 attached to the support 19 and the main portion 65 affixed on the base mount 61, as illustrated in FIGS. 3 and 5. The base mount 61 is fixed to the support 19 using screws (not shown).

A guide 63 is provided on the plane of the base mount 61 which is substantially horizontal to the floor surface. The guide 63 is used to move the main portion 65 in the x direction, and the main portion 65 can be manually or automatically moved therealong.

The light field confirming unit 6 emits visible light to the field to be irradiated with X-rays emitted from the X-ray source 11 in order to confirm this irradiation field in advance. The main portion 65 includes a light source (not shown) that can emit visible light.

The main portion 65 also includes the lever 67 extending from the back side of the joint imaging apparatus 1 (i.e., the side of the post 17) to the front, substantially horizontally to the floor surface. The lever 67 is used to manually move the main portion 65 along the guide 63 in the x direction. The distal end of the lever 67 protrudes from the opening 211c in the first cover unit 21 covering the joint imaging apparatus 1, as described above.

In the present embodiment, the main portion 65 may be at a confirmation position or at a retracted position. At the confirmation position, the optical axis of light from the light source aligns with that of X-rays emitted from the X-ray source 11, and thus the user can confirm a light field. The main portion 65 at the retracted position does not block X-rays emitted from the X-ray source 11. In normal radiographic use of the joint imaging apparatus, the main portion 65 is positioned at the retracted position (denoted by the solid lines in FIG. 29) so as not to interfere with the radiography. To confirm the light field, the user operates the lever 67 such that the main portion 65 moves to the light field confirmation position (denoted by the dotted lines in FIG. 29), that is, until the optical axis of light from the light source in the main portion 65 aligns with that of an X-ray emitted from the X-ray source 11. Note that the main portion 65 may also be automatically moved in the x direction by a motor.

In the present embodiment, a light field can be accurately confirmed since the main portion 65 and the first and second gratings 14 and 15 have no obstruction to light therebetween.

The multi-slit grating unit 120, the first grating unit 140, the second grating unit 150, and the X-ray detector 16 are held on the support 19 in the fixed positional relationship in the z direction. The multi-slit grating unit 120, the first grating unit 140, and the second grating unit 150 extend in the direction orthogonal to that of gravitational force (i.e., the z direction), and these units are detachably fixed to the support 19 using screws.

The light field confirming unit 6 is provided on the support 19 and immediately below the multi-slit grating unit 120.

The X-ray detector 16 is mounted on a detector support 191 provided on the support 19, via a cushion 192.

Note that the support 19 may also move in the z direction with respect to the post 17.

Figure 30:
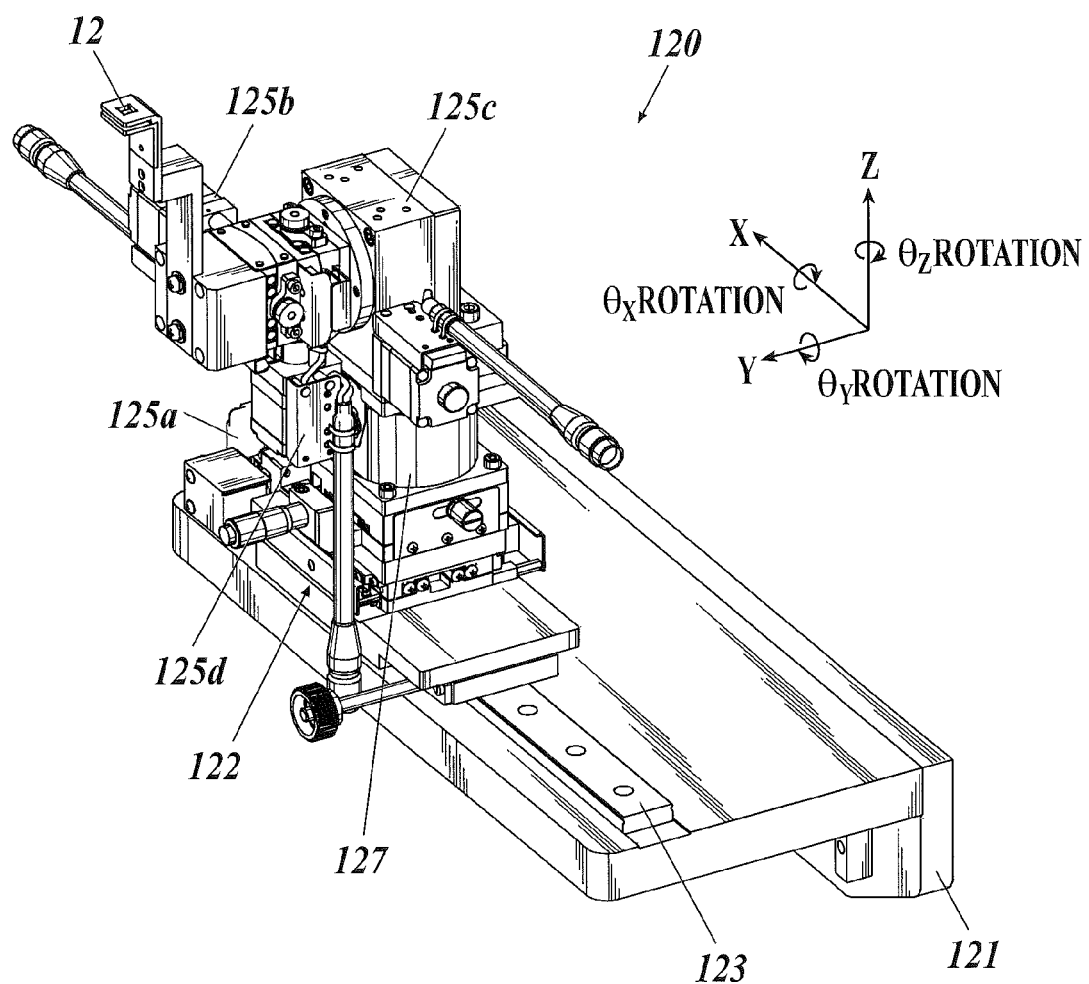
FIG. 30 is a perspective view of a multi-slit grating unit.

FIG. 30 is a perspective view illustrating the multi-slit grating unit 120.

The multi-slit grating unit 120 includes a substantially L-shaped base mount 121 to be secured to the support 19 and a multi-slit grating unit main portion 122 mounted on the base mount 121, as illustrated in FIG. 30.

A linear guide 123 is provided on an area of the base mount 121 substantially horizontal to the floor surface. The guide 123 is used to move the main portion 122 in the x direction.

Adjusting the position of the base mount 121 fixed to the support 19 allows the adjustment of the relative distances between the multi-slit grating 12 and the first and second gratings 14 and 15. The main portion 122 includes a distance fine-adjuster 127. The height of the multi-slit grating 12 can be adjusted by varying the length of the distance fine-adjuster 127 in the direction of gravitational force (i.e., the vertical direction). In the present embodiment, the combination of the base mount 121 and the distance fine-adjuster 127 functions as a mechanism for adjusting the relative distances between the multi-slit grating 12 and the first and second gratings 14 and 15.

Since the multi-slit grating unit is relatively heavy, it is preferable that the position of the base mount 121 and that of the distance fine-adjuster 127 be adjusted individually from viewpoints of workability, safety, and ease of positioning. That is, the base mount 121 is preferably fixed tentatively to the support 19 with positioning pins (the position is unadjustable) and then the base mount 121 is screwed (fixed) thereto. Thereafter, the user preferably finely adjusts the relative distance using the distance fine-adjuster 127 in the main portion 122 by both hands.

The main portion 122 includes the multi-slit grating 12 supported thereto, a motor 125a for moving the multi-slit grating 12 in the x direction, a θx rotation motor 125b for rotating the multi-slit grating 12 about an axis extending in the x direction, a θy rotation motor 125c for rotating the multi-slit grating 12 about an axis extending in the y direction, and a θz rotation motor 125d for rotating the multi-slit grating 12 about an axis extending in the z direction, as a multi-slit grating driver 125.

Figure 31:
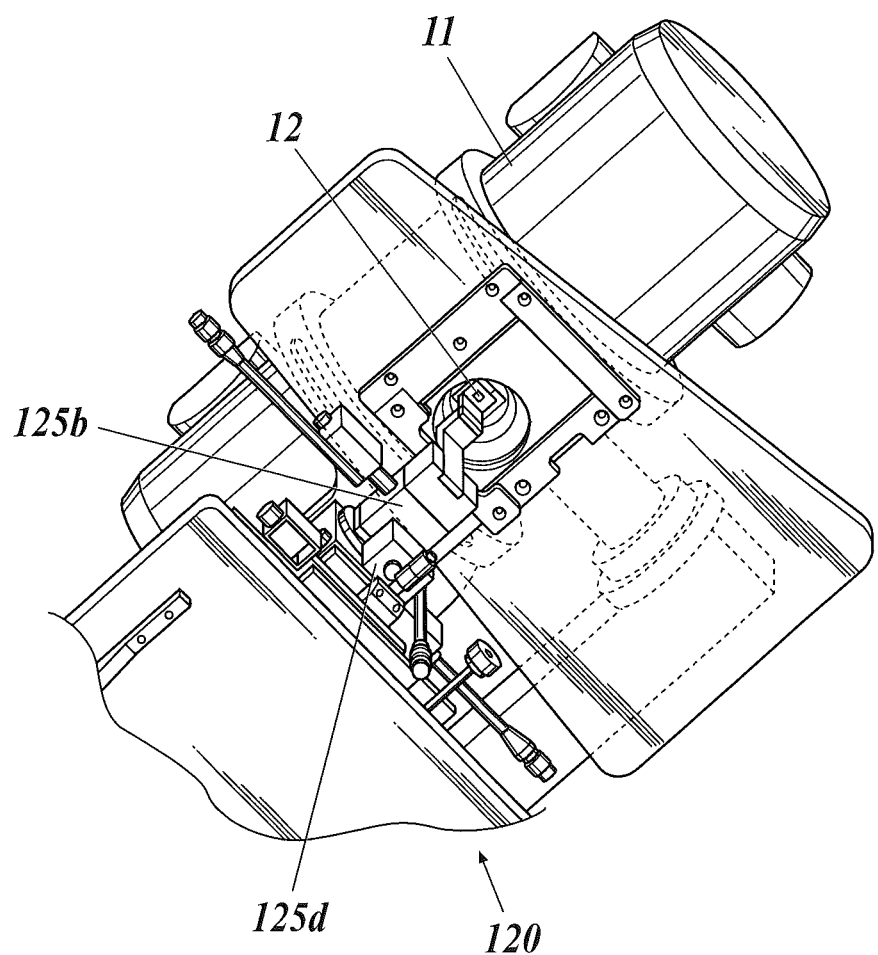
FIG. 31 is a perspective view illustrating an X-ray source and the multi-slit grating unit disposed thereunder.

In the present embodiment, the multi-slit grating 12 is inserted in the X-ray source 11 from below and positioned near the focus of the X-ray tube, as illustrated in FIG. 31.

The motor 125a is a driving source that operates under the energized state. For example, the motor 125a is a motor that can operate with high accuracy, such as a stepping motor (pulse motor), which operates in synchronization with a pulse signal. A stepping motor applied to the motor 125a is preferably a five-phase stepping motor such as the one manufactured by ORIENTAL MOTOR Co., Ltd. (model: PX533MH-B), and more preferably a high-resolution model. A general stepping motor has a base step angle of 0.72° whereas a high-resolution model has 0.36°; hence, the latter is preferably used. Microstepping for achieving finer steps is more preferred.

In the present embodiment, the driving power of the motor 125a, which is a driving source, turns a ball screw (not shown) that transmits the output from the driving source to the main body of the multi-slit grating unit 120 including the multi-slit grating 12 to be driven, and thereby the multi-slit grating unit 120 including the multi-slit grating 12 is moved in the x direction along the linear guide 123.

The motor 125a, which is the driving source; the ball screw, which is a transmission system; and the linear guide configure a moving unit of the multi-slit grating unit 120. The moving unit consists of elements that move perpendicularly to the gravitational force (i.e., the z direction).

In the present embodiment, the motor 125a moves the multi-slit grating 12 with a maximum output. During X-ray emission, the multi-slit grating driver 125 lowers the energizing current for the motor 125a to a current that provides not more than 50% of the displacement of the multi-slit grating 12 caused by the maximum output from the motor.

In the case of multiple radiographic exposures with the multi-slit grating 12 being shifted, each position of the multi-slit grating 12 should be accurately maintained by the selfholding force of the motor 125a under the energized state. In such a case where the multi-slit grating 12 is sequentially shifted from a current position to a next one to make multiple radiographic exposures, the current position of the multi-slit grating 12 cannot be fed back for the next shift if the motor is powered off. For this reason, the motor 125a must be energized even if the multi-slit grating 12 holds its position (i.e., at the time of X-ray emission) until a predetermined number of radiographic exposures are finished.

However, excess current applied to the motor 125a causes the motor 125a to produce heat and microvibrations. The vibrations may propagate through the ball screw, resulting in minute displacement of the multi-slit grating 12.

Figure 32:
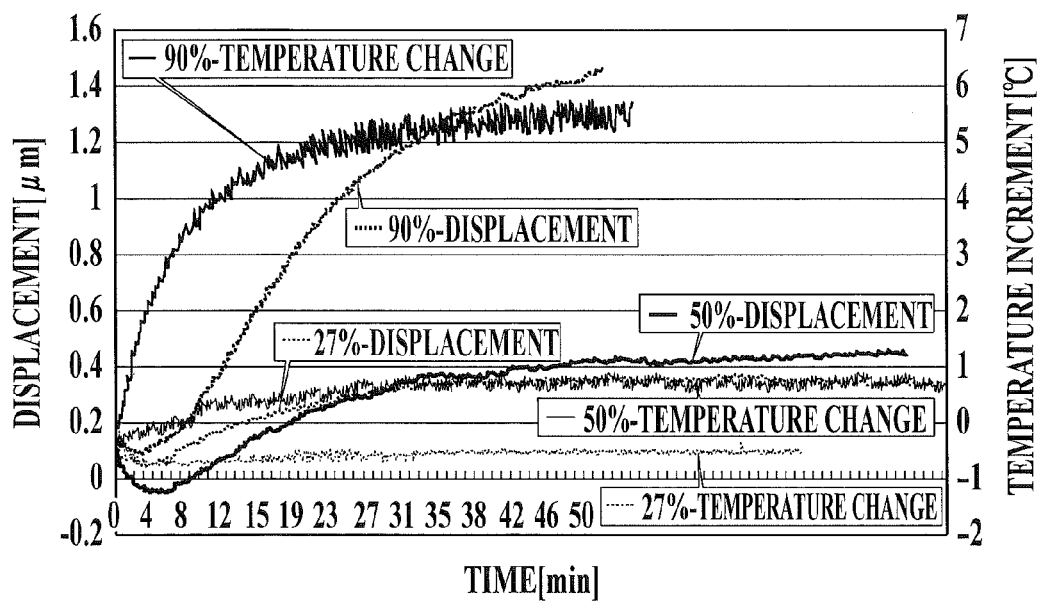
FIG. 32 is a graph illustrating the relationship between exciting currents and displacement of the multi-slit grating.

FIG. 32 is a graph illustrating the relationship between several exciting currents and temperature change and between the exciting currents and the displacement of the multi-slit grating 12, where the horizontal axis represents time (min) while the vertical axis represents the displacement (μm) of the multi-slit grating 12 and temperature change (° C.).

The displacement illustrated in FIG. 32 indicates observed displacement of the multi-slit grating 12 from the initial position (zero) in the movement direction (i.e., the x direction) caused by each exciting current and temperature change. The increment of the temperature in FIG. 32 indicates an observed temperature change in the motor 125a caused by the application of exciting current of respective values.

An exciting current corresponding to about 90% of the maximum output from the motor causes an increase in the temperature in the motor 125a and accelerates the displacement of the multi-slit grating 12 over time, eventually causing the displacement to exceed 1.4 μm, as illustrated in FIG. 32. In contrast, an exciting current corresponding to about 27% of the maximum output from the motor causes a slight or negligible increase in the temperature in the motor 125a over time and the displacement of the multi-slit grating 12 also remains at about 0.3 μm. An exciting current corresponding to about 50% of the maximum output from the motor also causes a slight or negligible increase in the temperature in the motor 125a over time and the displacement of the multi-slit grating 12 also remains at about 0.45 μm.

In order to produce suitable moire images, the accuracy of the transfer rate of the multi-slit grating 12 by the motor 125a must be 1/10 or less of each transfer distance. For example, if the multi-slit grating 12 is moved five times for as many radiographic exposures to produce moire images, the multi-slit grating 12 is shifted by 1/5 of the grating pitch at each time. If the multi-slit grating 12 is moved three times for as many radiographic exposures to produce moire images, the multi-slit grating 12 is shifted by 1/3 of the grating pitch at each time. Thus, for example, if the grating pitch is 22.8 μm and the grating transfer rate is 5.7 μm, the required accuracy (relative grating position) is at most ±0.23 μm (P-P: 0.46 μm).

In the present embodiment, an exciting current not greater than about 50% of that providing the maximum motor output satisfies the required accuracy (relative grating position) and thus the current applied to the motor 125a will not affect the generation of moire images.

Note that the threshold of the exciting current applied to the motor 125a that affects the generation of moire images, that is, the level of "the current that provides not more than 50% of the displacement of the multi-slit grating 12 caused by the maximum output from the motor" depends on the type of the motor. For this reason, the exciting current during X-ray emission is preferably determined depending on the adopted motor as appropriate.

The θx rotation motor 125b, the θy rotation motor 125c, and the θz rotation motor 125d configure a goniometer stage each including an actuator as a driving source, for example. They have a tilt adjusting mechanism for adjusting the parallelism between the multi-slit grating 12 and the first and second gratings 14 and 15.

Figure 33:
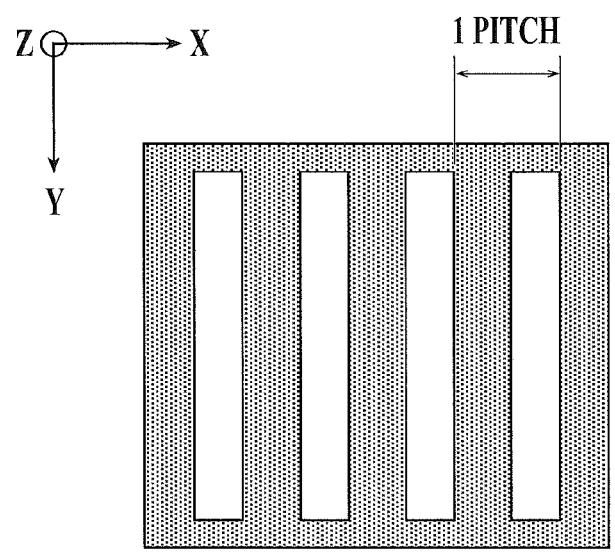
FIG. 33 is a plan view of the multi-slit grating.

The multi-slit grating 12 installed in the multi-slit grating unit 120 is a diffraction grating having multiple slits provided at predetermined intervals in the x direction, as illustrated in FIG. 33. The multi-slit grating 12 is composed of a substrate made of a material having low radiation absorptivity such as silicon or glass and an upper member made of another material having high radiation shielding effects (i.e., having high radiation absorptivity) such as tungsten, lead, or gold. For example, a material is masked with resist by photolithography to form slits, and the slit pattern is transferred on the resist by irradiation with UV light. Slits having the same shape as the mask pattern are provided by exposure. Finally, the slits are filled with metal by electroforming to give the multi-slit grating 12.

The slit pitch of the multi-slit grating 12 ranges from 1 to 60 (μm). One slit pitch is the distance between two adjacent slits as illustrated in FIG. 33. The width of a slit (the length in the x direction) preferably ranges from 1 to 60 (%), and more preferably from 10 to 40 (%) of the slit pitch. The height of a slit (the length in the z direction) preferably ranges from 1 to 500 (μm), and more preferably from 1 to 150 (μm).

Assuming that the slit pitch of the multi-slit grating 12 is w0 (μm) and the slit pitch of the first grating 14 is w1 (μm), the slit pitch w0 can be determined as follows:

$$w0 = w1(d3+d4)/d4.$$

Provided that the slit pitch w0 is determined to satisfy the equation, self-images formed by X-rays passing through the slits of the multi-slit grating 12 and the first grating 14 can overlap each other in focus on the second grating 15.

The first grating 14 is a diffraction grating having multiple slits provided in the x direction similarly to the multi-slit grating 12. The first grating 14 may be formed by photolithography using UV light, similarly to the multi-slit grating 12, or may also have a grating structure made of only silicon by providing fine deep lines in a silicon substrate using an ICP (inductively coupled plasma) process. A slit pitch of the first grating 14 ranges from 1 to 20 (μm). The width of a slit preferably ranges from 20 to 70 (%) of the slit pitch, and more preferably 35 to 60 (%). The height of a slit ranges from 1 to 100 (μm).

If the first grating 14 is of a phase type, the height of the slits (length in the z direction) is determined such that a phase difference (in X-rays) between two materials forming the slit pitch, i.e., a phase different between the X-ray transmitting portion and the X-ray shielding portion preferably ranges from π/8 to 15π/8, and more preferably from π/4 to 3π/4. If the first grating 14 is of an adsorptive type, the height of the slits is determined such that the X-ray shielding portion sufficiently absorbs X-rays.

If the first grating 14 is of a phase type, the distance d4 between the first grating 14 and the second grating 15 must substantially satisfy the following condition:

$$d4 = (m+(\tfrac{1}{2}))w1^2/\lambda$$

where m is an integer, and λ is a wavelength of X-rays.

The second grating 15 is a diffraction grating having multiple slits in the x direction similarly to the multi-slit grating 12 and the first grating 14. The second grating 15 can also be formed by photolithography. The slit pitch of the second grating 15 ranges from 1 to 20 (μm). The width of a slit preferably ranges from 30 to 70 (%) of the slit pitch, and more preferably 35 to 60 (%). The height of a slit ranges from 1 to 100 (μm).

The respective grating surfaces of the first and second gratings 14 and 15 of the present embodiment are perpendicular to the z direction (i.e., parallel to the x-y plane). The first grating and the second grating are arranged such that the slits of the first grating and those of the second grating are arranged at a predetermined angle with each other in the x-y plane, but they may also be parallel to each other.

The first and second gratings 14 and 15 are provided in the first and second grating units 140 and 150, respectively, which have substantially the same configuration.

Figure 34:
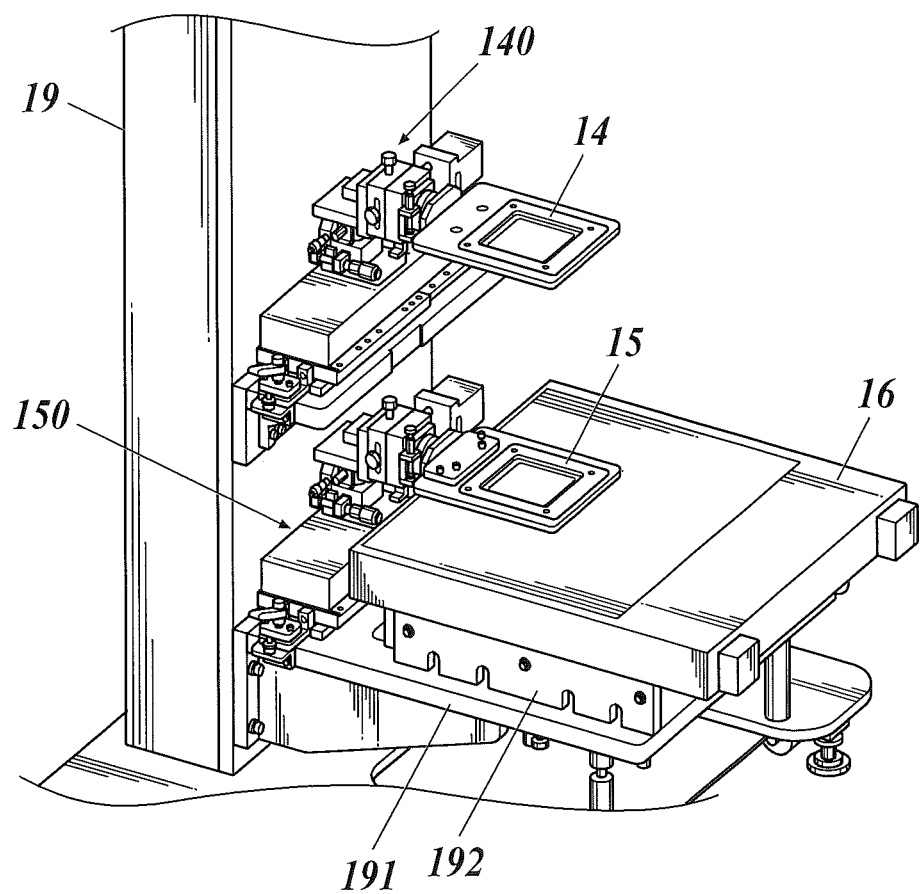
FIG. 34 is a perspective view illustrating a first grating unit and a second grating unit both attached to a support.

FIG. 34 is an enlarged perspective view illustrating the first and second grating units 140 and 150 both attached to the support 19. The second grating 15 of the second grating unit 150 is positioned immediately above the X-ray detector 16, as illustrated in FIG. 34. The first grating 14 of the first grating unit 140 is positioned above the second grating 15.

Figure 35:
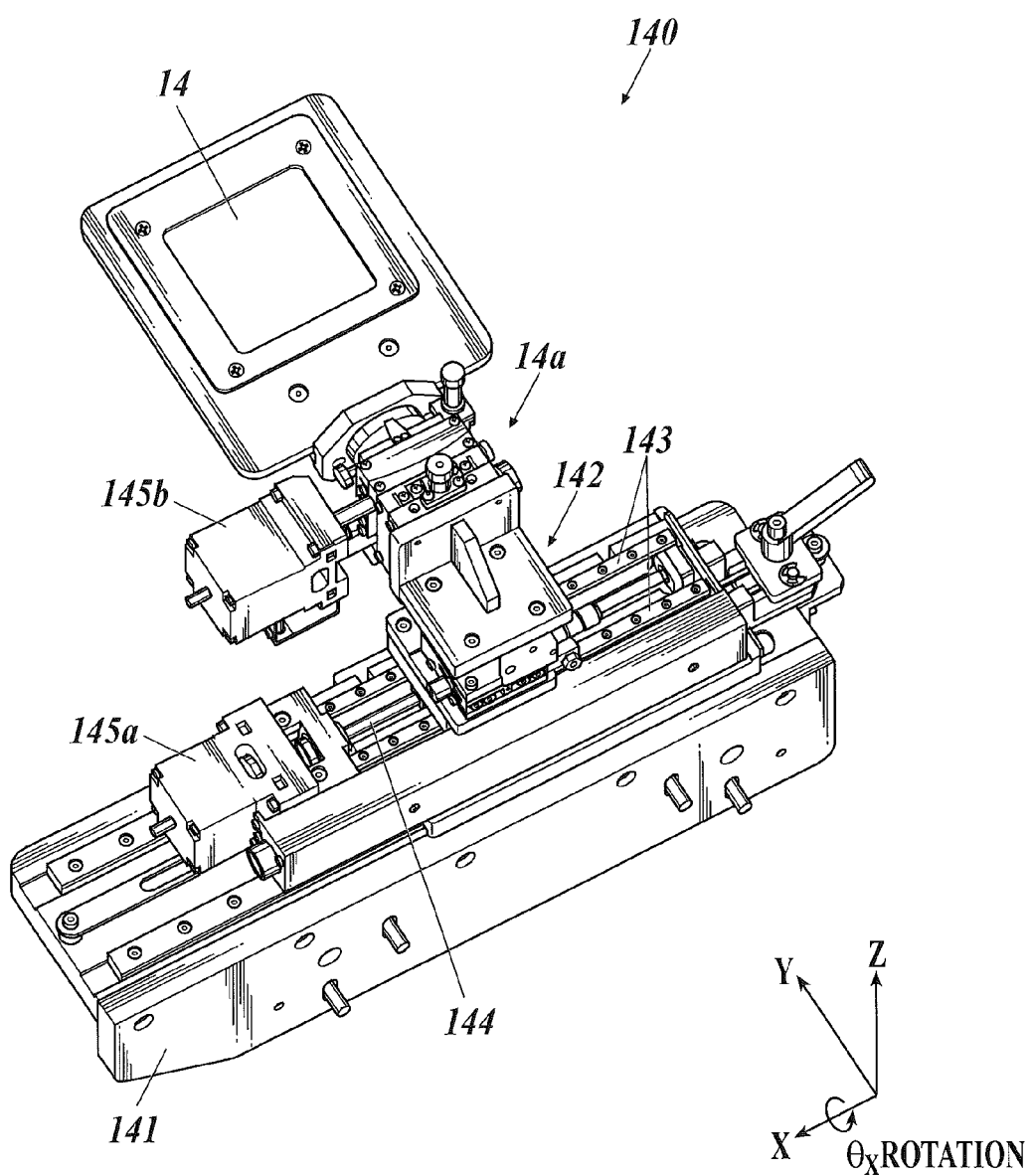
FIG. 35 is a perspective view of the first grating unit.
Figure 36:
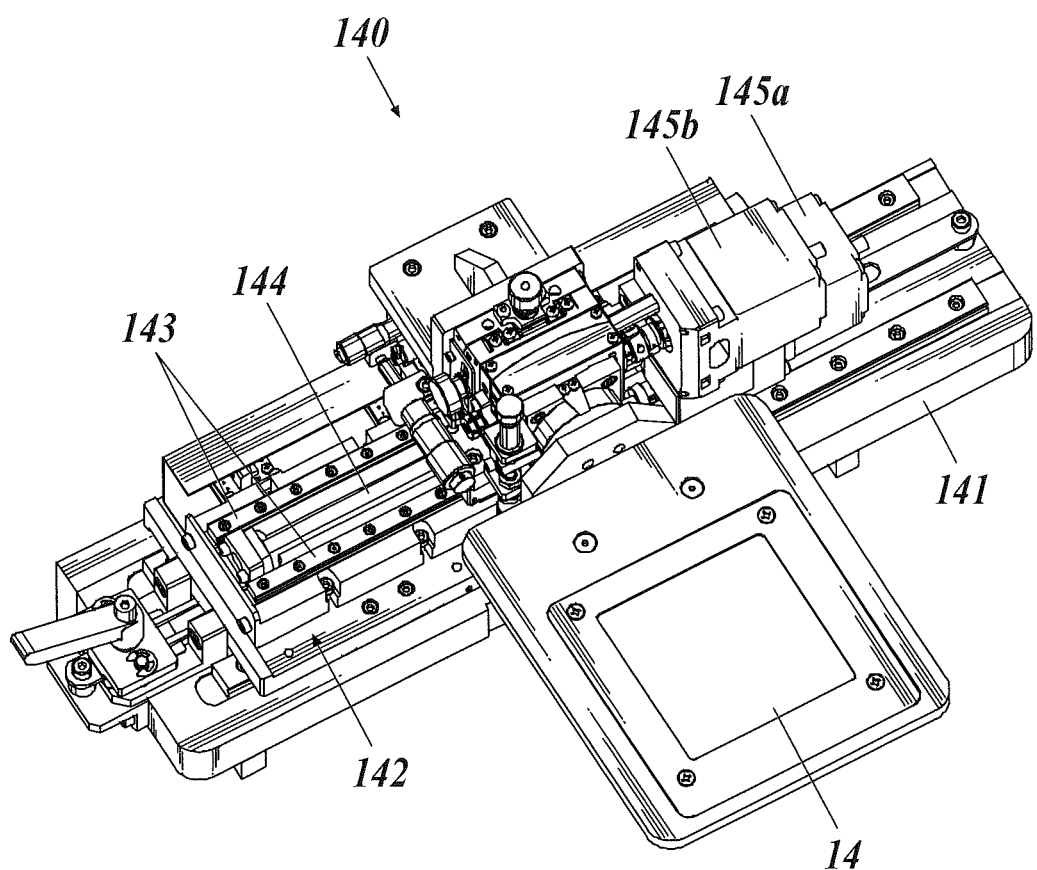
FIG. 36 is another perspective view of the first grating unit.
Figure 37:
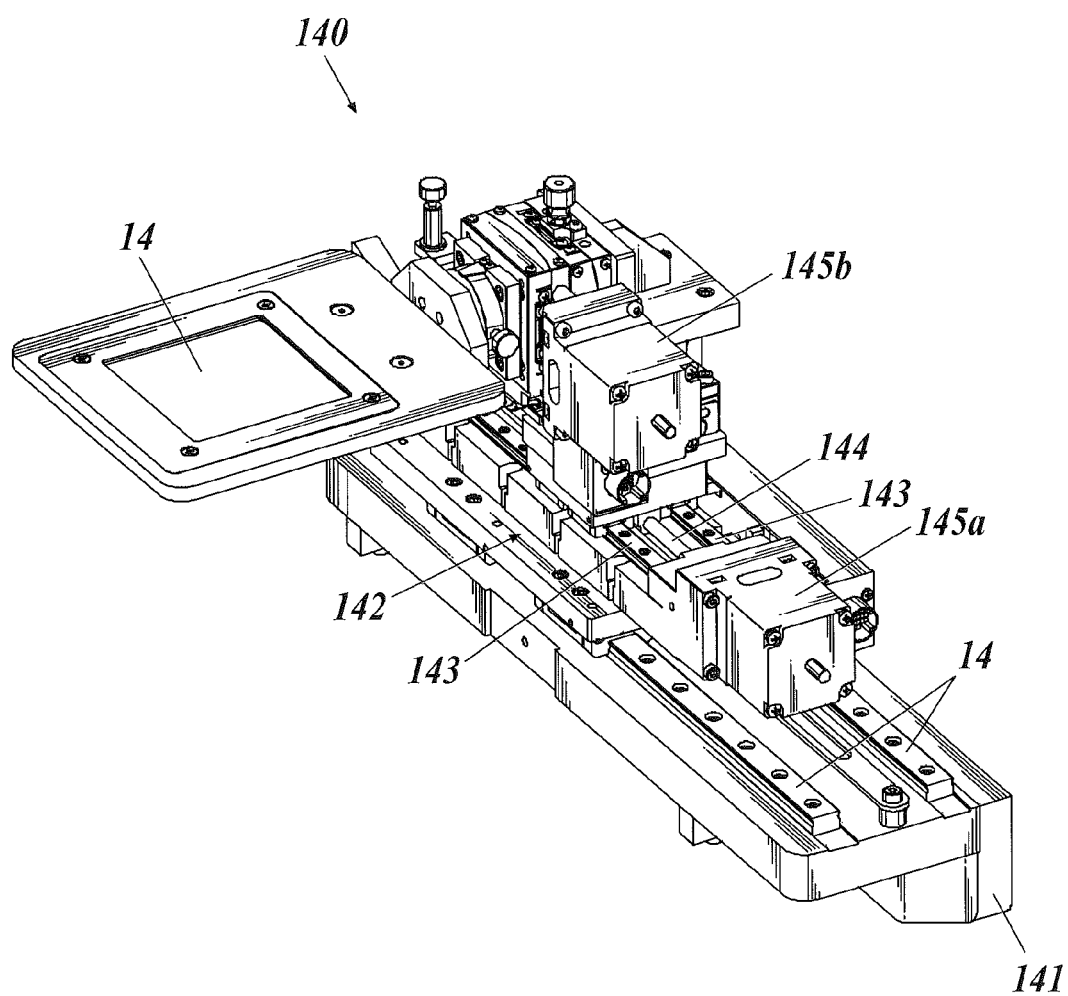
FIG. 37 is another perspective view of the first grating unit.

FIGS. 35 and 36 are perspective views of the first grating unit 140 as seen from the top. FIG. 37 is also a perspective view thereof. Note that the second grating unit 150 has the same configuration as that of the first grating unit 140; hence, illustration and a description of the unit 150 will be omitted.

The first grating unit 140 includes a substantially L-shaped base mount 141 to be secured to the support 19 and a main portion 142 of the first grating unit, as illustrated in FIGS. 35 to 37. The main portion 142 is mounted on a surface of the base mount 141 substantially horizontal to the floor surface.

The base mount 141 acts as a mechanism for the adjustment of the relative distance between the first grating 14 and the multi-slit grating 12 and between the first grating 14 and the second grating 15 by adjusting the position of the attachment to the support 19.

Linear guides 143 are provided on the top plane of the main portion 142. The guides 143 are used to move the first grating 14 in the x direction.

The main portion 142 is provided with the first grating 14 supported by a supporter 14a. In addition, the main portion 142 is provided with a motor 145a for movement in the x direction and a θx rotation motor 145b for rotating the first grating 14 about an axis extending in the x direction, as a driver 145 for moving the first grating 14.

The motor 145a is a driving source that operates under the energized state. For example, the motor 145a is a motor that can operate with high accuracy, such as a stepping motor (pulse motor), which operates in synchronization with a pulse signal, similarly to the motor 125a of the multi-slit grating unit 120.

In the present embodiment, the driving power of the motor 145a, which is a driving source, turns a ball screw 144 that transmits the output from the driving source to the supporter 14a supporting the first grating 14 to be driven, and thereby the first grating 14 supported by the supporter 14a is moved in the x direction along the linear guides 143.

The motor 145a, which is the driving source; the ball screw, which is a transmission system; and the linear guides configure a moving unit of the first grating unit 140. The moving unit consists of elements that move perpendicularly to the gravitational force (i.e., the z direction).

In order to produce suitable moire images, the accuracy of the transfer rate of the first grating 14 by the motor 145a must be 1/10 or less of each transfer distance, similarly to the multi-slit grating 12. For example, if the first grating 14 is moved five times for as many radiographic exposures to produce moire images, the first grating 14 is shifted by 1/5 of the grating pitch at each time. If the first grating 14 is moved three times for as many radiographic exposures to produce moire images, the first grating 14 is shifted by 1/3 of the grating pitch at each time. Thus, for example, if the grating pitch is 5.3 μm and the grating transfer rate is 1.33 μm, the required accuracy (relative grating position) is at most ±0.05 μm (P-P: 0.10 μm).

Similarly to the motor 125a, if current is applied to the motor 145a, the temperature thereof increases, leading to thermal expansion of the surrounding components. As a result, the first grating 14 cannot be finally transferred with accuracy and thus a misalignment may occur between static gratings. Also, microvibrations of the motor propagate through the surrounding components. For this reason, the first grating 14 cannot hold its position where the grating is accurately transferred and thus a misalignment (instability) may occur between moving gratings.

Thus, similarly to the motor 125a, the motor 145a also moves the first grating 14 with a maximum output, but during the X-ray emission, the first grating driver 145 lowers the energizing current for the motor 145a to a current that provides not more than 50% of the displacement of the first grating 14 caused by the maximum output from the motor.

Note that the energizing current (exciting current) to the motor 145a during X-ray emission is preferably determined depending on the adopted motor as appropriate, similarly to the motor 125a.

The θx rotation motor 145b is a goniometer stage including an actuator as a driving source, for example, and has a tilt adjusting mechanism for adjusting the parallelism between the multi-slit grating 12 and the first and second gratings 14 and 15. Note that a θy rotation motor and a θz rotation motor may also be provided as an additional tilt adjusting mechanism, similarly to the multi-slit grating unit 120.

A main portion 152 of the second grating unit is provided with the second grating 15 supported by a supporter. In addition, the main portion 152 is provided with a motor for movement in the x direction and a θx rotation motor for rotating the second grating 15 about an axis extending in the x direction (both not shown), as a second grating driver 155 for moving the second grating 15.

The motor for movement in the x direction of the driver 155 in the second grating 15 also requires the adjustment of the energizing current (exciting current) during X-ray emission as described above, similarly to the motor 125a of the multi-slit grating unit 120 and the motor 145a of the first grating unit 140.

Exemplary configurations of the multi-slit grating 12, the first grating 14, and the second grating 15 are as follows:

The focus diameter of the X-ray tube in the X-ray source 11: 300 (μm),

Tube voltage: 40 (kVp),

Additional filter: aluminum (1.6 (mm)),

The distance d1 from the focus of the X-ray source 11 to the multi-slit grating 12: 40 (mm), The distance d3 from the multi-slit grating 12 to the first grating 14: 1110 (mm), The distance d3+d4 from the multi-slit grating 12 to the second grating 15: 1370 (mm), The size of the multi-slit grating 12: 10 mm square, The slit pitch of the multi-slit grating 12: 22.8 (μm), The size of the first grating 14: 50 mm square, The slit pitch of the first grating 14: 4.3 (μm), The size of the second grating 15: 50 mm square, and The slit pitch of the second grating 15: 5.3 (μm).

The X-ray detector 16 has two-dimensionally arranged conversion elements that generate electrical signals depending on the emitted X-rays and reads the electrical signals generated by the conversion elements as image signals.

The pixel size of the X-ray detector 16 preferably ranges from 10 to 300 (μm), and more preferably 50 to 200 (μm).

The X-ray detector 16 is preferably fixed to the support 19 so as to be in contact with the second grating 15. It is because a moire image produced by the X-ray detector 16 is blurred as the distance between the second grating 15 and the X-ray detector 16 increases.

The X-ray detector 16 may be a flat panel detector (FPD). The FPD may be of a direct conversion type or an indirect conversion type. The FPD of the indirect conversion type converts X-rays into electrical signals through a scintillator using photoelectric conversion elements; whereas the FPD of the direct conversion type converts X-rays directly into electrical signals.

In the FPD of the indirect conversion type, photoelectric conversion elements are two-dimensionally arranged with thin film transistors (TFTs) under a scintillator plate such as CsI, $Gd_2O_3$, or $Gd_2O_2S$, and each of the elements constitute a pixel. The scintillator plate of the X-ray detector 16 absorbs incident X-rays to emit light. Electrical charges generated from the emitted light are accumulated in individual photoelectric conversion elements, and then the accumulated electrical charges are read as image signals.

In the FPD of the direct conversion type, an amorphous selenium film having a thickness of 100 to 1000 (μm) is deposited on glass by thermal evaporation of amorphous selenium where the amorphous selenium film and electrodes are deposited on the array of two-dimensionally arranged TFTs. When the amorphous selenium film absorbs X-rays, carriers are isolated in the form of electron-hole pairs in the material and voltage signals across the electrodes are read by the TFTs.

Note that the X-ray detector 16 may be an imaging unit such as a charge coupled device (CCD) or an X-ray camera.

A series of processes by the FPD during radiography will now be described.

The FPD resets itself to remove remaining electrical charges generated in the previous radiography (read). Electrical charges are then accumulated with the start of X-ray emission, and the accumulated electrical charges are read in the form of image signals after the X-ray emission. Note that immediately after the reset or after the read of image signals, the FPD may perform a dark read to detect a voltage of accumulated electrical charges. The FPD may subtract this voltage, as a correction value, from the voltage from the electrical charges accumulated during the X-ray emission, and then output the resultant voltage as image signals. As a result, the image signals can be offset-corrected.

Figure 38:
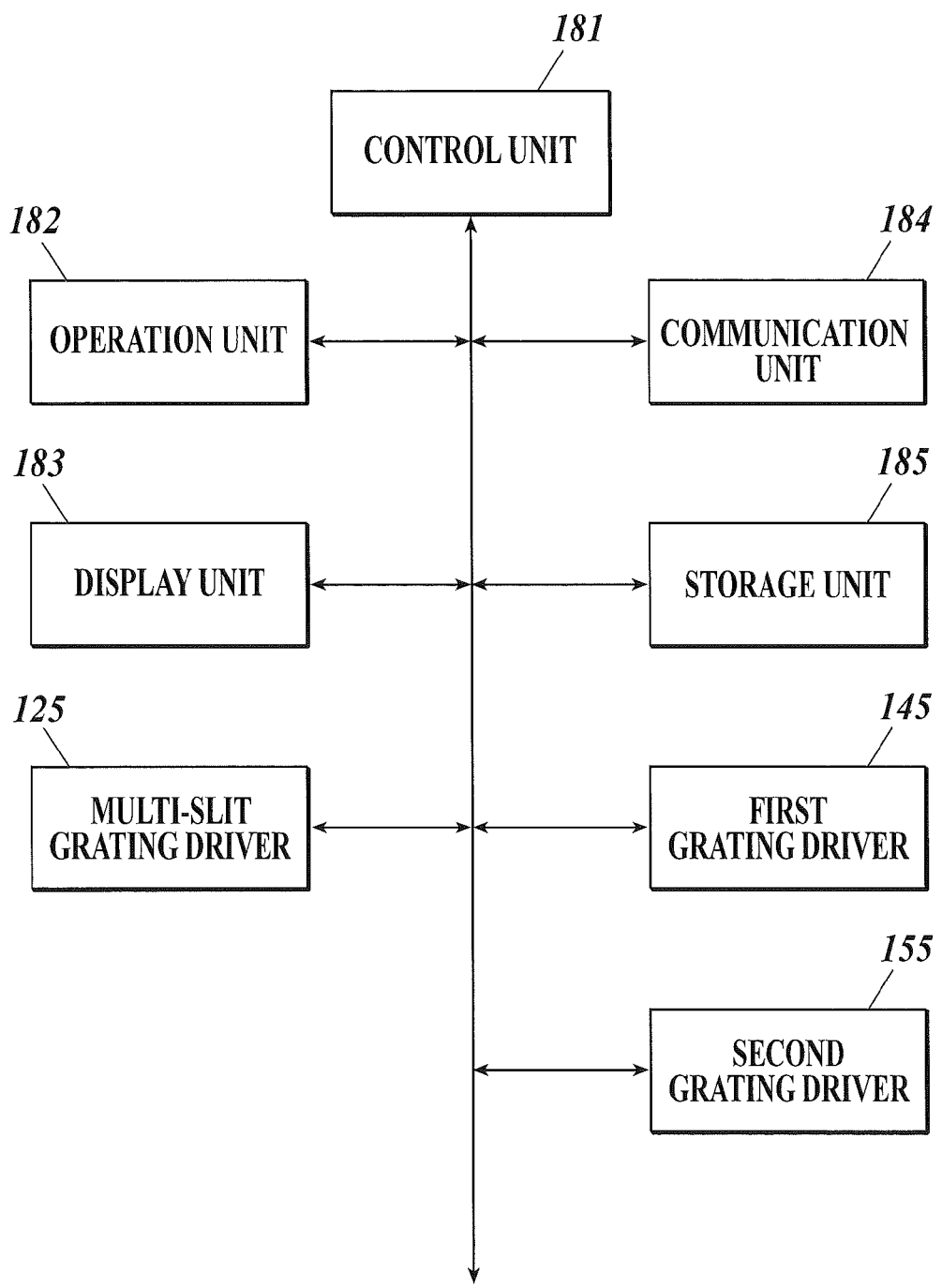
FIG. 38 is a function block diagram of a main body.

The main body 18 includes a control unit 181, an operation unit 182, a display unit 183, a communication unit 184, a storage unit 185, the multi-slit grating driver 125, the first grating driver 145, and the second grating driver 155, as illustrated in FIG. 38.

The control unit 181 includes a central processing unit (CPU) and random access memory (RAM), for example, and executes a variety of processes in cooperation with programs stored in the storage unit 185. For example, the control unit 181 controls the timing of X-ray emission from the X-ray source 11 and the timing of reading image signals by the X-ray detector 16 in accordance with information set on radiographic conditions input from the controller 5.

The operation unit 182 includes an emission switch and keys used to input radiographic conditions, for example, in addition to a touch panel integrated with the display of the display unit 183. The operation unit 182 generates operation signals in response to operations through these input sections and outputs the signals to the control unit 181.

The display unit 183 displays an operation window and operating states of the joint imaging apparatus 1 on the display in accordance with the display control by the control unit 181.

The communication unit 184 includes a communication interface to communicate with the controller 5 on a network. For example, the communication unit 184 transmits moire images read by the X-ray detector 16 and stored in the storage unit 185, to the controller 5.

The storage unit 185 stores programs to be executed by the control unit 181 and data necessary for the execution of the programs therein. The storage unit 185 also stores moire images produced by the X-ray detector 16 therein.

The multi-slit grating driver 125, the first grating driver 145, and the second grating driver 155 drive the driving sources (motors) of the multi-slit grating unit 120, the first grating unit 140, and the second grating unit 150, respectively.

The controller 5 controls the radiographic operation by the joint imaging apparatus 1 in accordance with instructions by the operator and creates a reconstructed image of a subject using moire images generated by the joint imaging apparatus 1. In the present embodiment, the controller 5 functions as an image processing device that creates a reconstructed image of a subject; however, a dedicated image processing device that processes an X-ray image in various manners may also be connected to the joint imaging apparatus 1 and this image processing device may create a reconstructed image.

The radiographic method using a Talbot-Lau interferometer of the joint imaging apparatus 1 will be described.

Figure 39:
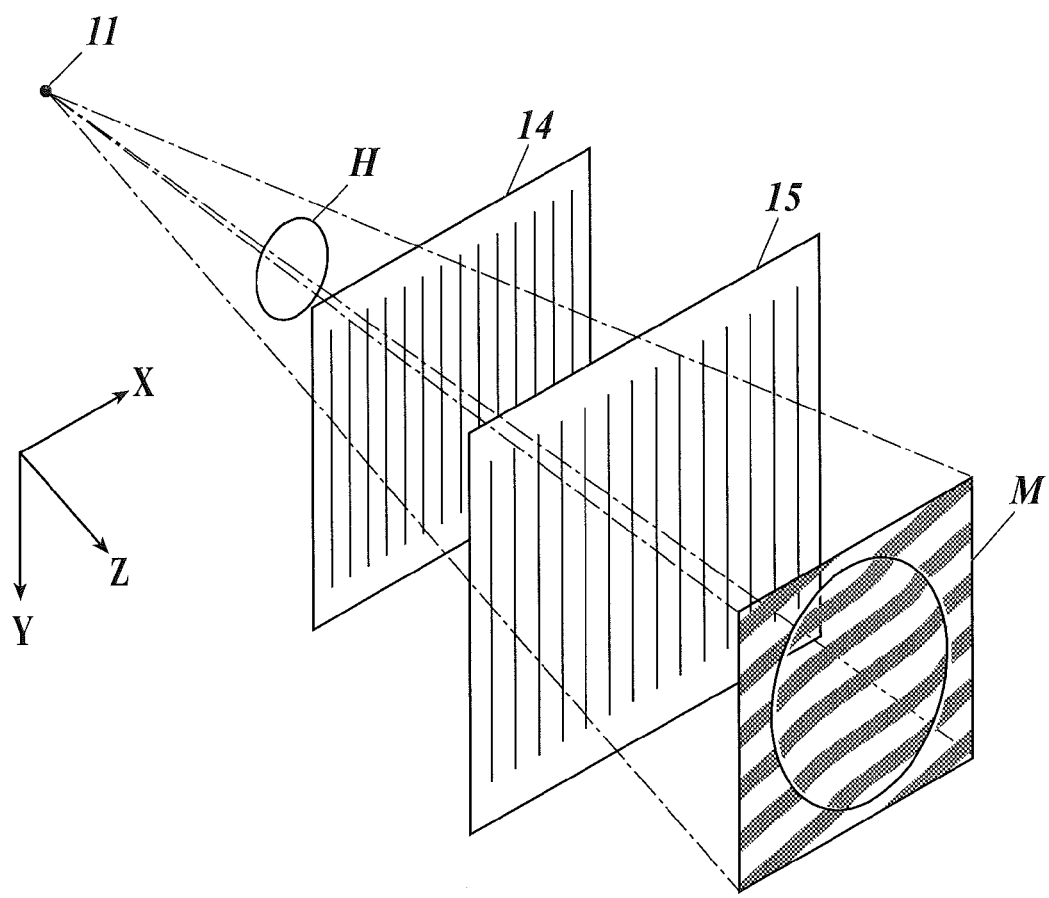
FIG. 39 illustrates the principle of a Talbot interferometer.

When X-rays emitted from the X-ray source 11 pass through the first grating 14, the X-rays are focused at fixed intervals in the z direction to form an image, as illustrated in FIG. 39. The image is called "self-image", and the phenomenon in which a self-image is formed is referred to as the Talbot effect. The second grating 15 is disposed in parallel at the position where a self-image is formed. The width direction of the slits of the second grating 15 is slightly inclined from that of the first grating 14; hence, X-rays passing through the second grating 15 give a moire image M. When a subject H is disposed between the X-ray source 11 and the first grating 14, the X-rays become out of phase due to the subject H, and thus interference fringes in the moire image M are disordered (distorted) within the contour of the subject H, as illustrated in FIG. 39. The disorder (distortion) in the interference fringes can be detected by processing the moire image M, so as to construct a subject image. This is the principle of the Talbot interferometer.

In the joint imaging apparatus 1, the multi-slit grating 12 is disposed between the X-ray source 11 and the first grating 14 and adjacent to the X-ray source 11, and a radiographic process is performed by the Talbot-Lau interferometer. Although the Talbot interferometer assumes that the X-ray source 11 is an ideal point source, actual radiography uses a focus having a relatively large diameter; hence, the multi-slit grating 12 gives a semblance of multiple light sources as if a series of point sources emit X-rays. This is the radiography by the Talbot-Lau interferometer, and the same Talbot effect as that of the Talbot interferometer can be provided even in the case of a relatively large focus diameter.

The multi-slit grating 12 of the conventional Talbot-Lau interferometers is used to create the semblance of multiple light sources as mentioned above and to increase the exposure dose, and one of the first grating 14 and the second grating 15 is moved relative to the other to create a moire image by fringe scanning. The present embodiment, however, does not adopt the relative motion of one of the first grating 14 and the second grating 15 with respect to the other, but moves the multi-slit grating 12 relative to the first and second gratings 14 and 15, with the positions of the first and second gratings 14 and 15 being fixed, and thereby a plurality of moire images are created in a fixed interval.

Figure 40:
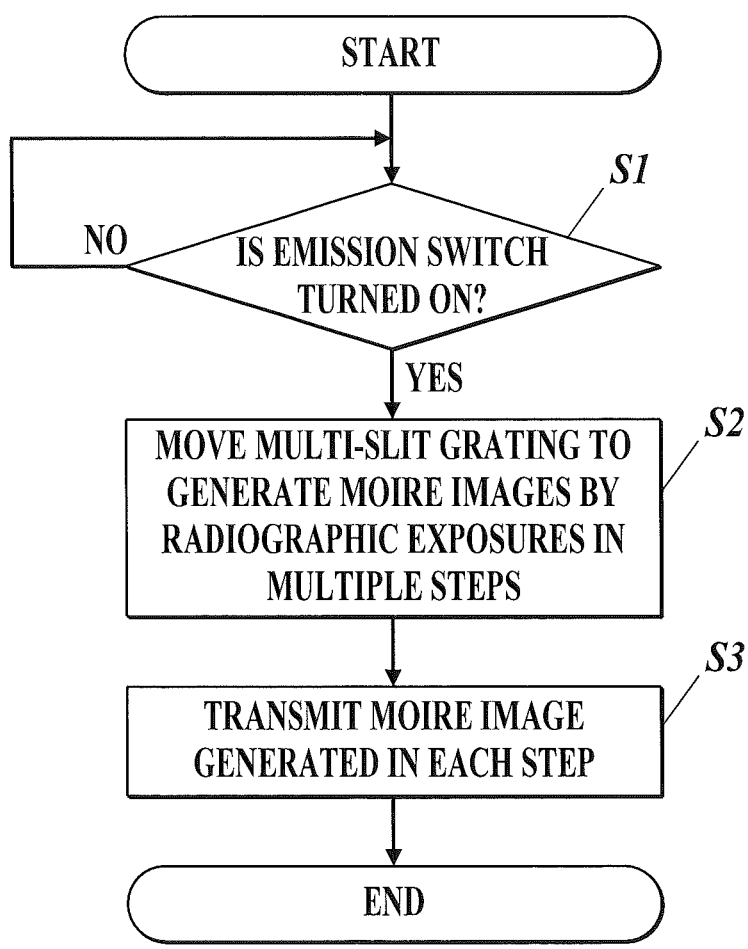
FIG. 40 is a flow chart illustrating radiographic processes with the joint imaging apparatus.

FIG. 40 is a flow chart illustrating radiographic processes with the joint imaging apparatus 1.

The above-described radiographic method utilizing the Talbot-Lau interferometer is used as the radiography, and a subject image is reconstructed by fringe scanning. The multi-slit grating 12 of the joint imaging apparatus 1 is shifted at equal intervals and the subject is radiographed in each step. As a result, a moire image is created in each step.

The number of steps preferably ranges from 2 to 20, and more preferably from 3 to 10. Five steps are most preferred in view of the creation of a highly visible reconstructed image within a short time period (see Reference (1): K. Hibino, B. F. Oreb, and D. I. Farrant, "Phase shifting for nonsinusoidal wave forms with phase-shift errors," J. Opt. Soc. Am. A, Vol. 12, 761-768 (1995), and Reference (2): A. Momose, W. Yashiro, Y. Takeda, Y. Suzuki, and T. Hattori, "Phase Tomography by X-ray Talbot Interferometry for biological imaging," Jpn. J. Appl. Phys., Vol. 45, 5254-5262 (2006)).

If the operator turns on the emission switch (step S1: YES) as illustrated in FIG. 40, the motor 125a moves the multi-slit grating 12 to multiple steps of radiographic exposures, resulting in the generation of moire images (step S2).

The X-ray source 11 first emits X-rays with the multi-slit grating 12 being static. After the X-ray detector 16 resets itself, electrical charges are accumulated in accordance with X-ray emission. The accumulated electrical charges are read as image signals when the X-ray emission stops. This is the radiographic process in one step. The multi-slit grating 12 moves when the radiographic process for one step ends, and stops after a predetermined amount of movement; thereafter, the radiographic process for the next step is performed. The multi-slit grating 12 moves and stops a given number of times, which corresponds to a predetermined number of steps, in this manner, and X-rays are emitted and image signals are read while the multi-slit grating 12 is static. The read image signals are output to the main body 18 as moire images.

For example, it is assumed that the slit pitch of the multi-slit grating 12 is 22.8 (μm) and five-step radiography is performed within 10 seconds. The radiography is performed each time the multi-slit grating 12 stops after moving by 4.56 (μm), corresponding to 1/5 of the slit pitch. In terms of radiographic time, the radiography is performed in 2, 4, 6, 8, and 10 seconds after the emission switch is turned on.

If the second grating 15 (or the first grating 14) is moved relative to the first grating 14 (or the second grating 15) as in the conventional manner, the slit pitch of the second grating 15 is relatively small and the amount of movement in each step is also small; whereas the slit pitch of the multi-slit grating 12 is relatively large compared with the second grating 15 and the amount of movement in each step is also large. For example, the amount of movement of the second grating 15 having a slit pitch of 5.3 (μm) is 1.06 (μm) in each step; whereas the amount of movement of the multi-slit grating 12 having a slit pitch of 22.8 (μm) is about four times the 1.06 (μm), i.e., 4.56 (μm). It is now assumed that the conventional scheme and the scheme in the present embodiment each use the same driving system (including a driving source and a decelerator). If radiographic exposures are performed in the individual steps with the motor 125a starting up and stopping repeatedly, both the schemes may suffer from an error in the amount of movement caused by backlash of the motor 125a occurring in start-up and stopping, for example. In such a case, the scheme in the present embodiment where the multi-slit grating 12 is moved has a smaller error in the amount of movement relative to the amount of actual movement corresponding to a controlled amount (the number of driving pulses) of a pulse motor (driving source) for movement than the conventional scheme. The fact indicates that the present embodiment can readily create a moire image based on a sine curve described later and obtain a high-definition reconstructed image even if the multi-slit grating 12 is repeatedly moved and stopped. Alternatively, if even images obtained by the conventional scheme are enough for a diagnosis, the accuracy requirement (especially, start-up and stop characteristics) of the entire driving system including a motor (driving source) may be relaxed to reduce the costs of the components of the driving system.

The main body 18 transmits the moire image in each step to the controller 5 after the radiographic process in each step (step S3). The main body 18 may transmit one created moire image to the controller 5 each time the radiographic process in one step is completed, or may collectively transmit all the moire images after the radiographic processes in all the steps are completed.

Figure 41:
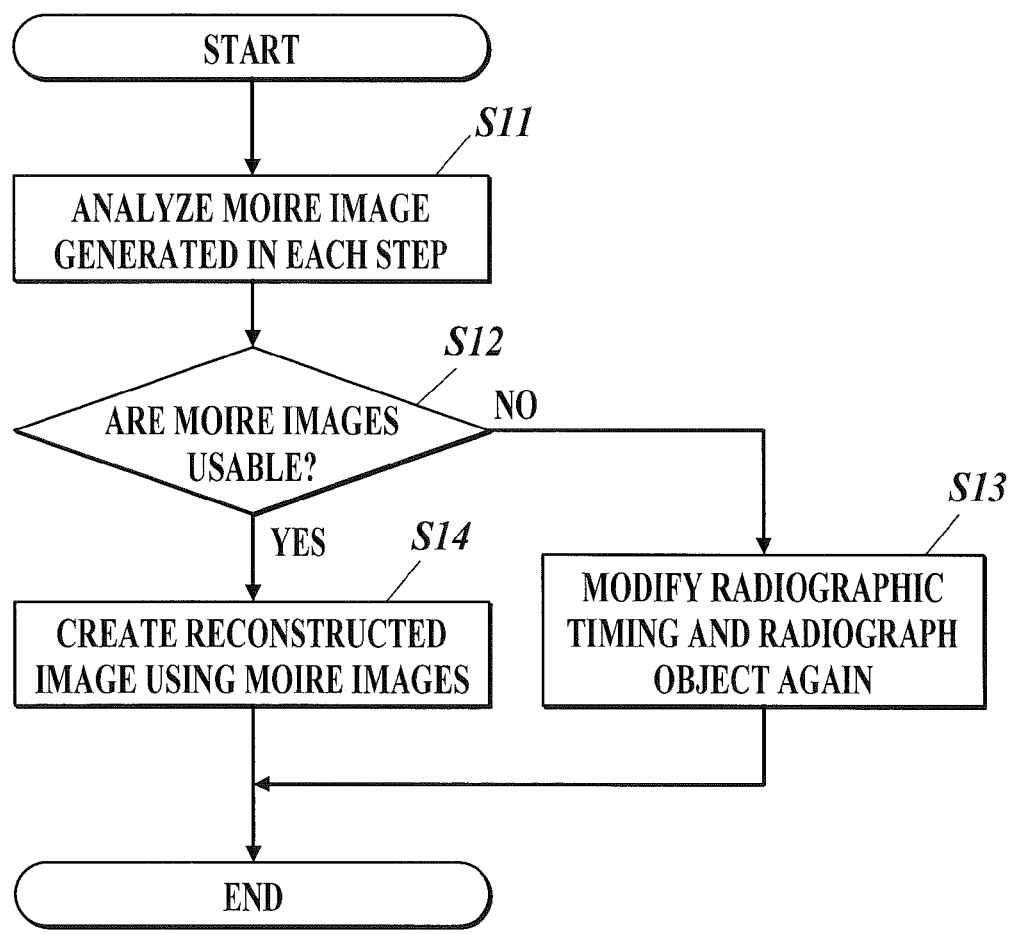
FIG. 41 is a flow chart illustrating processes by a controller.
Figure 42:
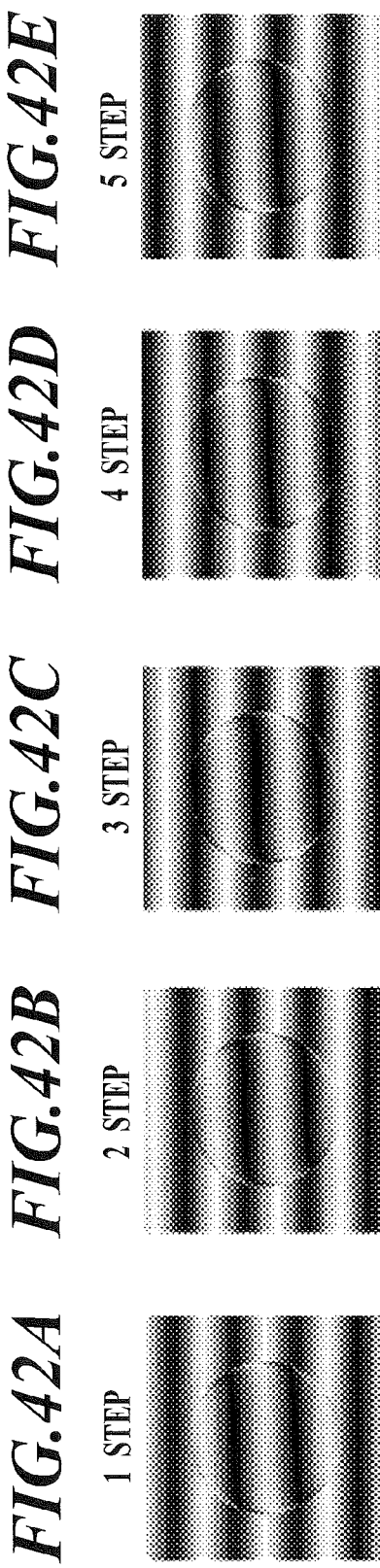
FIG. 42A illustrates radiographic moire image in Step 1.
FIG. 42B illustrates radiographic moire image in Step 2.
FIG. 42C illustrates radiographic moire image in Step 3.
FIG. 42D illustrates radiographic moire image in Step 4.
FIG. 42E illustrates radiographic moire image in Step 5.

FIG. 41 is a flow chart illustrating a flow of processes of the controller 5 after moire images are received.

Figure 43:
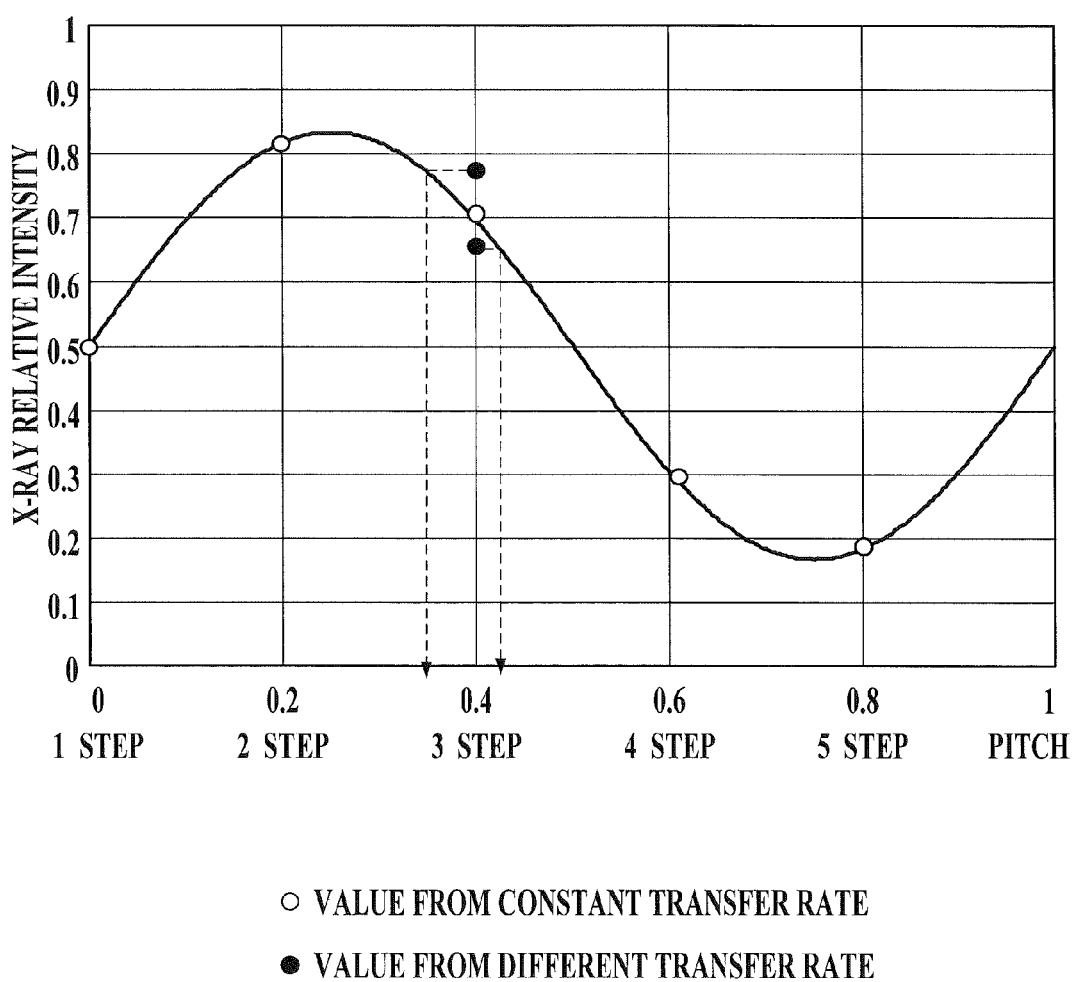
FIG. 43 is a graph illustrating X-ray relative intensities of a pixel of interest in the moire images in the respective steps.

The moire images are analyzed (step S11) to determine whether these images are usable to create a reconstructed image (step S12), as illustrated in FIG. 41. If the multi-slit grating 12 is constantly transferred with ideal accuracy, five-step radiography produces five moire images corresponding to one slit pitch of the multi-slit grating 12, as illustrated in FIGS. 42A to 42E. Since the moire images in the respective steps are created by fringe scanning in a fixed interval of 0.2 pitch, the X-ray relative intensity determined by normalizing signal values of any one pixel of the moire images traces a sine curve, as illustrated in FIG. 43. Thus, the controller 5 determines the X-ray relative intensity for a certain pixel of interest in the moire images in the respective steps. A sine curve, as illustrated in FIG. 43, of the X-ray relative intensity determined from each moire image indicates that the moire images are created in a fixed interval, so that these moire images are determined to be usable for the creation of a reconstructed image.

Note that the shape of a sine curve depends on the slit width of a multi-slit grating, the pitch of a phase grating, and the distance between phase gratings. Although the trace forms a triangle wave in the case of coherent light such as synchrotron radiation, X-rays act as quasi-coherent light by the effect of the multi-slit grating, resulting in a sine curve.

If any of the moire images in the respective steps disturbs a sine curve, it is determined that the image cannot be used for the creation of a reconstructed image (step S12: NO), and the controller 5 transmits control information on the instruction for the radiography at a different radiographic timing to the joint imaging apparatus 1 (step S13). For example, if a third-step moire image to be created at 0.4 pitch is created at 0.35 pitch, as illustrated in FIG. 43, the accuracy of transfer of the motor 125a may be reduced (e.g., due to noise occurring in a driving pulse of the pulse motor). Thus, the controller 5 may send an instruction to perform the third-step radiography again with the timing advanced by 0.05 pitch. Alternatively, the controller 5 may send an instruction to perform the radiography in all the five steps again with only the third-step radiographic time advanced by 0.05 pitch. If all the moire images in the five steps deviate from the sine curve by a predetermined amount, the controller 5 may send an instruction to increase or decrease the number of driving pulses required while the motor 125a is working.

The joint imaging apparatus 1 adjusts the radiographic timing in accordance with the control information and performs the radiographic process illustrated in FIG. 40 again.

In contrast, if it is determined that the moire images can be used for the creation of a reconstructed image (step S12: YES), the controller 5 processes the moire images to create the reconstructed image of the subject (step S14). Specifically, the controller 5 calculates the change in intensity (change in a signal value) between the steps, of every pixel of the five moire images to determine a differential phase from the change in intensity. If necessary, the phase in every step is determined using phase unwrapping. An optical path difference in the z direction (an optical path difference due to a difference in the refractive index) is calculated from the phase to create a reconstructed image representing the shape of the subject (see References (1) and (2-)). The reconstructed image is displayed on the controller 5, and thereby the operator can confirm the reconstructed image.

According to the present embodiment, the joint imaging apparatus 1 for radiographing a joint of a finger of a person as a subject includes the subject table 13. The subject table 13 includes the base unit 31 to fix the wrist of the person, and the subject fixing unit 33 to fix a joint to a predetermined position with respect to the direction of X-rays emitted from the X-ray source 11, which subject fixing unit 33 is attachable to and detachable from the base unit 31. Accordingly, even in the case where a patient who already has a lesion in a joint such as rheumatism has great difficulty in stretching the joint along the subject table 13 and keeping such a posture by his/her own, the subject can be firmly held and a positional deviation and blurring of the subject can be prevented without a burden on the patient during the radiography.

The subject fixing unit 33 can fix a joint, i.e., a subject, to a radiographically appropriate predetermined position with the wrist fixed to the wrist fixing belt 313 provided on the base unit 31. Thus, even if the patient cannot stretch the joint, the joint can be firmly fixed to prevent the bulge of the subject from the subject holder 30. This leads to the prevention of the movements of the subject caused by a slight tremor in a finger and body movements, thereby eliminating the formation of a possible blurred image and additional radiographic exposure.

The first subject fixing unit 33a to the sixth subject fixing unit 33f are prepared as the subject fixing unit 33; hence, the user or radiographer can select the most appropriate one therefrom depending on the radiographic purpose, the subject area, and the conditions of the joint of the patient fingers. Accordingly, one imaging apparatus can perform radiography in various situations, and an image appropriate for a diagnosis can be obtained with a reduced burden on the patient.

The joint imaging apparatus 1 also includes the multi-slit grating, and/or the first and second phase gratings each having multiple slits to create moire images, so that a joint can be radiographed by fringe scanning. Since the subject is fixed to the radiographic position stably during multiple radiographic exposures, an image which is free from artifact due to movements of the subject and is appropriate for a diagnosis can be obtained for joint cartilages, and soft tissues around joints, which cannot readily produce clear images due to a low difference in absorption of X-rays in the absorption-contrast method.

Furthermore, the sixth subject fixing unit 33f includes the first fixing member 350 to fix the wrist and palm, which are a part on one side of the joints of fingers (i.e., the side closer to the trunk of the person than the other side with respect to the joints), and the second fixing member 360 to fix the fingers, which are a part on the other side of the joints of fingers (i.e., the side remote from the trunk of the person with respect to the joints). The positions of the first base 361, the second bases 362, and the lower grasping members 365 of the second fixing member 360 can be adjusted relative to the first fixing member 350. For this reason, grasping of the joints of fingers and positional adjustment allow the fingers to be stretched in the proper direction. Further, moving the lower grasping members 365 with the fingers restrained by the restraint units 371 allows the fingers to be stretched in the proper direction and to be maintained in the positions during radiography.

Thus, a joint of a finger can be radiographed with the spaces between joints extended; hence, the outline of a joint cartilage, which has been difficult to image, can be clearly radiographed. Furthermore, the radiography of a stretched joint can facilitate radiographic positioning and shorten radiographic time.

Note that this embodiment is an example of the present invention, and the present invention is not limited thereto.

For example, six subject fixing units for configuring the subject holder 30, i.e., the first subject fixing unit 33a to the sixth subject fixing unit 33f, are prepared as the subject fixing units 33, and one of the units is selected therefrom and fit to the base unit 31, in the present embodiment. Instead, any type and number of subject fixing units 33 may be applied.

For example, the joint imaging apparatus 1 may include any one of them or may further include a subject fixing unit 33 having another shape.

The X-ray source 11, the multi-slit grating 12, the subject table 13, the first grating 14, the second grating 15, and the X-ray detector 16 are arranged in this order (hereinafter, referred to as "first arrangement") in the embodiment; however, a reconstructed image can be created by moving the multi-slit grating 12 while fixing the positions of the first and second gratings 14 and 15 under the arrangement of the X-ray source 11, the multi-slit grating 12, the first grating 14, the subject table 13, the second grating 15, and the X-ray detector 16 in this order (hereinafter, referred to as "second arrangement").

In the second arrangement, the center of a subject is apart from the first grating 14 by the thickness of the subject, so that the sensitivity is a little bit inferior to that of the above embodiment, whereas this arrangement effectively utilizes X-rays by an amount absorbed by the first grating 14, in terms of a reduction in exposure dose to the subject.

Effective spatial resolution at the position of a subject depends on the focus diameter of an X-ray, the spatial resolution of a detector, a magnification of the subject, and the thickness of the subject. If the spatial resolution of the detector in the above embodiment is not more than 120 μm (the full width at half maximum of a Gaussian distribution), the effective spatial resolution in the second arrangement is lower than that in the first arrangement.

The first grating 14 and the subject table 13 are preferably arranged in consideration of sensitivity, spatial resolution, and the amount of X-rays absorbed in the first grating 14.

A joint imaging apparatus using a Talbot-Lau interferometer that has a multi-slit grating, a first grating, and a second grating is taken as an example of a fringe scanning imaging apparatus in the present embodiment; however, the present invention can be applied to a joint imaging apparatus including a Talbot interferometer that has a first grating and a second grating for using fringe scanning, instead of a Talbot-Lau interferometer.

Furthermore, the joint imaging apparatus can use any scheme other than fringe scanning. For example, the present invention may be applied to a joint imaging apparatus that uses the Fourier transform or a typical phase contrast, which does not involve fringe scanning using the first and second gratings (i.e., non-scanning type). Conventional radiographic imaging using Fourier transform or a typical phase contrast requires only one radiation exposure, but often requires a long irradiation time (i.e., time for imaging). Therefore, such radiographic imaging also involves a risk of movements of the subject. In contrast, applying the present invention to the radiographic imaging can advantageously reduce such a risk.

Although the subject table 13 has been illustrated and described as a completely separate member in the present embodiment, the subject table 13 may also be secured to the support 19. In this case, a cushion is provided between the subject table 13 and the support 19 to achieve maximum possible prevention of propagation of shocks and vibrations received by the subject table 13 through the support 19.

The height of the subject table 13 may be adjusted depending on the figure of a patient.

In the present embodiment, the multi-slit grating unit 120, the first grating unit 140, and the second grating unit 150 each include a tilt adjusting mechanism and a relative distance adjusting mechanism. Alternatively, the tilt adjusting mechanism and the relative distance adjusting mechanism may be provided in at least one of the multi-slit grating unit 120, the first grating unit 140, and the second grating unit 150, instead of being provided in all of them.

A moire image is generated by moving the multi-slit grating 12 in the present embodiment. Alternatively, the first grating 14 or the second grating 15 may be moved to generate a moire image.

A cableless cassette-based FPD that includes a built-in battery and wirelessly outputs image signals to the main body 18 may also be used as the X-ray detector 16. The cassette-based FPD can obviate the need for a cable connected to the main body 18, resulting in saved space around the X-ray detector 16. This allows enough space around the feet of a patient to prevent the feet from coming into contact with the apparatus.

The control unit of the controller 5 may create a reconstructed image by the Fourier transform instead of the creation by fringe scanning (In this case, the relative angle between the first grating and the second grating of the joint imaging apparatus must be larger than the case of fringe scanning.).

For example, a reconstructed image is created using the Fourier transform in the following manner.

A moire image with a subject and a moire image without a subject are created, and each of the images is corrected by methods such as offset correction and gain correction. Then, each of the corrected moire images with and without the subject is Fourier-transformed (two-dimensional Fourier transform). The Fourier transform performed on one moire image generates a low-frequency component (referred to as "zeroth-order component") and a component having a frequency around that of interference fringes (referred to as "first-order component"), or a zeroth-order component, a first-order component, and a high-frequency component (depending on the coherence of the joint imaging apparatus 1).

The zeroth-order component is Hanning-windowed in each of the images (with and without the subject) given by the Fourier transform. As a result, values at the periphery of the Hanning window are forced to zero, and the values at the center of the Hanning window remain.

The first-order component is then shifted by a carrier frequency (i.e., a moire frequency) and Hanning-windowed, in the images given by the Fourier transform. The Gaussian window may also be used for a window function, instead of the Hamming window, depending on the particular application.

The inverse Fourier transform is then performed on each of the windowed zeroth-order and first-order components.

Reconstructed images with and without the subject are created using the resultant zeroth-order and first-order components after the inverse Fourier transform. Specifically, an absorption image is created based on the amplitude of the zeroth-order components. A phase image is created based on the phase of the first-order components. An image with small angle scattering is created based on the amplitude ratio (i.e., visibility) of the zeroth-order components and the first-order components.

Then, the reconstructed image with the subject is corrected for the removal of the phase of the interference fringes and image irregularities (artifacts), using the reconstructed image without the subject. The end of the correction of the image irregularities indicates the finish of the creation of a reconstructed image using the Fourier transform.

It is understood that the present invention can be applied to any other embodiment and varied as appropriate.

The entire disclosure of Japanese Patent Application No. 2012-045313 filed on Mar. 1, 2012 including description, claims, drawings, and abstract are incorporated herein by reference in its entirety.

Although various exemplary embodiments have been shown and described, the invention is not limited to the embodiments shown. Therefore, the scope of the invention is intended to be limited solely by the scope of the claims that follow.

What is claimed is:

1. A joint imaging apparatus for use with a person having a finger and a wrist as a subject, the joint imaging apparatus comprising:
    a subject table to hold the finger of the person in a radiographic position; and
    a radiographic unit comprising:
        a radiation generating section disposed above the subject table to irradiate a joint of the finger, and
        a detecting section disposed under the subject table to detect radiation that passes through the joint,
    wherein the subject table comprises:
        a base unit to fix the wrist of the person, and
        a first subject fixing unit to fix the joint to a first predetermined position with respect to a direction of the radiation emitted from the radiation generating section;
    wherein the first subject fixing unit comprises:
        a first fixing member to fix a part on one side of the joint, the one side being closer to a trunk of the person than the other side of the joint, and
        a second fixing member to fix a part on the other side of the joint, the second fixing member comprising a grasping unit to be moved in a direction from the wrist to a fingertip; and
    wherein a position of the second fixing member is adjustable relative to a position of the first fixing member.

2. The joint imaging apparatus according to claim 1, wherein the first subject fixing unit is attachable to and detachable from the base unit.

3. The joint imaging apparatus according to claim 1, further comprising a second subject fixing unit to fix the joint to a second predetermined position different from the first predetermined position,
    wherein each of the first and second subject fixing units is attachable to and detachable from the base unit.

4. The joint imaging apparatus according to claim 1, wherein the apparatus is a fringe scanning imaging apparatus including a first grating and a second grating each extending in a direction orthogonal to the direction of the radiation emitted from the radiation generating section and each having a plurality of slits provided at predetermined intervals.

5. The joint imaging apparatus according to claim 4, further comprising a multi-slit grating disposed adjacent to the radiation generating section,
   wherein the first grating, the second grating, and the multi-slit grating constitute a Talbot-Lau interferometer where the multi-slit grating is movable relative to the first grating and the second grating.

6. The joint imaging apparatus according claim 1, wherein the second fixing member includes a restraint unit to restrain the finger.

7. The joint imaging apparatus according claim 1, wherein the first subject fixing member includes a step for tilting up the finger to re radiographed.

8. The joint imaging apparatus according claim 1, wherein the second fixing member is adjustable in a width direction of the finger to be radiographed.

* * * * *